US012721902B2

(12) United States Patent
David et al.

(10) Patent No.: US 12,721,902 B2
(45) Date of Patent: Sep. 1, 2026

(54) COMPOSITIONS FOR TARGETING MUSCLE CELLS AND USES THEREOF

(71) Applicants: Cavalry Biosciences, Inc., San Francisco, CA (US); University of Florida Research Foundation, Incorporated, Gainesville, FL (US)

(72) Inventors: Nathaniel Eames David, San Francisco, CA (US); Robert N. O'Brien, Burlington, VT (US); Timothy R. Stowe, San Francisco, CA (US); Patrick B. Ventura, Richmond, CA (US); James W. West, Bend, OR (US); Elisabeth Barton, Gainesville, FL (US)

(73) Assignees: Cavalry Biosciences, Inc.; University of Florida Research Foundation, Incorporated, Gainsville, FL (US)

( * ) Notice: Subject to any disclaimer, the term of this patent is extended or adjusted under 35 U.S.C. 154(b) by 0 days.

(21) Appl. No.: 19/299,229

(22) Filed: Aug. 13, 2025

(65) Prior Publication Data

US 2026/0041784 A1 Feb. 12, 2026

Related U.S. Application Data

(63) Continuation of application No. PCT/US2024/055703, filed on Nov. 13, 2024.

(Continued)

(51) Int. Cl.

*A61K 47/68* (2017.01)
*A61P 21/00* (2006.01)

(Continued)

(52) U.S. Cl.

CPC ...... *A61K 47/6849* (2017.08); *A61K 47/6811* (2017.08); *A61P 21/00* (2018.01); *C07K 14/65* (2013.01); *C07K 16/2839* (2013.01)

(58) Field of Classification Search

CPC .................................................. A61K 47/6849

See application file for complete search history.

(56) References Cited

U.S. PATENT DOCUMENTS 5,330,971 A 7/1994 Wells et al.
2006/0223753 A1 10/2006 Glass (Continued)

FOREIGN PATENT DOCUMENTS

EP 1833847 B1 7/2011
WO WO-2013138643 A1 9/2013

(Continued)

OTHER PUBLICATIONS

Janeway CA Jr, Travers P, Walport M, et al. Immunobiology: The Immune System in Health and Disease. 5th edition. New York: Garland Science; 2001. The structure of a typical antibody molecule. Available from: https://www.ncbi.nlm.nih.gov/books/NBK27144/ (Year: 2001).*

(Continued)

*Primary Examiner* — Karl J Puttlitz
(74) *Attorney, Agent, or Firm* — WILSON SONSINI GOODRICH & ROSATI

(57) ABSTRACT

Disclosed herein are compositions that are useful for targeting a signaling pathway modulator to a muscle cell. In some instances, such compositions may be useful in treating a muscle disorder, such as muscular dystrophy.

13 Claims, 16 Drawing Sheets

Specification includes a Sequence Listing.

Related U.S. Application Data

(60) Provisional application No. 63/671,556, filed on Jul. 15, 2024, provisional application No. 63/598,767, filed on Nov. 14, 2023.

(51) Int. Cl.
*C07K 14/65* (2006.01)
*C07K 16/28* (2006.01)

(56) References Cited

U.S. PATENT DOCUMENTS

| | | | | |
|---|---|---|---|---|
| 2015/0182596 | A1 | 7/2015 | Lee et al. | |
| 2015/0329614 | A1 | 11/2015 | Fornaro et al. | |
| 2020/0399623 | A1* | 12/2020 | Baik | A61P 43/00 |
| 2021/0094997 | A1* | 4/2021 | Gavin | A61P 31/00 |
| 2021/0147526 | A1 | 5/2021 | Andre et al. | |

FOREIGN PATENT DOCUMENTS

| | | | |
|---|---|---|---|
| WO | WO-2015108998 | A2 | 7/2015 |
| WO | WO-2021097338 | A1 | 5/2021 |
| WO | WO-2025106529 | A2 | 5/2025 |

OTHER PUBLICATIONS

Mielenz, Dirk, et al. The Integrin alpha7 Cytoplasmic Domain Regulates Cell Migration, Lamellipodia Formation, and p130CAS/Crk Coupling. Journal of Biological Chemistry 276(16):13417-13426 (2021).

Baik, Andrew D., et al. Cell type-selective targeted delivery of a recombinant lysosomal enzyme for enzyme therapies. Molecular Therapy 29(12):3512-3524 (2021).

Francis, G L. et al. Novel Recombinant Fusion Protein Analogues of Insulin-like Growth Factor IGF)-I Indicate the Relative Importance of IGF-binding Protein and Receptor Binding for Enhanced Biological Potency. Journal of Molecular Endocrinology 8(3):213-223 (1992).

Kaufman,, Stephen J., et al. Expression of a developmentally regulated antigen on the surface of skeletal and cardiac muscle cells . . . J Cell Biol 100(6):1977-1987 (1985).

Milner, Steven J., et al. Mutations in the B-domain of insulin-like growth factor-I influence the oxidative folding to yield products with modified biological properties. Biochem. J. 308:865-871 (1995).

PCT/US2024/055703 International Search Report and Written Opinion dated Jun. 6, 2025.

Tomatis, Daniela, et al. The muscle-specific laminin receptor alpha7 beta1 integrin negatively regulates alpha5 beta1 fibronectin receptor function. Experimental Cell Research 246(2):421-432 (1999).

3D Slicer Image Computing Platform, Feb. 20, 2026; [retrieved on Feb. 23, 2026]. Available at URL:https://www.slicer.org/ pp. 1-5.

Barton-Davis, Elisabeth R. et al. Viral mediated expression of insulin-like growth factor I blocks the aging-related loss of skeletal muscle function. Proceedings of the national academy of sciences 95(26):15603-15607 (1998).

Blanco-Bose, William E., et al., Purification of mouse primary myoblasts based on α7 integrin expression. Experimental Cell Research. 265(2): 212-220 (2001).

Crawley, Suzanne, et al. , The α7β1 integrin mediates adhesion and migration of skeletal myoblasts on laminin. Experimental cell research 235 (1): 274-286 (1997).

Hammers, David W. et al. Glucocorticoids counteract hypertrophic effects of myostatin inhibition in dystrophic muscle. JCI insight 5(1):e133276, 1-16 (2020).

Heller, Kristin N., et al. AAV-mediated Overexpression of Human (alpha)7 Integrin Leads to Histological and Functional Improvement in Dystrophic Mice. Molecular Therapy 21(3):520-525 (2013).

Kaspar, Brian K. et al. Retrograde viral delivery of IGF-1 prolongs survival in a mouse ALS model. Science 301(5634):839-842 (2003).

Musarò, Antonio et al. Localized Igf-1 transgene expression sustains hypertrophy and regeneration in senescent skeletal muscle. Nature genetics 27(2):195-200 (2001).

Pelosi, Laura et al. Local expression of IGF-1 accelerates muscle regeneration by rapidly modulating inflammatory cytokines and chemokines. The FASEB Journal 21(7):1393-1402 (2007).

Prado, Carla M. et al. Muscle matters: the effects of medically induced weight loss on skeletal muscle. The Lancet Diabetes & Endocrinology 12(11):785-787 (2024).

Rozo, Michelle, et al. Targeting (beta)1-Integrin Signaling Enhances Regeneration in Aged and Dystrophic Muscle in Mice. Nature Medicine 22(8):889-896 (2016).

Rutter, Meilan M. et al. Recombinant human insulin-like growth factor-1 therapy for 6 months improves growth but not motor function in boys with Duchenne muscular dystrophy. Muscle & nerve 61(5):623-631 (2020).

Salmon Jr, W. D. A hormonally controlled serum factor which stimulates sulfate incorporation by cartilage in vitro. The Journal of Laboratory and Clinical Medicines. 49: 825-836 (1957).

Smith, Lucas R, and Elisabeth R. Barton. SMASH-semi-automatic muscle analysis using segmentation of histology: a MATLAB application. Skeletal muscle 4(1):21, 1-15 (2014).

Sorenson, Eji et al. Subcutaneous IGF-1 is not beneficial in 2-year ALS trial. Neurology 71(22):1770-1775 (2008).

Turner, Scott. Increased Laminin Binding Through α7β1 Integrin Activation Protects Dystrophic Muscle. Presented by Pliant Therapeutics, pp. 1-25 (2022).

Wahlgren, Lisa et al. Respiratory comorbidities and treatments in Duchenne muscular dystrophy: impact on life expectancy and causes of death. Journal of Neurology 271(7):4300-4309 (2024).

Zapf, J., et al. Acute metabolic effects and half-lives of intravenously administered insulinlike growth factors I and II in normal and hypophysectomized rats. The Journal of clinical investigation 77(6):1768-1775 (1986).

* cited by examiner

IGF1, $EC_{50}$= 4.6 nM

ITGA7-targeted IGF1, $EC_{50}$= 30.5 nM

IGF1, $EC_{50}$= 7.8 nM

ITGA7-targeted IGF1, $EC_{50}$= 7.1 nM

ITGA7-targeted IGF1

Statistics: A-B) Unpaired t-test C) One-way ANOVA
n = 8-10/group, *p<0.05p, **p<0.01

SEQUENCE LISTING

```
Sequence total quantity: 61
SEQ ID NO: 1            moltype = AA  length = 70
FEATURE                 Location/Qualifiers
source                  1..70
                        mol_type = protein
                        note = IGF-1 sequence
                        organism = unidentified
SEQUENCE: 1
GPETLCGAEL VDALQFVCGD RGFYFNKPTG YGSSSRRAPQ TGIVDECCFR SCDLRRLEMY  60
CAPLKPAKSA                                                         70

SEQ ID NO: 2            moltype = AA  length = 312
FEATURE                 Location/Qualifiers
source                  1..312
                        mol_type = protein
                        organism = synthetic construct
SEQUENCE: 2
GPETLCGAEL VDALQFVCGD RGFYFNKPTG YGSSSRRAPQ TGIVDECCFR SCDLRRLEMY  60
CAPLKPAKSA GGGGSGGGGS EPKSSDKTHT CPPCPAPELL GGPSVFLFPP KPKDTLMISR  120
TPEVTCVVVD VSHEDPEVKF NWYVDGVEVH NAKTKPREEQ YGSTYRVVSV LTVLHQDWLN  180
GKEYKCKVSN KALPAPIEKT ISKAKGQPRE PQVCTLPPSR DELTKNQVSL SCAVKGFYPS  240
DIAVEWESNG QPENNYKTTP PVLDSDGSFF LVSKLTVDKS RWQQGNVFSC SVMHEALHNH  300
YTQKSLSLSP GK                                                      312

SEQ ID NO: 3            moltype = AA  length = 105
FEATURE                 Location/Qualifiers
source                  1..105
                        mol_type = protein
                        organism = synthetic construct
SEQUENCE: 3
GPETLCGAEL VDALQFVCGD RGFYFNKPTG YGSSSRRAPQ TGIVDECCFR SCDLRRLEMY  60
```

```
CAPLKPAKSA RSVRAQRHTD MPKTQKEVHL KNASRGSAGN KNYRM                   105

SEQ ID NO: 4            moltype = AA  length = 147
FEATURE                 Location/Qualifiers
source                  1..147
                        mol_type = protein
                        organism = synthetic construct
SEQUENCE: 4
GPETLCGAEL VDALQFVCGD RGFYFNKPTG YGSSSRRAPQ TGIVDECCFR SCDLRRLEMY  60
CAPLKPAKSA RSVRAQRHTD MPKTQKYQPP STNKNTKSQR RKGWPKTHPG GEQKEGTEAS  120
LQIRGKKKEQ RREIGSRNAE CRGKKGK                                       147

SEQ ID NO: 5            moltype = AA  length = 110
FEATURE                 Location/Qualifiers
source                  1..110
                        mol_type = protein
                        organism = synthetic construct
SEQUENCE: 5
GPETLCGAEL VDALQFVCGD RGFYFNKPTG YGSSSRRAPQ TGIVDECCFR SCDLRRLEMY  60
CAPLKPAKSA RSVRAQRHTD MPKTQKYQPP STNKNTKSQR RKGSTFEERK             110

SEQ ID NO: 6            moltype = AA  length = 69
FEATURE                 Location/Qualifiers
source                  1..69
                        mol_type = protein
                        organism = synthetic construct
SEQUENCE: 6
GPETLCGAEL VDALQFVCGD RGFYFNKPTG YGSSSRAPQT GIVDECCFRS CDLRRLEMYC  60
APLKPAKSA                                                           69

SEQ ID NO: 7            moltype = AA  length = 104
FEATURE                 Location/Qualifiers
source                  1..104
                        mol_type = protein
                        organism = synthetic construct
SEQUENCE: 7
GPETLCGAEL VDALQFVCGD RGFYFNKPTG YGSSSRAPQT GIVDECCFRS CDLRRLEMLC  60
APLKPAKSAR SVRAQRHTDM PKTQKEVHLK NASRGSAGNK NYRM                    104

SEQ ID NO: 8            moltype = AA  length = 146
FEATURE                 Location/Qualifiers
source                  1..146
                        mol_type = protein
                        organism = synthetic construct
SEQUENCE: 8
GPETLCGAEL VDALQFVCGD RGFYFNKPTG YGSSSRAPQT GIVDECCFRS CDLRRLEMYC  60
APLKPAKSAR SVRAQRHTDM PKTQKYQPPS TNKNTKSQRR KGWPKTHPGG EQKEGTEASL  120
QIRGKKKEQR REIGSRNAEC RGKKGK                                        146

SEQ ID NO: 9            moltype = AA  length = 109
FEATURE                 Location/Qualifiers
source                  1..109
                        mol_type = protein
                        organism = synthetic construct
SEQUENCE: 9
GPETLCGAEL VDALQFVCGD RGFYFNKPTG YGSSSRAPQT GIVDECCFRS CDLRRLEMYC  60
APLKPAKSAR SVRAQRHTDM PKTQKYQPPS TNKNTKSQRR KGSTFEERK               109

SEQ ID NO: 10           moltype = AA  length = 67
FEATURE                 Location/Qualifiers
source                  1..67
                        mol_type = protein
                        organism = synthetic construct
SEQUENCE: 10
TLCGAELVDA LQFVCGDRGF YFNKPTGYGS SSRRAPQTGI VDECCFRSCD LRRLEMYCAP  60
LKPAKSA                                                             67

SEQ ID NO: 11           moltype = AA  length = 70
FEATURE                 Location/Qualifiers
source                  1..70
                        mol_type = protein
                        organism = synthetic construct
SEQUENCE: 11
GPRTLCGAEL VDALQFVCGD RGFYFNKPTG YGSSSRRAPQ TGIVDECCFR SCDLRRLEMY  60
CAPLKPAKSA                                                          70

SEQ ID NO: 12           moltype = AA  length = 191
FEATURE                 Location/Qualifiers
source                  1..191
```

```
                         mol_type = protein
                         organism = synthetic construct
SEQUENCE: 12
FPTIPLSRLF DNAMLRAHRL HQLAFDTYQE FEEAYIPKEQ KYSFLQNPQT SLCFSESIPT  60
PSNREETQQK SNLELLRISL LLIQSWLEPV QFLRSVFANS LVYGASDSNV YDLLKDLEEG  120
IQTLMGRLED GSPRTGQIFK QTYSKFDTNS HNDDALLKNY GLLYCFRKDM DKVETFLRIV  180
QCRSVEGSCG F                                                      191

SEQ ID NO: 13            moltype = AA  length = 433
FEATURE                  Location/Qualifiers
source                   1..433
                         mol_type = protein
                         organism = synthetic construct
SEQUENCE: 13
FPTIPLSRLF DNAMLRAHRL HQLAFDTYQE FEEAYIPKEQ KYSFLQNPQT SLCFSESIPT  60
PSNREETQQK SNLELLRISL LLIQSWLEPV QFLRSVFANS LVYGASDSNV YDLLKDLEEG  120
IQTLMGRLED GSPRTGQIFK QTYSKFDTNS HNDDALLKNY GLLYCFRKDM DKVETFLRIV  180
QCRSVEGSCG FGGGGSGGGG SEPKSSDKTH TCPPCPAPEL LGGPSVFLFP PKPKDTLMIS  240
RTPEVTCVVV DVSHEDPEVK FNWYVDGVEV HNAKTKPREE QYGSTYRVVS VLTVLHQDWL  300
NGKEYKCKVS NKALPAPIEK TISKAKGQPR EPQVCTLPPS RDELTKNQVS LSCAVKGFYP  360
SDIAVEWESN GQPENNYKTT PPVLDSDGSF FLVSKLTVDK SRWQQGNVFS CSVMHEALHN  420
HYTQKSLSLS PGK                                                    433

SEQ ID NO: 14            moltype = AA  length = 146
FEATURE                  Location/Qualifiers
source                   1..146
                         mol_type = protein
                         organism = synthetic construct
SEQUENCE: 14
PALPEDGGSG AFPPGHFKDP KRLYCKNGGF FLRIHPDGRV DGVREKSDPH IKLQLQAEER  60
GVVSIKGVCA NRYLAMKEDG RLLASKCVTD ECFFFERLES NNYNTYRSRK YTSWYVALKR  120
TGQYKLGSKT GPGQKAILFL PMSAKS                                      146

SEQ ID NO: 15            moltype = AA  length = 388
FEATURE                  Location/Qualifiers
source                   1..388
                         mol_type = protein
                         organism = synthetic construct
SEQUENCE: 15
PALPEDGGSG AFPPGHFKDP KRLYCKNGGF FLRIHPDGRV DGVREKSDPH IKLQLQAEER  60
GVVSIKGVCA NRYLAMKEDG RLLASKCVTD ECFFFERLES NNYNTYRSRK YTSWYVALKR  120
TGQYKLGSKT GPGQKAILFL PMSAKSGGGG SGGGGSEPKS SDKTHTCPPC PAPELLGGPS  180
VFLFPPKPKD TLMISRTPEV TCVVVDVSHE DPEVKFNWYV DGVEVHNAKT KPREEQYGST  240
YRVVSVLTVL HQDWLNGKEY KCKVSNKALP APIEKTISKA KGQPREPQVC TLPPSRDELT  300
KNQVSLSCAV KGFYPSDIAV EWESNGQPEN NYKTTPPVLD SDGSFFLVSK LTVDKSRWQQ  360
GNVFSCSVMH EALHNHYTQK SLSLSPGK                                    388

SEQ ID NO: 16            moltype = AA  length = 146
FEATURE                  Location/Qualifiers
source                   1..146
                         mol_type = protein
                         organism = synthetic construct
SEQUENCE: 16
PALPEDGGSG AFPPGHFKDP KRLYCKNGGF FLRIHPDGRV DGVREKSDPH IKLQLQAEER  60
GVVSIKGVCA NRYLAMKEDG RLLASKCVTD ECFFFERLES NNYNTYRSRK YTSWYVALKR  120
TGQYKLGSKT GPGQKAILFL PMSAKS                                      146

SEQ ID NO: 17            moltype = AA  length = 379
FEATURE                  Location/Qualifiers
source                   1..379
                         mol_type = protein
                         organism = synthetic construct
SEQUENCE: 17
GSCPPCPAPE LLGGPSVFLF PPKPKDTLMI SRTPEVTCVV VDVSHEDPEV KFNWYVDGVE  60
VHNAKTKPRE EQYGSTYRVV SVLTVLHQDW LNGKEYKCKV SNKALPAPIE KTISKAKGQP  120
REPQVCTLPP SRDELTKNQV SLSCAVKGFY PSDIAVEWES NGQPENNYKT TPPVLDSDGS  180
FFLVSKLTVD KSRWQQGNVF SCSVMHEALH NHYTQKSLSL SPGGGGGSGG GGSPALPEDG  240
GSGAFPPGHF KDPKRLYCKN GGFFLRIHPD GRVDGVREKS DPHIKLQLQA EERGVVSIKG  300
VCANRYLAMK EDGRLLASKC VTDECFFFER LESNNYNTYR SRKYTSWYVA LKRTGQYKLG  360
SKTGPGQKAI LFLPMSAKS                                              379

SEQ ID NO: 18            moltype = AA  length = 129
FEATURE                  Location/Qualifiers
source                   1..129
                         mol_type = protein
                         organism = synthetic construct
SEQUENCE: 18
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
```

```
REKYSKCSS                                                  129

SEQ ID NO: 19          moltype = AA  length = 371
FEATURE                Location/Qualifiers
source                 1..371
                       mol_type = protein
                       organism = synthetic construct
SEQUENCE: 19
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
REKYSKCSSG GGGSGGGGSE PKSSDKTHTC PPCPAPELLG GPSVFLFPPK PKDTLMISRT  180
PEVTCVVVDV SHEDPEVKFN WYVDGVEVHN AKTKPREEQY GSTYRVVSVL TVLHQDWLNG  240
KEYKCKVSNK ALPAPIEKTI SKAKGQPREP QVCTLPPSRD ELTKNQVSLS CAVKGFYPSD  300
IAVEWESNGQ PENNYKTTPP VLDSDGSFFL VSKLTVDKSR WQQGNVFSCS VMHEALHNHY  360
TQKSLSLSPG K                                               371

SEQ ID NO: 20          moltype = AA  length = 129
FEATURE                Location/Qualifiers
source                 1..129
                       mol_type = protein
                       organism = synthetic construct
SEQUENCE: 20
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
REKYSKCSS                                                  129

SEQ ID NO: 21          moltype = AA  length = 362
FEATURE                Location/Qualifiers
source                 1..362
                       mol_type = protein
                       organism = synthetic construct
SEQUENCE: 21
GSCPPCPAPE LLGGPSVFLF PPKPKDTLMI SRTPEVTCVV VDVSHEDPEV KFNWYVDGVE  60
VHNAKTKPRE EQYGSTYRVV SVLTVLHQDW LNGKEYKCKV SNKALPAPIE KTISKAKGQP  120
REPQVCTLPP SRDELTKNQV SLSCAVKGFY PSDIAVEWES NGQPENNYKT TPPVLDSDGS  180
FFLVSKLTVD KSRWQQGNVF SCSVMHEALH NHYTQKSLSL SPGGGGGSGG GGSHKCDITL  240
QEIIKTLNSL TEQKTLCTEL TVTDIFAASK NTTEKETFCR AATVLRQFYS HHEKDTRCLG  300
ATAQQFHRHK QLIRFLKRLD RNLWGLAGLN SCPVKEANQS TLENFLERLK TIMREKYSKC  360
SS                                                         362

SEQ ID NO: 22          moltype = AA  length = 8
FEATURE                Location/Qualifiers
source                 1..8
                       mol_type = protein
                       organism = synthetic construct
SEQUENCE: 22
GYTFTSSY                                                   8

SEQ ID NO: 23          moltype = AA  length = 8
FEATURE                Location/Qualifiers
source                 1..8
                       mol_type = protein
                       organism = synthetic construct
SEQUENCE: 23
INPVSGST                                                   8

SEQ ID NO: 24          moltype = AA  length = 6
FEATURE                Location/Qualifiers
source                 1..6
                       mol_type = protein
                       organism = synthetic construct
SEQUENCE: 24
GGWFDY                                                     6

SEQ ID NO: 25          moltype = AA  length = 9
FEATURE                Location/Qualifiers
source                 1..9
                       mol_type = protein
                       organism = synthetic construct
SEQUENCE: 25
SSDVGSYNY                                                  9

SEQ ID NO: 26          moltype = AA  length = 4
FEATURE                Location/Qualifiers
source                 1..4
                       mol_type = protein
                       organism = synthetic construct
SEQUENCE: 26
GVSK                                                       4
```

```
SEQ ID NO: 27            moltype = AA  length = 11
FEATURE                  Location/Qualifiers
source                   1..11
                         mol_type = protein
                         organism = synthetic construct
SEQUENCE: 27
GTFAGGSYYG V                                                       11

SEQ ID NO: 28            moltype = AA  length = 115
FEATURE                  Location/Qualifiers
source                   1..115
                         mol_type = protein
                         organism = synthetic construct
SEQUENCE: 28
QVQLVQSGAE VKKPGASVKV SCKASGYTFT SSYINWVRQA PGQGLEWMGT INPVSGSTSY  60
AQKFQGRVTM TRDTSISTAY MELSRLRSDD TAVYYCARGG WFDYWGQGTL VTVSS       115

SEQ ID NO: 29            moltype = AA  length = 111
FEATURE                  Location/Qualifiers
source                   1..111
                         mol_type = protein
                         organism = synthetic construct
SEQUENCE: 29
QSALTQPASV SGSPGQSITI SCTGTSSDVG SYNYVNWYQQ HPGKAPKLMI YGVSKRPSGV  60
SNRFSGSKSG NTASLTISGL QAEDEADYYC GTFAGGSYYG VFGGGTKLTV L           111

SEQ ID NO: 30            moltype = AA  length = 572
FEATURE                  Location/Qualifiers
source                   1..572
                         mol_type = protein
                         organism = synthetic construct
SEQUENCE: 30
DIVMTQGALP NPVPSGESVS ITCRSSKSLL YSDGKTYLNW YLQRPGQSPQ LLIYWMSTRA  60
SGVSDRFSGS GSGTDFTLKI SGVEAEDVGV YYCQQGLEFP DTFGAGTKLE LKGGGGSGGG  120
GSGGGGSQVQ LVQSGAEVKK PGASVKVSCK ASGYTFTSSY INWVRQAPGQ GLEWMGTINP  180
VSGSTSYAQK FQGRVTMTRD TSISTAYMEL SRLRSDDTAV YYCARGGWFD YWGQGTLVTV  240
SSASTKGPSV FPLAPSSKST SGGTAALGCL VKDYFPEPVT VSWNSGALTS GVHTFPAVLQ  300
SSGLYSLSSV VTVPSSSLGT QTYICNVNHK PSNTKVDKKV EPKSCDKTHT CPPCPAPELL  360
GGPSVFLFPP KPKDTLMISR TPEVTCVVVD VSHEDPEVKF NWYVDGVEVH NAKTKPREEQ  420
YGSTYRVVSV LTVLHQDWLN GKEYKCKVSN KALPAPIEKT ISKAKGQPRE PQVCTLPPSR  480
DELTKNQVSL SCAVKGFYPS DIAVEWESNG QPENNYKTTP PVLDSDGSFF LVSKLTVDKS  540
RWQQGNVFSC SVMHEALHNH YTQKSLSLSP GK                                572

SEQ ID NO: 31            moltype = AA  length = 8
FEATURE                  Location/Qualifiers
source                   1..8
                         mol_type = protein
                         organism = synthetic construct
SEQUENCE: 31
GFTFSNYD                                                           8

SEQ ID NO: 32            moltype = AA  length = 8
FEATURE                  Location/Qualifiers
source                   1..8
                         mol_type = protein
                         organism = synthetic construct
SEQUENCE: 32
ISYDGSRN                                                           8

SEQ ID NO: 33            moltype = AA  length = 10
FEATURE                  Location/Qualifiers
source                   1..10
                         mol_type = protein
                         organism = synthetic construct
SEQUENCE: 33
TTADNYWFAY                                                         10

SEQ ID NO: 34            moltype = AA  length = 11
FEATURE                  Location/Qualifiers
source                   1..11
                         mol_type = protein
                         organism = synthetic construct
SEQUENCE: 34
KSLLYSDGKT Y                                                       11

SEQ ID NO: 35            moltype =   length =
SEQUENCE: 35
000
```

```
SEQ ID NO: 36           moltype = AA  length = 10
FEATURE                 Location/Qualifiers
source                  1..10
                        mol_type = protein
                        organism = synthetic construct
SEQUENCE: 36
CQQGLEFPDT                                                        10

SEQ ID NO: 37           moltype = AA  length = 117
FEATURE                 Location/Qualifiers
source                  1..117
                        mol_type = protein
                        organism = synthetic construct
SEQUENCE: 37
EVQLVESGGG LVQPGRSMKV SCAASGFTFS NYDMAWVRQA PTKGLEWVAS ISYDGSRNYY  60
RDSVKGRFTI SRDNAKSTLY LQMDSLRSED TATYYCTTAD NYWFAYWGQG TLVTVSS     117

SEQ ID NO: 38           moltype = AA  length = 112
FEATURE                 Location/Qualifiers
source                  1..112
                        mol_type = protein
                        organism = synthetic construct
SEQUENCE: 38
DIVMTQGALP NPVPSGESVS ITCRSSKSLL YSDGKTYLNW YLQRPGQSPQ ILIYWMSTRA  60
SGVSDRFSGS GSGTDFTLKI SGVEAEDVGV YYCQQGLEFP DTFGAGTKLE LK          112

SEQ ID NO: 39           moltype = AA  length = 447
FEATURE                 Location/Qualifiers
source                  1..447
                        mol_type = protein
                        organism = synthetic construct
SEQUENCE: 39
EVQLVESGGG LVQPGRSMKV SCAASGFTFS NYDMAWVRQA PTKGLEWVAS ISYDGSRNYY  60
RDSVKGRFTI SRDNAKSTLY LQMDSLRSED TATYYCTTAD NYWFAYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYGSTY  300
RVVSVLTVLH QDWLNGKEYK CKVSNKALPA PIEKTISKAK GQPREPQVYT LPPCRDELTK  360
NQVSLWCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 40           moltype = AA  length = 219
FEATURE                 Location/Qualifiers
source                  1..219
                        mol_type = protein
                        organism = synthetic construct
SEQUENCE: 40
DIVMTQGALP NPVPSGESVS ITCRSSKSLL YSDGKTYLNW YLQRPGQSPQ LLIYWMSTRA  60
SGVSDRFSGS GSGTDFTLKI SGVEAEDVGV YYCQQGLEFP DTFGAGTKLE LKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 41           moltype = AA  length = 15
FEATURE                 Location/Qualifiers
source                  1..15
                        mol_type = protein
                        organism = synthetic construct
SEQUENCE: 41
GGGGSGGGGS GGGGS                                                  15

SEQ ID NO: 42           moltype = AA  length = 10
FEATURE                 Location/Qualifiers
source                  1..10
                        mol_type = protein
                        organism = synthetic construct
SEQUENCE: 42
GGGGSGGGGS                                                        10

SEQ ID NO: 43           moltype =   length =
SEQUENCE: 43
000

SEQ ID NO: 44           moltype = AA  length = 350
FEATURE                 Location/Qualifiers
source                  1..350
                        mol_type = protein
                        organism = synthetic construct
SEQUENCE: 44
```

```
DIVMTQGALP NPVPSGESVS ITCRSSKSLL YSDGKTYLNW YLQRPGQSPQ LLIYWMSTRA  60
SGVSDRFSGS GSGTDFTLKI SGVEAEDVGV YYCQQGLEFP DTFGAGTKLE LKGGGGSGGG  120
GSGGGGSQVQ LVQSGAEVKK PGASVKVSCK ASGYTFTSSY INWVRQAPGQ GLEWMGTINP  180
VSGSTSYAQK FQGRVTMTRD TSISTAYMEL SRLRSDDTAV YYCARGGWFD YWGQGTLVTV  240
SSASTKGPSV FPLAPSSKST SGGTAALGCL VKDYFPEPVT VSWNSGALTS GVHTFPAVLQ  300
SSGLYSLSSV VTVPSSSLGT QTYICNVNHK PSNTKVDKKV EPKSCDKTHT             350

SEQ ID NO: 45          moltype =   length =
SEQUENCE: 45
000

SEQ ID NO: 46          moltype = AA  length = 311
FEATURE                Location/Qualifiers
source                 1..311
                       mol_type = protein
                       organism = synthetic construct
SEQUENCE: 46
GPETLCGAEL VDALQFVCGD RGFYFNKPTG YGSSSRAPQT GIVDECCFRS CDLRRLEMYC  60
APLKPAKSAG GGGSGGGGSE PKSSDKTHTC PPCPAPELLG GPSVFLFPPK PKDTLMISRT  120
PEVTCVVVDV SHEDPEVKFN WYVDGVEVHN AKTKPREEQY GSTYRVVSVL TVLHQDWLNG  180
KEYKCKVSNK ALPAPIEKTI SKAKGQPREP QVCTLPPSRD ELTKNQVSLS CAVKGFYPSD  240
IAVEWESNGQ PENNYKTTPP VLDSDGSFFL VSKLTVDKSR WQQGNVFSCS VMHEALHNHY  300
TQKSLSLSPG K                                                       311

SEQ ID NO: 47          moltype = AA  length = 312
FEATURE                Location/Qualifiers
source                 1..312
                       mol_type = protein
                       organism = synthetic construct
SEQUENCE: 47
GPETLCGAEL VDALQFVCGD RGFLFNKPTG YGSSSRRAPQ TGIVDECCFR SCDLRRLEMY  60
CAPLKPAKSA GGGGSGGGGS EPKSSDKTHT CPPCPAPELL GGPSVFLFPP KPKDTLMISR  120
TPEVTCVVVD VSHEDPEVKF NWYVDGVEVH NAKTKPREEQ YGSTYRVVSV LTVLHQDWLN  180
GKEYKCKVSN KALPAPIEKT ISKAKGQPRE PQVCTLPPSR DELTKNQVSL SCAVKGFYPS  240
DIAVEWESNG QPENNYKTTP PVLDSDGSFF LVSKLTVDKS RWQQGNVFSC SVMHEALHNH  300
YTQKSLSLSP GK                                                      312

SEQ ID NO: 48          moltype = AA  length = 312
FEATURE                Location/Qualifiers
source                 1..312
                       mol_type = protein
                       organism = synthetic construct
SEQUENCE: 48
GPETLCGAEL VDALQFVCGD RGFYFNKPTG AGSSSRRAPQ TGIVDECCFR SCDLRRLEMY  60
CAPLKPAKSA GGGGSGGGGS EPKSSDKTHT CPPCPAPELL GGPSVFLFPP KPKDTLMISR  120
TPEVTCVVVD VSHEDPEVKF NWYVDGVEVH NAKTKPREEQ YGSTYRVVSV LTVLHQDWLN  180
GKEYKCKVSN KALPAPIEKT ISKAKGQPRE PQVCTLPPSR DELTKNQVSL SCAVKGFYPS  240
DIAVEWESNG QPENNYKTTP PVLDSDGSFF LVSKLTVDKS RWQQGNVFSC SVMHEALHNH  300
YTQKSLSLSP GK                                                      312

SEQ ID NO: 49          moltype = AA  length = 311
FEATURE                Location/Qualifiers
source                 1..311
                       mol_type = protein
                       organism = synthetic construct
SEQUENCE: 49
GPETLCGAEL VDALQFVCGD RGFYFNKPTG YGSSSRAPQT GIVDECCFRS CDLRRLEMYC  60
APLKPAKSAG GGGSGGGGSE PKSSDKTHTC PPCPAPELLG GPSVFLFPPK PKDTLMISRT  120
PEVTCVVVDV SHEDPEVKFN WYVDGVEVHN AKTKPREEQY GSTYRVVSVL TVLHQDWLNG  180
KEYKCKVSNK ALPAPIEKTI SKAKGQPREP QVCTLPPSRD ELTKNQVSLS CAVKGFYPSD  240
IAVEWESNGQ PENNYKTTPP VLDSDGSFFL VSKLTVDKSR WQQGNVFSCS VMHEALHNHY  300
TQKSLSLSPG K                                                       311

SEQ ID NO: 50          moltype = AA  length = 312
FEATURE                Location/Qualifiers
source                 1..312
                       mol_type = protein
                       organism = synthetic construct
SEQUENCE: 50
GPETLCGAEL VDALQFVCGD RGFLFNKPTG YGSSSRRAPQ TGIVDECCFR SCDLRRLEMY  60
CAPLKPAKSA GGGGSGGGGS EPKSSDKTHT CPPCPAPELL GGPSVFLFPP KPKDTLMISR  120
TPEVTCVVVD VSHEDPEVKF NWYVDGVEVH NAKTKPREEQ YGSTYRVVSV LTVLHQDWLN  180
GKEYKCKVSN KALPAPIEKT ISKAKGQPRE PQVCTLPPSR DELTKNQVSL SCAVKGFYPS  240
DIAVEWESNG QPENNYKTTP PVLDSDGSFF LVSKLTVDKS RWQQGNVFSC SVMHEALHNH  300
YTQKSLSLSP GK                                                      312

SEQ ID NO: 51          moltype = AA  length = 447
FEATURE                Location/Qualifiers
source                 1..447
```

```
                        mol_type = protein
                        organism = synthetic construct
SEQUENCE: 51
EVQLVESGGG LVQPGRSMKV SCAASGFTFS NYDMAWVRQA PTKGLEWVAS ISYDGSRNYY  60
RDSVKGRFTI SRDNAKSTLY LQMDSLRSED TATYYCTTAD NYWFAYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYGSTY  300
RVVSVLTVLH QDWLNGKEYK CKVSNKALPA PIEKTISKAK GQPREPQVYT LPPCRDELTK  360
NQVSLWCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 52           moltype = AA  length = 219
FEATURE                 Location/Qualifiers
source                  1..219
                        mol_type = protein
                        organism = synthetic construct
SEQUENCE: 52
DIVMTQGALP NPVPSGESVS ITCRSSKSLL YSDGKTYLNW YLQRPGQSPQ LLIYWMSTRA  60
SGVSDRFSGS GSGTDFTLKI SGVEAEDVGV YYCQQGLEFP DTFGAGTKLE LKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 53           moltype = AA  length = 447
FEATURE                 Location/Qualifiers
source                  1..447
                        mol_type = protein
                        organism = synthetic construct
SEQUENCE: 53
EVQLVESGGG LVQPGRSMKV SCAASGFTFS NYDMAWVRQA PTKGLEWVAS ISYDGSRNYY  60
RDSVKGRFTI SRDNAKSTLY LQMDSLRSED TATYYCTTAD NYWFAYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYGSTY  300
RVVSVLTVLH QDWLNGKEYK CKVSNKALPA PIEKTISKAK GQPREPQVYT LPPCRDELTK  360
NQVSLWCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 54           moltype = AA  length = 219
FEATURE                 Location/Qualifiers
source                  1..219
                        mol_type = protein
                        organism = synthetic construct
SEQUENCE: 54
DIVMTQGALP NPVPSGESVS ITCRSSKSLL YSDGKTYLNW YLQRPGQSPQ LLIYWMSTRA  60
SGVSDRFSGS GSGTDFTLKI SGVEAEDVGV YYCQQGLEFP DTFGAGTKLE LKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 55           moltype = AA  length = 447
FEATURE                 Location/Qualifiers
source                  1..447
                        mol_type = protein
                        organism = synthetic construct
SEQUENCE: 55
EVQLVESGGG LVQPGRSMKV SCAASGFTFS NYDMAWVRQA PTKGLEWVAS ISYDGSRNYY  60
RDSVKGRFTI SRDNAKSTLY LQMDSLRSED TATYYCTTAD NYWFAYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYGSTY  300
RVVSVLTVLH QDWLNGKEYK CKVSNKALPA PIEKTISKAK GQPREPQVYT LPPCRDELTK  360
NQVSLWCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 56           moltype = AA  length = 219
FEATURE                 Location/Qualifiers
source                  1..219
                        mol_type = protein
                        organism = synthetic construct
SEQUENCE: 56
DIVMTQGALP NPVPSGESVS ITCRSSKSLL YSDGKTYLNW YLQRPGQSPQ LLIYWMSTRA  60
SGVSDRFSGS GSGTDFTLKI SGVEAEDVGV YYCQQGLEFP DTFGAGTKLE LKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 57           moltype = AA  length = 455
FEATURE                 Location/Qualifiers
source                  1..455
                        mol_type = protein
```

-continued

```
                         organism = synthetic construct
SEQUENCE: 57
QVQLQESGPG LVKPSGTLSL TCAVSGVSIR SINWWNWVRQ PPGKGLEWIG EIYHSGSTNY  60
NPSLKSRVTI SVDKSKNQFS LKLNSVTAAD TAVYYCARDG GIAVTDYYYY GLDVWGQGTT  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYGSTYRV VSVLTVLHQD WLNGKEYKCK VSNKALPAPI EKTISKAKGQ PREPQVYTLP  360
PCRDELTKNQ VSLWCLVKGF YPSDIAVEWE SNGQPENNYK TTPPVLDSDG SFFLYSKLTV  420
DKSRWQQGNV FSCSVMHEAL HNHYTQKSLS LSPGK                            455

SEQ ID NO: 58            moltype = AA  length = 213
FEATURE                  Location/Qualifiers
source                   1..213
                         mol_type = protein
                         organism = synthetic construct
SEQUENCE: 58
EIVLTQSPAT LSLSPGERAT LSCRASESVS SNLAWYQQKP GQAPRLLIYG AFNRATGIPA  60
RFSGSGSGTD FTLTISSLEP EDFAVYYCQQ RSDWFTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 59            moltype = AA  length = 455
FEATURE                  Location/Qualifiers
source                   1..455
                         mol_type = protein
                         organism = synthetic construct
SEQUENCE: 59
QVQLQESGPG LVKPSGTLSL TCAVSGVSIR SINWWNWVRQ PPGKGLEWIG EIYHSGSTNY  60
NPSLKSRVTI SVDKSKNQFS LKLNSVTAAD TAVYYCARDG GIAVTDYYYY GLDVWGQGTT  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYGSTYRV VSVLTVLHQD WLNGKEYKCK VSNKALPAPI EKTISKAKGQ PREPQVYTLP  360
PCRDELTKNQ VSLWCLVKGF YPSDIAVEWE SNGQPENNYK TTPPVLDSDG SFFLYSKLTV  420
DKSRWQQGNV FSCSVMHEAL HNHYTQKSLS LSPGK                            455

SEQ ID NO: 60            moltype = AA  length = 213
FEATURE                  Location/Qualifiers
source                   1..213
                         mol_type = protein
                         organism = synthetic construct
SEQUENCE: 60
EIVLTQSPAT LSLSPGERAT LSCRASESVS SNLAWYQQKP GQAPRLLIYG AFNRATGIPA  60
RFSGSGSGTD FTLTISSLEP EDFAVYYCQQ RSDWFTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 61            moltype = RNA  length = 36
FEATURE                  Location/Qualifiers
source                   1..36
                         mol_type = other RNA
                         organism = synthetic construct
SEQUENCE: 61
ctctctgtcg agactcatat gttttagagc tatgct                           36
```

COMPOSITIONS FOR TARGETING MUSCLE CELLS AND USES THEREOF

CROSS-REFERENCE

This application is a continuation of International Patent Application PCT/US2024/055703, filed Nov. 13, 2024, which claims the benefit of U.S. Provisional Application No. 63/598,767 filed Nov. 14, 2023, and U.S. Provisional Application No. 63/671,556 filed Jul. 15, 2024, which are incorporated herein by reference in their entirety.

SEQUENCE LISTING

The instant application contains a Sequence Listing which has been submitted electronically in XML file format and is hereby incorporated by reference in its entirety. Said XML copy, created on Aug. 13, 2025, is named 61766-721_301_SL.xml and is 62,632 bytes in size.

SUMMARY

The present disclosure provides an agent for selectively targeting a muscle cell, the agent comprising (a) an antigen-binding domain that selectively binds to a mammalian ITGA7 and (b) a cargo that is coupled to the antigen-binding domain that selectively binds to the mammalian ITGA7. In some embodiments, the cargo comprises a vector. In some embodiments, the vector is a non-viral vector. In some embodiments, the vector is a viral vector. In some embodiments, the viral vector is an adeno-associated virus (AAV). In some embodiments, the cargo comprises a lipid nanoparticle. In some embodiments, the cargo comprises a nucleic acid. In some embodiments, the nucleic acid comprises a ribonucleic acid (RNA). In some embodiments, the RNA is a small interfering RNA (siRNA). In some embodiments, the RNA is a short hairpin RNA (shRNA). In some embodiments, the cargo comprises an antisense oligonucleotide (ASO). In some embodiments, the ASO is a morpholino. In some embodiments, the cargo comprises a drug. In some embodiments, the cargo comprises a toxin. In some embodiments, the cargo comprises an immune modulator. In some embodiments, the immune modulator is an interleukin. In some embodiments, the immune modulator decreases an activity of an immune system. In some embodiments, the interleukin is an IL-10, IL-35, IL-4, IL-13, IL-27, or IL-37. In some embodiments, the antigen-binding domain binds to an epitope expressed in a mammalian cell selected from the group consisting of a muscle satellite cell, a skeletal muscle cell, a cardiac muscle cell, and a muscle fiber. In some embodiments, the antigen-binding domain comprises a fragment antigen-binding (Fab) domain or a single chain variable fragment (scFv). In some embodiments, the antigen-binding domain comprises any one of SEQ ID NOS: 31-40. In some embodiments, the antigen-binding domain comprises: a VH CDR1 comprising an amino acid sequence having at least about 70%, at least about 80%, at least about 90%, at least about 95%, or 100% sequence identity to the sequence set forth in SEQ ID NO: 31; a VH CDR2 comprising an amino acid sequence having at least about 70%, at least about 80%, at least about 90%, at least about 95%, or 100% sequence identity to the sequence set forth in SEQ ID NO: 32; and a VH CDR3 comprising an amino acid sequence having at least about 70%, at least about 80%, at least about 90%, at least about 95%, or 100% sequence identity to the sequence set forth in SEQ ID NO: 33. In some embodiments, the antigen-binding domain comprises: a VL CDR1 comprising an amino acid sequence having at least about 70%, at least about 80%, at least about 90%, at least about 95%, or 100% sequence identity to the sequence set forth in SEQ ID NO: 34, a VL CDR2 comprising an amino acid sequence having at least about 70%, at least about 80%, at least about 90%, at least about 95%, or 100% sequence identity to the sequence set forth in SEQ ID NO: 35, and a VL CDR3 comprising an amino acid sequence having at least about 70%, at least about 80%, at least about 90%, at least about 95%, or 100% sequence identity to the sequence set forth in SEQ ID NO: 36. In some embodiments, the antigen-binding domain comprises: a variable light (VL) chain comprising an amino acid sequence having at least about 90%, at least about 95%, at least about 98%, at least about 99%, or 100% sequence identity to the sequence set forth in SEQ ID NO: 38, and a variable heavy (VH) chain knob comprising an amino acid sequence having at least about 90%, at least about 95%, at least about 98%, at least about 99%, or 100% sequence identity to the sequence set forth in SEQ ID NO: 37. In some embodiments, the linker couples the cargo to the antigen-binding domain that selectively binds to the mammalian ITGA7. In some embodiments, the agent further comprises a fragment crystallizable domain (Fc domain). In some embodiments, the Fc domain is a human IgG1 Fc domain. In some embodiments, the Fc domain comprises a knob-in-hole. In some embodiments, the antigen-binding domain comprises (i) a human IgG1 heavy chain with knob mutations and a N297G mutation and (ii) a light chain. In some embodiments, the human IgG1 heavy chain comprises an amino acid sequence having at least about 90%, at least about 95%, at least about 98%, or at least about 99% sequence identity to the sequence set forth in SEQ ID NO: 39. In some embodiments, the light chain comprises an amino acid sequence having at least about 90%, at least about 95%, at least about 98%, or at least about 99% sequence identity to the sequence set forth in SEQ ID NO: 40.

In another aspect, the present disclosure provides a pharmaceutical composition comprising (i) the agent described herein and (ii) one or more pharmaceutically acceptable excipient(s).

In another aspect, the present disclosure provides a method of modulating a muscular dystrophy, the method comprising administering the agent described herein to a subject. In another aspect, the present disclosure provides a method of selectively targeting a muscle cell, the method comprising administering the agent described herein to a subject. In some embodiments, the subject is a mammal. In some embodiments, the mammal is a human. In some embodiments, the agent is delivered to a muscle cell or a region adjacent to a muscle cell. In some embodiments, the administering comprises injecting the subject at a location near a skeletal muscle, a muscle satellite cell (e.g., a skeletal muscle satellite cell), a skeletal muscle, a cardiac muscle, a smooth muscle, or a muscle fiber. In some embodiments, the muscular dystrophy comprises Duchenne muscular dystrophy (DMD), Becker muscular dystrophy (BMD), a limb-girdle muscular dystrophy (LGMD), and/or a congenital muscular dystrophy.

In another aspect, the present disclosure provides an agent configured to selectively target a modulator to mammalian cells that express an integrin alpha 7 (ITGA7), the agent comprising: (a) a modulator; and (b) an antigen binding domain that selectively binds to a mammalian ITGA7; wherein the modulator is coupled to the antigen-binding domain that selectively binds to the mammalian ITGA7. In another aspect, the present disclosure provides an agent configured to selectively target a signaling pathway modulator to mammalian cells that express an integrin alpha 7 (ITGA7), the agent comprising: (a) a signaling pathway modulator; and (b) an antigen binding domain that selectively binds to a mammalian ITGA7; wherein the signaling pathway modulator is coupled to the antigen-binding domain that selectively binds to the mammalian ITGA7. In some embodiments, the signaling pathway modulator modulates an insulin-like growth factor 1 (IGF-1) signaling pathway. In some embodiments, the signaling pathway modulator comprises an IGF-1 polypeptide. In some embodiments, the IGF-1 polypeptide is a wild-type form of IGF-1. In some embodiments, the IGF-1 polypeptide comprises a polypeptide with a decreased ability to activate an IGF-1 receptor (IGF-1R) relative to an endogenous IGF-1. In some embodiments, the ability of the polypeptide to activate the IGF-1R is decreased by at least about 5-fold. In some embodiments, the IGF-1 polypeptide comprises an IGF-1 variant. In some embodiments, the IGF-1 variant comprises an amino acid sequence of any one of SEQ ID NOS: 1-11, or an amino acid sequence having at least about 90%, at least about 95%, at least about 98%, at least about 99%, or 100% sequence identity to a sequence set forth in any one of SEQ ID NOS: 1-11. In some embodiments, the signaling pathway modulator modulates a growth hormone (GH) signaling pathway. In some embodiments, the signaling pathway modulator modulates a growth hormone receptor (GHR). In some embodiments, the signaling pathway modulator comprises a GHR activator. In some embodiments, the signaling pathway modulator comprises a GH polypeptide. In some embodiments, the GH polypeptide comprises an amino acid sequence of SEQ ID NO: 12 or 13, or an amino acid sequence having at least about 90%, at least about 95%, at least about 98%, or at least about 99% sequence identity to the sequence set forth in SEQ ID NO: 12 or 13. In some embodiments, the signaling pathway modulator modulates a basic fibro-blast growth factor (bFGF) signaling pathway. In some embodiments, the signaling pathway modulator modulates a fibro-blast growth factor receptor (FGFR). In some embodiments, the signaling pathway modulator comprises an FGFR activator. In some embodiments, the signaling pathway modulator comprises a bFGF polypeptide. In some embodiments, the bFGF polypeptide comprises an amino acid sequence of any one of SEQ ID NOS: 14-17, or an amino acid sequence having at least about 90%, at least about 95%, at least about 98%, or at least about 99% sequence identity to the sequence set forth in any one of SEQ ID NOS: 14-17. In some embodiments, the signaling pathway modulator modulates an interleukin 4 (IL4) signaling pathway. In some embodiments, the signaling pathway modulator modulates an interleukin 4 receptor (IL4R). In some embodiments, the signaling pathway modulator comprises an IL4R activator. In some embodiments, the signaling pathway modulator comprises an IL4 polypeptide. In some embodiments, the IL4 polypeptide comprises an amino acid sequence of any one of SEQ ID NOS: 18-21, or an amino acid sequence having at least about 90%, at least about 95%, at least about 98%, or at least about 99% sequence identity to the sequence set forth in any one of SEQ ID NOS: 18-21. In some embodiments, the signaling pathway modulator modulates an activin type II receptor (ActRII). In some embodiments, the signaling pathway modulator comprises an ActRII inhibitor. In some embodiments, the signaling pathway modulator comprises bimagrumab. In some embodiments, the signaling pathway modulator is an antibody or antibody fragment. In some embodiments, the antibody or antibody fragment comprises: a VH complementarity determining region 1 (VH CDR1) comprising an amino acid sequence having at least about 70%, at least about 80%, at least about 90%, at least about 95%, or 100% sequence identity to the sequence set forth in SEQ ID NO: 22, a VH CDR2 comprising an amino acid sequence having at least about 70%, at least about 80%, at least about 90%, at least about 95%, or 100% sequence identity to the sequence set forth in SEQ ID NO: 23, and a VH CDR3 comprising an amino acid sequence having at least about 70%, at least about 80%, at least about 90%, at least about 95%, or 100% sequence identity to the sequence set forth in SEQ ID NO: 24. In some embodiments, the antibody or antibody fragment comprises: a VL CDR1 (VL CDR1) comprising an amino acid sequence having at least about 70%, at least about 80%, at least about 90%, at least about 95%, or 100% sequence identity to the sequence set forth in SEQ ID NO: 25, a VL CDR2 comprising an amino acid sequence having at least about 70%, at least about 80%, at least about 90%, at least about 95%, or 100% sequence identity to the sequence set forth in SEQ ID NO: 26, and a VL CDR3 comprising an amino acid sequence having at least about 70%, at least about 80%, at least about 90%, at least about 95%, or 100% sequence identity to the sequence set forth in SEQ ID NO: 27. In some embodiments, the antibody or antibody fragment comprises a variable heavy (VH) chain comprising an amino acid sequence having at least about 90%, at least about 95%, at least about 98%, at least about 99%, or 100% sequence identity to the sequence set forth in SEQ ID NO: 28. In some embodiments, the antibody or antibody fragment comprises a variable light (VL) chain comprising an amino acid sequence having at least about 90%, at least about 95%, at least about 98%, at least about 99%, or 100% sequence identity to the sequence set forth in SEQ ID NO: 29. In some embodiments, the antibody or antibody fragment comprises an amino acid sequence of SEQ ID NO: 30, or an amino acid sequence having at least about 90%, at least about 95%, at least about 98%, or at least about 99% sequence identity to the sequence set forth in SEQ ID NO: 30 or 44. In some embodiments, the antigen binding domain binds to an epitope expressed in a mammalian cell selected from the group consisting of a muscle satellite cell, a skeletal muscle cell, a cardiac muscle cell, and a muscle fiber. In some embodiments, the antigen binding domain comprises a fragment antigen-binding (Fab) domain or a single chain variable fragment (scFv). In some embodiments, the antigen binding domain comprises: a VH complementarity determining region 1 (VH CDR1) comprising an amino acid sequence having at least about 70%, at least about 80%, at least about 90%, at least about 95%, or 100% sequence identity to the sequence set forth in SEQ ID NO: 31, a VH CDR2 comprising an amino acid sequence having at least about 70%, at least about 80%, at least about 90%, at least about 95%, or 100% sequence identity to the sequence set forth in SEQ ID NO: 32, and a VH CDR3 comprising an amino acid sequence having at least about 70%, at least about 80%, at least about 90%, at least about 95%, or 100% sequence identity to the sequence set forth in SEQ ID NO: 33. In some embodiments, the antigen binding domain comprises: a VL CDR1 (VL CDR1) comprising an amino acid sequence having at least about 70%, at least about 80%, at least about 90%, at least about 95%, or 100% sequence identity to the sequence set forth in SEQ ID NO: 34, a VL CDR2 comprising an amino acid sequence having at least about 70%, at least about 80%, at least about 90%, at least about 95%, or 100% sequence identity to the sequence set forth in SEQ ID NO: 35, and a VL CDR3 comprising an amino acid sequence having at least about 70%, at least about 80%, at least about 90%, at least about 95%, or 100% sequence identity to the sequence set forth in SEQ ID NO: 36. In some embodiments, the antigen binding domain comprises: a variable light (VL) chain comprising an amino acid sequence having at least about 90%, at least about 95%, at least about 98%, at least about 99%, or 100% sequence identity to the sequence set forth in SEQ ID NO: 38, and a variable heavy (VH) chain knob comprising an amino acid sequence having at least about 90%, at least about 95%, at least about 98%, at least about 99%, or 100% sequence identity to the sequence set forth in SEQ ID NO: 37. In some embodiments, the signaling pathway modulator is coupled to an amino terminus of the antigen binding domain. In some embodiments, the signaling pathway modulator is coupled to a carboxy terminus of the antigen binding domain. In some embodiments, the linker couples the signaling pathway modulator to the antigen-binding domain that selectively binds to the mammalian ITGA7. In some embodiments, the agent further comprises a fragment crystallizable domain (Fc domain). In some embodiments, the Fc domain is a human IgG1 Fc domain. In some embodiments, the Fc domain comprises a knob-in-hole. In some embodiments, (a) the signaling pathway modulator comprises an amino acid sequence of any one of SEQ ID NOS: 1-30, or an amino acid sequence having at least about 90%, at least about 95%, at least about 98%, or at least about 99% sequence identity to the sequence set forth in any one of SEQ ID NOS: 1-30, wherein the C-terminus or N-terminus of the signaling pathway modulator is coupled to a linker of GGGGSGGGGSGGGGS (SEQ ID NO: 41) or GGGGSGGGGS (SEQ ID NO: 42) and a human IgG1 Fc domain with a hole and N297G mutation; and (b) the antigen binding domain comprising a human IgG1 heavy chain with knob mutations and a N297G mutation and a light chain. In some embodiments, the human IgG1 heavy chain comprises an amino acid sequence having at least about 90%, at least about 95%, at least about 98%, or at least about 99% sequence identity to the sequence set forth in SEQ ID NO: 39. In some embodiments, the light chain comprises an amino acid sequence having at least about 90%, at least about 95%, at least about 98%, or at least about 99% sequence identity to the sequence set forth in SEQ ID NO: 40. In some embodiments, the agent comprises a human IgG1 heavy chain comprising an amino acid sequence having at least about 90%, at least about 95%, at least about 98%, or at least about 99% sequence identity to the sequence set forth in SEQ ID NO: 39, and a light chain comprising an amino acid sequence having at least about 90%, at least about 95%, at least about 98%, or at least about 99% sequence identity to the sequence set forth in SEQ ID NO: 40. In some embodiments, the agent comprises a human IgG1 heavy chain comprising SEQ ID NO: 39 and a light chain comprising SEQ ID NO: 40. In some embodiments, the agent comprises a heavy chain comprising an amino acid sequence having at least about 90%, at least about 95%, at least about 98%, or at least about 99% sequence identity to the sequence set forth in SEQ ID NO: 2, a human IgG1 heavy chain comprising an amino acid sequence having at least about 90%, at least about 95%, at least about 98%, or at least about 99% sequence identity to the sequence set forth in SEQ ID NO: 39, and a light chain comprising an amino acid sequence having at least about 90%, at least about 95%, at least about 98%, or at least about 99% sequence identity to the sequence set forth in SEQ ID NO: 40. In some embodiments, the agent comprises a heavy chain comprising SEQ ID NO: 2, a human IgG1 heavy chain comprising SEQ ID NO: 39, and a light chain comprising SEQ ID NO: 40.

In another aspect, the present disclosure provides a pharmaceutical composition comprising (i) the agent of described herein and (ii) one or more pharmaceutically acceptable excipient(s).

In another aspect, the present disclosure provides a method of modulating a muscular dystrophy, the method comprising administering the agent described herein to a subject. In some embodiments, the subject is a mammal. In some embodiments, the mammal is a human. In some embodiments, the agent is delivered to a muscle cell or a region adjacent to a muscle cell. In some embodiments, the administering comprises injecting the subject at a location near a skeletal muscle, a muscle satellite cell (e.g., a skeletal muscle satellite cell), a skeletal muscle, a cardiac muscle, a smooth muscle, or a muscle fiber. In some embodiments, the agent induces decreased signaling of the IGF-1 signaling pathway, the GH signaling pathway, the bFGF signaling pathway, the IL4 signaling pathway, or inhibits ActRII. In some embodiments, the muscular dystrophy comprises Duchenne muscular dystrophy (DMD), Becker muscular dystrophy (BMD), a limb-girdle muscular dystrophy (LGMD), and/or a congenital muscular dystrophy.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Various features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5A shows that mice intravenously dosed every 4 days for 14 days with 10 mg/kg of ITGA7-targeted IGF-1 fusion molecule showed an increased percentage of body weight from baseline as compared to naïve mice. FIG. 5B shows anatomical dissection images at the end of this 14-day treatment period, which depicts a qualitative increase in forearm muscle size in ITGA7-targeted IGF-1 fusion molecule treated mice compared to naïve mice. FIG. 5C shows that mice treated with the ITGA7-targeted IGF-1 showed an increase in isolated tibialis anterior (TA) muscle weight of compared to naïve mice. The statistical analysis in FIG. 5A used 2 way ANOVA, n=4-5/group, *****p<0.0001 in time x column factor (naïve vs CAV-003 weight over time). The statistical analysis in FIG. 5C uses unpaired t-test, n=4-5/group, *p<0.05, **p<0.01.

FIG. 6A shows that the mice treated with ITGA7-targeted IGF-1 for 14 days had increased percentage of body weight from baseline as compared to naïve mice. FIG. 6B shows an increase in isolated tibialis anterior (TA) muscle weight of ITGA7-targeted IGF-1 treated mice compared to naïve mice. The statistical analysis in FIG. 6A used 2 way ANOVA, n=4-5/group, *p<0.05 in time x column factor (naïve vs CAV-003 weight over time). The statistical analysis in FIG. 6B uses unpaired t-test, n=8-10/group, *p<0.05, **p<0.01.

FIG. 8A shows that FSHD mice treated every 4 days at 10 mg/kg via intraperitoneal route ITGA7-targeted IGF-1 fusion molecule had increased percentage of body weight from baseline compared to untreated FSHD and wildtype (WT) vehicle-treated mice. FIG. 8B shows a significant increase in isolated gastrocnemius (Gastroc) muscle weight of ITGA7-targeted IGF-1 treated FSHD mice compared to untreated FSHD and wildtype (WT) vehicle-treated mice. FIG. 8C shows a significant increase in max force generation of ITGA7-targeted IGF-1 treated FSHD mice compared to untreated FSHD and wildtype (WT) vehicle-treated mice. The statistical analysis in FIGS. 8A-8C uses one-way ANOVA, Dunnett's multiple comparisons test, n=8-10/group, *p<0.05, p<0.01, p<0.001, ****p<0.0001.

FIG. 9A shows that adult mice (6 months old) dosed with ITGA7-targeted IGF1 fusion molecule every 4 days for 28 days at 10 mg/kg via intraperitoneal route had a significant increase in body weight compared to vehicle (saline) treated animals. FIG. 9B shows the weights of isolated organs (liver, kidney, and heart) and isolated skeletal muscles, including extensor digitorum longus (EDL), tibialis anterior (TA), and gastrocnemius, in treated and untreated mice. Results showed no differences in weights for the isolated organs (liver, kidney, and heart) between treated and vehicle groups, but significant increase in mass of isolated skeletal muscles between treated and vehicle groups. FIG. 9C shows the results of time domain nuclear magnetic resonance used to measure lean mass percentage and fat mass percentage in the treated and untreated mice. Treated mice showed a significant increase from baseline to two weeks and four weeks in lean mass % and in decrease in fat mass %. The statistical analysis in FIGS. 9A-9B uses unpaired t-test. The statistical analysis in FIG. 9C uses one-way ANOVA with multiple comparisons for baseline vs 4 week timepoint, n=8-10/group, *p<0.05

FIG. 11A shows immunofluorescent detection of ITGA7 using 1707-4 (ITGA7 antibody) in WT or ITGA7 KO C2C12 cells. FIG. 11B shows the phosphorylated AKT (P-AKT) levels measured via ELISA method, after WT and ITGA7 KO C2C12 cells were stimulated for 15 minutes with IGF-1. FIG. 11C shows the phosphorylated AKT (P-AKT) levels measured by ELISA method, after WT and ITGA7 KO C2C12 cells were stimulated for 15 minutes with ITGA7-targeted IGF-1 or an IGF-1 variant.

DETAILED DESCRIPTION

Figure 1A:
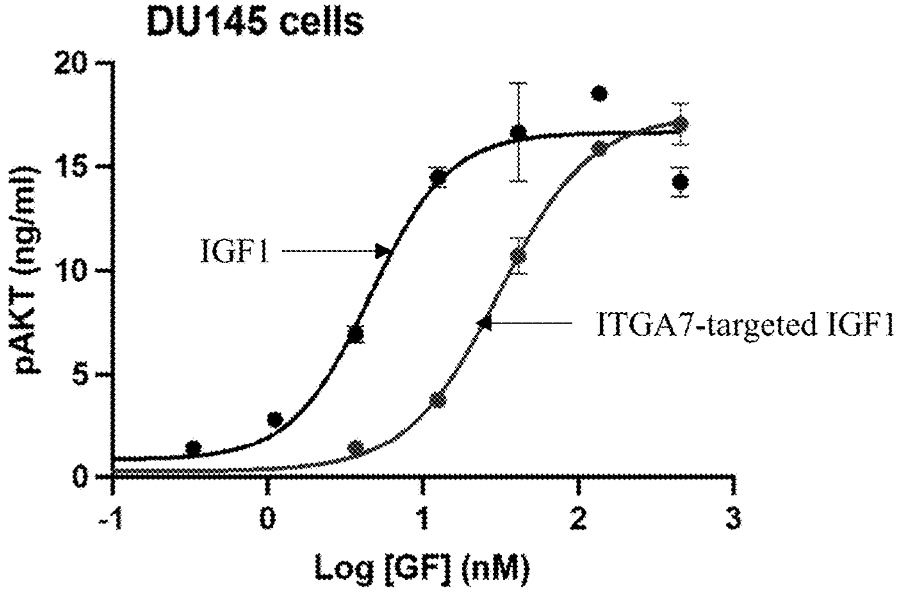
FIG. 1A depicts in vitro potency of ITGA7-targeted IGF-1 in non-muscle cells (DU145) compared to that of IGF-1.

In one aspect, provided herein is an agent that selectively targets a modulator to mammalian cells that express an integrin alpha 7 (ITGA7). In one aspect, the agent comprises (a) a signaling pathway modulator; and (b) an antigen binding domain that selectively binds to a mammalian ITGA7; wherein the modulator is coupled to the antigen-binding domain that selectively binds to the mammalian ITGA7. In some embodiments, the modulator is a transcriptional modulator. The transcriptional modulator may regulate gene expression or gene accessibility. In some embodiments, the transcriptional modulator comprises NF-κB, STAT proteins, p53, DNA methyltransferase, or histone deacetylase. In some embodiments, the modulator is a cell signaling modulator. In some embodiments, the cell signaling modulator comprises a cytokine, a growth factor, or a hormone. In some embodiments, the modulator is a metabolic modulator. The metabolic modulator may regulate metabolic pathway. In some embodiments, the metabolic modulator is an enzyme, a metabolite, or a nutrient. In some embodiments, the modulator is an immune system modulator. The immune system modulator may modulate immune cell activation or suppression or modulate immune response. In some embodiments, the immune system modulator comprises an immune checkpoint inhibitor, an antibody, or an antigen. In some embodiments, the modulator is an ion channel modulator. In some embodiments, the ion channel modulator comprises a calcium modulator, a potassium channel modulator, or a sodium channel modulator. In some embodiments, the modulator is a pharmacological modulator. In some embodiments, the pharmacological modulator comprises a receptor agonist or a receptor antagonist.

In another aspect, provided herein is an agent that selectively targets a signaling pathway modulator to mammalian cells that express an integrin alpha 7 (ITGA7). In one aspect, the agent comprises (a) a signaling pathway modulator; and (b) an antigen binding domain that selectively binds to a mammalian ITGA7; wherein the signaling pathway modulator is coupled to the antigen-binding domain that selectively binds to the mammalian ITGA7.

In one aspect, a signaling pathway modulator modulates an insulin-like growth factor 1 (IGF-1) signaling pathway. The IGF-1 signaling pathway modulator can modulate insulin-like growth factor 1 receptor (IGF-1R), hybrid insulin-like growth factor receptor/Insulin receptor, an insulin-like growth factor binding protein, or a combination thereof. The IGF-1 signaling pathway modulator can comprise an IGF-1 receptor (IGF-1R) or hybrid IGF-1R/IR activator. In certain instances, the IGF-1 signaling pathway modulator comprises an IGF-1 polypeptide. For example, the IGF-1 polypeptide can comprise an IGF-1 polypeptide with a decreased ability to activate the IGF-1 receptor relative to endogenous IGF-1. Decreased activity can be assessed in a functional assay such as those described herein. In some instances, activity of the IGF-1 polypeptide is decreased by at least about 5-fold, 6-fold, 7-fold, 8-fold, 9-fold, 10-fold, 15-fold, 20-fold, or more. In some instances, the IGF-1 polypeptide comprises a variant of IGF-1. An IGF-1 variant can have, for example, an amino acid sequence of any one of SEQ ID NOS: 1-11 and 46-50, or an amino acid sequence that is at least 90%, 95%, 98% or 99% identical to any one of SEQ ID NOS: 1-11 and 46-50 (Table 1). In some instances, the IGF-1 variant comprises about one, about two, about three, about four, or about five amino acid modifications of an amino acid sequence of any one of SEQ ID NOS: 1-11. In some instances, the IGF-1 variant comprises amino acid substitutions in the Fc region of an antibody that are used to reduce its effector functions. In some embodiments, the amino acid substitutions comprise leucine to alanine at positions 234 and 235 in the Fc region of the antibody (LALA). In some embodiments, the amino acid substitutions comprise LALA and additional mutations comprising proline to glycine at another site (LALA-PG).

In another aspect, the IGF-1 polypeptide is a wild-type form of IGF-1. In some embodiments, the wild-type form of IGF-1 comprises an amino acid sequence that is at least 90%, 95%, 98% or 99% identical to SEQ ID NO: 1. In some embodiments, the wild-type form of IGF-1 comprises SEQ ID NO: 1.

TABLE 1

IGF-1 Signaling Modulators

| Name | Target | Fragment | Sequence | SEQ ID NO |
|---|---|---|---|---|
| IGF-1 | IGF1R | 70 aa peptide | GPETLCGAELVDALQFVCGDRGFYFNKPTG YGSSSRRAPQTGIVDECCFRSCDLRRLEMYC APLKPAKSA | 1 |
| IGF-1 | IGF1R | IGF-1-Hole IgG1 N297G | GPETLCGAELVDALQFVCGDRGFYFNKPTG YGSSSRRAPQTGIVDECCFRSCDLRRLEMYC APLKPAKSAGGGGSGGGGSEPKSSDKTHTC PPCPAPELLGGPSVFLFPPKPKDTLMISRTPE VTCVVVDVSHEDPEVKFNWYVDGVEVHNA KTKPREEQYGSTYRVVSVLTVLHQDWLNG KEYKCKVSNKALPAPIEKTISKAKGQPREPQ VCTLPPSRDELTKNQVSLSCAVKGFYPSDIA VEWESNGQPENNYKTTPPVLDSDGSFFLVSK LTVDKSRWQQGNVFSCSVMHEALHNHYTQ KSLSLSPGK | 2 |
| IGF-1 | IGF1R | IGF-1-Hole of 1790.3 | GPETLCGAELVDALQFVCGDRGFYFNKPTG YGSSSRAPQTGIVDECCFRSCDLRRLEMYCA PLKPAKSAGGGGSGGGGSEPKSSDKTHTCPP CPAPELLGGPSVFLFPPKPKDTLMISRTPEVT CVVVDVSHEDPEVKFNWYVDGVEVHNAKT KPREEQYGSTYRVVSVLTVLHQDWLNGKE YKCKVSNKALPAPIEKTISKAKGQPREPQVC | 46 |

TABLE 1-continued

| IGF-1 Signaling Modulators | | | | |
|---|---|---|---|---|
| Name | Target | Fragment | Sequence | SEQ ID NO |
| | | | TLPPSRDELTKNQVSLSCAVKGFYPSDIAVE WESNGQPENNYKTTPPVLDSDGSFFLVSKLT VDKSRWQQGNVFSCSVMHEALHNHYTQKS LSLSPGK | |
| IGF-1 | IGF1R | IGF-1-Hole of 1790.4 | GPETLCGAELVDALQFVCGDRGFLFNKPTG YGSSSRRAPQTGIVDECCFRSCDLRRLEMYC APLKPAKSAGGGGSGGGGSEPKSSDKTHTC PPCPAPELLGGPSVFLFPPKPKDTLMISRTPE VTCVVVDVSHEDPEVKFNWYVDGVEVHNA KTKPREEQYGSTYRVVSVLTVLHQDWLNG KEYKCKVSNKALPAPIEKTISKAKGQPREPQ VCTLPPSRDELTKNQVSLSCAVKGFYPSDIA VEWESNGQPENNYKTTPPVLDSDGSFFLVSK LTVDKSRWQQGNVFSCSVMHEALHNHYTQ KSLSLSPGK | 47 |
| IGF-1 | IGF1R | IGF-1-Hole of 1790.5 | GPETLCGAELVDALQFVCGDRGFYFNKPTG AGSSSRRAPQTGIVDECCFRSCDLRRLEMYC APLKPAKSAGGGGSGGGGSEPKSSDKTHTC PPCPAPELLGGPSVFLFPPKPKDTLMISRTPE VTCVVVDVSHEDPEVKFNWYVDGVEVHNA KTKPREEQYGSTYRVVSVLTVLHQDWLNG KEYKCKVSNKALPAPIEKTISKAKGQPREPQ VCTLPPSRDELTKNQVSLSCAVKGFYPSDIA VEWESNGQPENNYKTTPPVLDSDGSFFLVSK LTVDKSRWQQGNVFSCSVMHEALHNHYTQ KSLSLSPGK | 48 |
| IGF-1 | IGF1R | IGF-1-Hole of 1790.6 | GPETLCGAELVDALQFVCGDRGFYFNKPTG YGSSSRAPQTGIVDECCFRSCDLRRLEMYCA PLKPAKSAGGGGSGGGGSEPKSSDKTHTCPP CPAPELLGGPSVFLFPPKPKDTLMISRTPEVT CVVVDVSHEDPEVKFNWYVDGVEVHNAKT KPREEQYGSTYRVVSVLTVLHQDWLNGKE YKCKVSNKALPAPIEKTISKAKGQPREPQVC TLPPSRDELTKNQVSLSCAVKGFYPSDIAVE WESNGQPENNYKTTPPVLDSDGSFFLVSKLT VDKSRWQQGNVFSCSVMHEALHNHYTQKS LSLSPGK | 49 |
| IGF-1 | IGF1R | IGF-1-Hole of 1790.7 | GPETLCGAELVDALQFVCGDRGFLFNKPTG YGSSSRRAPQTGIVDECCFRSCDLRRLEMYC APLKPAKSAGGGGSGGGGSEPKSSDKTHTC PPCPAPELLGGPSVFLFPPKPKDTLMISRTPE VTCVVVDVSHEDPEVKFNWYVDGVEVHNA KTKPREEQYGSTYRVVSVLTVLHQDWLNG KEYKCKVSNKALPAPIEKTISKAKGQPREPQ VCTLPPSRDELTKNQVSLSCAVKGFYPSDIA VEWESNGQPENNYKTTPPVLDSDGSFFLVSK LTVDKSRWQQGNVFSCSVMHEALHNHYTQ KSLSLSPGK | 50 |
| IGF1-Ea | IGF1R | IGF1Ea peptide | GPETLCGAELVDALQFVCGDRGFYFNKPTG YGSSSRRAPQTGIVDECCFRSCDLRRLEMYC APLKPAKSARSVRAQRHTDMPKTQKEVHLK NASRGSAGNKNYRM | 3 |
| IGF1-Eb | IGF1R | IGF1Eb peptide | GPETLCGAELVDALQFVCGDRGFYFNKPTG YGSSSRRAPQTGIVDECCFRSCDLRRLEMYC APLKPAKSARSVRAQRHTDMPKTQKYQPPS TNKNTKSQRRKGWPKTHPGGEQKEGTEASL QIRGKKKEQRREIGSRNAECRGKKGK | 4 |
| IGF1-Ec | IGF1R | IGF1Ec peptide | GPETLCGAELVDALQFVCGDRGFYFNKPTG YGSSSRRAPQTGIVDECCFRSCDLRRLEMYC APLKPAKSARSVRAQRHTDMPKTQKYQPPS TNKNTKSQRRKGSTFEERK | 5 |
| IGF1-R37x | IGF1R | IGF1 R37x | GPETLCGAELVDALQFVCGDRGFYFNKPTG YGSSSRAPQTGIVDECCFRSCDLRRLEMYCA PLKPAKSA | 6 |

TABLE 1-continued

| IGF-1 Signaling Modulators | | | | |
|---|---|---|---|---|
| Name | Target | Fragment | Sequence | SEQ ID NO |
| IGF1-Ea R37x | IGF1R | IGF1Ea peptide | GPETLCGAELVDALQFVCGDRGFYFNKPTG YGSSSRAPQTGIVDECCFRSCDLRRLEMLCA PLKPAKSARSVRAQRHTDMPKTQKEVHLKN ASRGSAGNKNYRM | 7 |
| IGF1-Eb R37x | IGF1R | IGF1Eb peptide | GPETLCGAELVDALQFVCGDRGFYFNKPTG YGSSSRAPQTGIVDECCFRSCDLRRLEMYCA PLKPAKSARSVRAQRHTDMPKTQKYQPPST NKNTKSQRRKGWPKTHPGGEQKEGTEASLQ IRGKKKEQRREIGSRNAECRGKKGK | 8 |
| IGF1-Ec R37x | IGF1R | IGF1Ec peptide | GPETLCGAELVDALQFVCGDRGFYFNKPTG YGSSSRAPQTGIVDECCFRSCDLRRLEMYCA PLKPAKSARSVRAQRHTDMPKTQKYQPPST NKNTKSQRRKGSTFEERK | 9 |
| Des 1-3 IGF1 | IGF1R | Des 1-3 IGF1 | TLCGAELVDALQFVCGDRGFYFNKPTGYGS SSRRAPQTGIVDECCFRSCDLRRLEMYCAPL KPAKSA | 10 |
| IGF1 E3R | IGF1R | IGF1 E3R | GPRTLCGAELVDALQFVCGDRGFYFNKPTG YGSSSRRAPQTGIVDECCFRSCDLRRLEMYC APLKPAKSA | 11 |

In another aspect, a signaling pathway modulator modulates a growth hormone (GH) signaling pathway. The GH signaling pathway modulator can modulate a growth hormone receptor (GHIR). The GH signaling pathway modulator can comprise a GHIR activator. In certain instances, the GH signaling pathway modulator comprises an GH polypeptide. For example, the GH polypeptide can comprise an GH polypeptide with a decreased ability to activate the GHIR relative to endogenous GH. Decreased activity can be assessed in a functional assay such as those described herein. In some instances, the GH polypeptide comprises a variant of GH. An GH variant can have, for example, an amino acid sequence of SEQ ID NO: 12 or 13, or an amino acid sequence that is at least 90%, 95%, 98% or 99% identical to SEQ ID NO: 12 or 13 (Table 2). In some instances, an GH variant comprises about one, about two, about three, about four, or about five amino acid modifications of an amino acid sequence of SEQ ID NO: 12 or 13.

In another aspect, a signaling pathway modulator modulates a basic fibroblast growth factor (bFGF) signaling pathway. The bFGF signaling pathway modulator can modulate a fibroblast growth factor receptor (FGFR). The bFGF signaling pathway modulator can comprise a FGFR activator. In certain instances, the bFGF signaling pathway modulator comprises an bFGF polypeptide. For example, the bFGF polypeptide can comprise an bFGF polypeptide with a decreased ability to activate the FGFR relative to endogenous bFGF. Decreased activity can be assessed in a functional assay such as those described herein. In some instances, the bFGF polypeptide comprises a variant of bFGF. An bFGF variant can have, for example, an amino acid sequence any one of SEQ ID NOS: 14-17, or an amino acid sequence that is at least 90%, 95%, 98% or 99% identical to any one of SEQ ID NOS: 14-17 (Table 2). In some instances, an bFGF variant comprises about one, about two, about three, about four, or about five amino acid modifications of an amino acid sequence of any one of SEQ ID NOS: 14-17.

In another aspect, a signaling pathway modulator modulates an interleukin 4 (IL4) signaling pathway. The IL4 signaling pathway modulator can modulate an interleukin 4 receptor (IL4R). The IL4 signaling pathway modulator can comprise a IL4R activator. In certain instances, the IL4 signaling pathway modulator comprises an IL4 polypeptide. For example, the IL4 polypeptide can comprise an IL4 polypeptide with a decreased ability to activate the IL4R relative to endogenous IL4. Decreased activity can be assessed in a functional assay such as those described herein. In some instances, the IL4 polypeptide comprises a variant of IL4. An IL4 variant can have, for example, an amino acid sequence any one of SEQ ID NOS: 18-21, or an amino acid sequence that is at least 90%, 95%, 98% or 99% identical to any one of SEQ ID NOS: 18-21 (Table 2). In some instances, an IL4 variant comprises about one, about two, about three, about four, or about five amino acid modifications of an amino acid sequence of any one of SEQ ID NOS: 18-21.

In another aspect, a signaling pathway modulator modulates an activin type II receptor (ActRII). The signaling pathway modulator can comprise an ActRII inhibitor. In certain instances, the signaling pathway modulator comprises bimagrumab. In some instances, the antibody or antibody fragment comprises a variable heavy chain complementarity determining region 1 (VH CDR1) comprising an amino acid sequence having at least about 70%, at least about 80%, at least about 90%, at least about 95%, or 100% sequence identity to the sequence set forth in SEQ ID NO: 22, a VH CDR2 comprising an amino acid sequence having at least about 70%, at least about 80%, at least about 90%, at least about 95%, or 100% sequence identity to the sequence set forth in SEQ ID NO: 23, and a VH CDR3 comprising an amino acid sequence having at least about 70%, at least about 80%, at least about 90%, at least about 95%, or 100% sequence identity to the sequence set forth in SEQ ID NO: 24. In some instances, the antibody or antibody fragment comprises a VH CDR1 comprising an amino acid sequence having about one, about two, about three, about four, or about five amino acid modifications of the sequence set forth in SEQ ID NO: 22, a VH CDR2 comprising an amino acid sequence having about one, about two, about three, about four, or about five amino acid modifications of the sequence set forth in SEQ ID NO: 23, and a VH CDR3 comprising an amino acid sequence having about one, about two, about three, about four, or about five amino acid modifications of the sequence set forth in SEQ ID NO: 24. In some instances, the antibody or antibody fragment comprises a variable light chain complementarity determining region 1 (VL CDR1) comprising an amino acid sequence having at least about 70%, at least about 80%, at least about 90%, at least about 95%, or 100% sequence identity to the sequence set forth in SEQ ID NO: 25, a VL CDR2 comprising an amino acid sequence having at least about 70%, at least about 80%, at least about 90%, at least about 95%, or 100% sequence identity to the sequence set forth in SEQ ID NO: 26, and a VL CDR3 comprising an amino acid sequence having at least about 70%, at least about 80%, at least about 90%, at least about 95%, or 100% sequence identity to the sequence set forth in SEQ ID NO: 27. In some instances, the antibody or antibody fragment comprises a VL CDR1 comprising an amino acid sequence having about one, about two, about three, about four, or about five amino acid modifications of the sequence set forth in SEQ ID NO: 25, a VL CDR2 comprising an amino acid sequence having about one, about two, about three, about four, or about five amino acid modifications of the sequence set forth in SEQ ID NO: 26, and a VL CDR3 comprising an amino acid sequence having about one, about two, about three, about four, or about five amino acid modifications of the sequence set forth in SEQ ID NO: 27. In some instances, the antibody or antibody fragment comprises a variable heavy (VH) chain comprising an amino acid sequence having at least about 90%, at least about 95%, at least about 98%, at least about 99%, or 100% sequence identity to the sequence set forth in SEQ ID NO: 28. In some instances, the antibody or antibody fragment comprises a VH chain comprising an amino acid sequence having about one, about two, about three, about four, or about five amino acid modifications of the sequence set forth in SEQ ID NO: 28. In some instances, the antibody or antibody fragment comprises a variable light (VL) chain comprising an amino acid sequence having at least about 90%, at least about 95%, at least about 98%, at least about 99%, or 100% sequence identity to the sequence set forth in SEQ ID NO: 29. In some instances, the antibody or antibody fragment comprises a VL chain comprising an amino acid sequence having about one, about two, about three, about four, or about five amino acid modifications of the sequence set forth in SEQ ID NO: 29. In some instances, the antibody or antibody fragment comprises an amino acid sequence of SEQ ID NO: 30, or an amino acid sequence having at least about 90%, at least about 95%, at least about 98%, or at least about 99% sequence identity to the sequence set forth in SEQ ID NO: 30 (Table 2). In some instances, the antibody or antibody fragment comprises about one, about two, about three, about four, or about five amino acid modifications of an amino acid sequence set forth in SEQ ID NO: 30.

TABLE 2

Other Signaling Modulators

| Name | Target | Fragment | Sequence | SEQ ID NO |
|---|---|---|---|---|
| GH | GHR | Cargo Polypeptide | FPTIPLSRLFDNAMLRAHRLHQLA FDTYQEFEEAYIPKEQKYSFLQNP QTSLCFSESIPTPSNREETQQKSNL ELLRISLLLIQSWLEPVQFLRSVFA NSLVYGASDSNVYDLLKDLEEGI QTLMGRLEDGSPRTGQIFKQTYS KFDTNSHNDDALLKNYGLLYCFR KDMDKVETFLRIVQCRSVEGSCG F | 12 |
| GH | GHR | GH-Hole Heavy Chain | FPTIPLSRLFDNAMLRAHRLHQLA FDTYQEFEEAYIPKEQKYSFLQNP QTSLCFSESIPTPSNREETQQKSNL ELLRISLLLIQSWLEPVQFLRSVFA NSLVYGASDSNVYDLLKDLEEGI QTLMGRLEDGSPRTGQIFKQTYS KFDTNSHNDDALLKNYGLLYCFR KDMDKVETFLRIVQCRSVEGSCG FGGGGSGGGGSEPKSSDKTHTCP PCPAPELLGGPSVFLFPPKPKDTL MISRTPEVTCVVVDVSHEDPEVK FNWYVDGVEVHNAKTKPREEQY GSTYRVVSVLTVLHQDWLNGKE YKCKVSNKALPAPIEKTISKAKGQ PREPQVCTLPPSRDELTKNQVSLS CAVKGFYPSDIAVEWESNGQPEN NYKTTPPVLDSDGSFFLVSKLTVD KSRWQQGNVFSCSVMHEALHNH YTQKSLSLSPGK | 13 |
| bFGF | FGFR | Cargo Polypeptide-1 | PALPEDGGSGAFPPGHFKDPKRL YCKNGGFFLRIHPDGRVDGVREK SDPHIKLQLQAEERGVVSIKGVCA NRYLAMKEDGRLLASKCVTDECF FFERLESNNYNTYRSRKYTSWYV ALKRTGQYKLGSKTGPGQKAILF LPMSAKS | 14 |

TABLE 2-continued

| Other Signaling Modulators | | | | |
|---|---|---|---|---|
| Name | Target | Fragment | Sequence | SEQ ID NO |
| bFGF | FGFR | bFGF Hole Heavy Chain-1 | PALPEDGGSGAFPPGHFKDPKRL YCKNGGFFLRIHPDGRVDGVREK SDPHIKLQLQAEERGVVSIKGVCA NRYLAMKEDGRLLASKCVTDECF FFERLESNNYNTYRSRKYTSWYV ALKRTGQYKLGSKTGPGQKAILF LPMSAKSGGGGSGGGGSEPKSSD KTHTCPPCPAPELLGGPSVFLFPP KPKDTLMISRTPEVTCVVVDVSH EDPEVKFNWYVDGVEVHNAKTK PREEQYGSTYRVVSVLTVLHQDW LNGKEYKCKVSNKALPAPIEKTIS KAKGQPREPQVCTLPPSRDELTK NQVSLSCAVKGFYPSDIAVEWES NGQPENNYKTTPPVLDSDGSFFL VSKLTVDKSRWQQGNVFSCSVM HEALHNHYTQKSLSLSPGK | 15 |
| bFGF | FGFR | Cargo Polypeptide-2 | PALPEDGGSGAFPPGHFKDPKRL YCKNGGFFLRIHPDGRVDGVREK SDPHIKLQLQAEERGVVSIKGVCA NRYLAMKEDGRLLASKCVTDECF FFERLESNNYNTYRSRKYTSWYV ALKRTGQYKLGSKTGPGQKAILF LPMSAKS | 16 |
| bFGF | FGFR | bFGF Hole Heavy Chain-2 | GSCPPCPAPELLGGPSVFLFPPKPK DTLMISRTPEVTCVVVDVSHEDPE VKFNWYVDGVEVHNAKTKPREE QYGSTYRVVSVLTVLHQDWLNG KEYKCKVSNKALPAPIEKTISKAK GQPREPQVCTLPPSRDELTKNQVS LSCAVKGFYPSDIAVEWESNGQP ENNYKTTPPVLDSDGSFFLVSKLT VDKSRWQQGNVFSCSVMHEALH NHYTQKSLSLSPGGGGGSGGGGS PALPEDGGSGAFPPGHFKDPKRL YCKNGGFFLRIHPDGRVDGVREK SDPHIKLQLQAEERGVVSIKGVCA NRYLAMKEDGRLLASKCVTDECF FFERLESNNYNTYRSRKYTSWYV ALKRTGQYKLGSKTGPGQKAILF LPMSAKS | 17 |
| IL4 | IL4R | Cargo Polypeptide-1 | HKCDITLQEIIKTLNSLTEQKTLCT ELTVTDIFAASKNTTEKETFCRAA TVLRQFYSHHEKDTRCLGATAQQ FHRHKQLIRFLKRLDRNLWGLAG LNSCPVKEANQSTLENFLERLKTI MREKYSKCSS | 18 |
| IL4 | IL4R | IL4 Hole Heavy Chain-1 | HKCDITLQEIIKTLNSLTEQKTLCT ELTVTDIFAASKNTTEKETFCRAA TVLRQFYSHHEKDTRCLGATAQQ FHRHKQLIRFLKRLDRNLWGLAG LNSCPVKEANQSTLENFLERLKTI MREKYSKCSSGGGGSGGGGSEPK SSDKTHTCPPCPAPELLGGPSVFL FPPKPKDTLMISRTPEVTCVVVDV SHEDPEVKFNWYVDGVEVHNAK TKPREEQYGSTYRVVSVLTVLHQ DWLNGKEYKCKVSNKALPAPIEK TISKAKGQPREPQVCTLPPSRDEL TKNQVSLSCAVKGFYPSDIAVEW ESNGQPENNYKTTPPVLDSDGSFF LVSKLTVDKSRWQQGNVFSCSV MHEALHNHYTQKSLSLSPGK | 19 |
| IL4 | IL4R | Cargo Polypeptide-2 | HKCDITLQEIIKTLNSLTEQKTLCT ELTVTDIFAASKNTTEKETFCRAA TVLRQFYSHHEKDTRCLGATAQQ FHRHKQLIRFLKRLDRNLWGLAG LNSCPVKEANQSTLENFLERLKTI MREKYSKCSS | 20 |

TABLE 2-continued

Other Signaling Modulators

| Name | Target | Fragment | Sequence | SEQ ID NO |
|---|---|---|---|---|
| IL4 | IL4R | IL4 Hole Heavy Chain-2 | GSCPPCPAPELLGGPSVFLFPPKPK DTLMISRTPEVTCVVVDVSHEDPE VKFNWYVDGVEVHNAKTKPREE QYGSTYRVVSVLTVLHQDWLNG KEYKCKVSNKALPAPIEKTISKAK GQPREPQVCTLPPSRDELTKNQVS LSCAVKGFYPSDIAVEWESNGQP ENNYKTTPPVLDSDGSFFLVSKLT VDKSRWQQGNVFSCSVMHEALH NHYTQKSLSLSPGGGGGSGGGGS HKCDITLQEIIKTLNSLTEQKTLCT ELTVTDIFAASKNTTEKETFCRAA TVLRQFYSHHEKDTRCLGATAQQ FHRHKQLIRFLKRLDRNLWGLAG LNSCPVKEANQSTLENFLERLKTI MREKYSKCSS | 21 |
| bimagrumab | ActRII | VH CDR1 | GYTFTSSY | 22 |
| | | VH CDR2 | INPVSGST | 23 |
| | | VH CDR3 | GGWFDY | 24 |
| bimagrumab | ActRII | VL CDR1 | SSDVGSYNY | 25 |
| | | VL CDR2 | GVSK | 26 |
| | | VL CDR3 | GTFAGGSYYGV | 27 |
| bimagrumab | ActRII | VH | QVQLVQSGAEVKKPGASVKVSC KASGYTFTSSYINWVRQAPGQGL EWMGTINPVSGSTSYAQKFQGRV TMTRDTSISTAYMELSRLRSDDTA VYYCARGGWFDYWGQGTLVTVS S | 28 |
| bimagrumab | ActRII | VL | QSALTQPASVSGSPGQSITISCTGT SSDVGSYNYVNWYQQHPGKAPK LMIYGVSKRPSGVSNRFSGSKSGN TASLTISGLQAEDEADYYCGTFA GGSYYGVFGGGTKLTVL | 29 |
| bimagrumab | ActRII | bimagrumab-Hole Heavy Chain | DIVMTQGALPNPVPSGESVSITCR SSKSLLYSDGKTYLNWYLQRPGQ SPQLLIYWMSTRASGVSDRFSGSG SGTDFTLKISGVEAEDVGVYYCQ QGLEFPDTFGAGTKLELKGGGGS GGGGSGGGGSQVQLVQSGAEVK KPGASVKVSCKASGYTFTSSYIN WVRQAPGQGLEWMGTINPVSGS TSYAQKFQGRVTMTRDTSISTAY MELSRLRSDDTAVYYCARGGWF DYWGQGTLVTVSSASTKGPSVFP LAPSSKSTSGGTAALGCLVKDYFP EPVTVSWNSGALTSGVHTFPAVL QSSGLYSLSSVVTVPSSSLGTQTYI CNVNHKPSNTKVDKKVEPKSCD KTHTCPPCPAPELLGGPSVFLFPP KPKDTLMISRTPEVTCVVVDVSH EDPEVKFNWYVDGVEVHNAKTK PREEQYGSTYRVVSVLTVLHQDW LNGKEYKCKVSNKALPAPIEKTIS KAKGQPREPQVCTLPPSRDELTK NQVSLSCAVKGFYPSDIAVEWES NGQPENNYKTTPPVLDSDGSFFL VSKLTVDKSRWQQGNVFSCSVM HEALHNHYTQKSLSLSPGK | 30 |
| bimagrumab | ActRII | Cargo Polypeptide | DIVMTQGALPNPVPSGESVSITCR SSKSLLYSDGKTYLNWYLQRPGQ SPQLLIYWMSTRASGVSDRFSGSG SGTDFTLKISGVEAEDVGVYYCQ QGLEFPDTFGAGTKLELKGGGGS GGGGSGGGGSQVQLVQSGAEVK KPGASVKVSCKASGYTFTSSYIN WVRQAPGQGLEWMGTINPVSGS TSYAQKFQGRVTMTRDTSISTAY MEELSRLRSDDTAVYYCARGGWF DYWGQGTLVTVSSASTKGPSVFP | 44 |

TABLE 2-continued

| Other Signaling Modulators | | | | |
|---|---|---|---|---|
| Name | Target | Fragment | Sequence | SEQ ID NO |
| | | | LAPSSKSTSGGTAALGCLVKDYFP EPVTVSWNSGALTSGVHTFPAVL QSSGLYSLSSVVTVPSSSLGTQTYI CNVNHKPSNTKVDKKVEPKSCD KTHT | |

In one aspect, the antigen binding domain binds to an epitope expressed in muscle tissue. In some instances, the antigen binding domain binds to an epitope expressed in a muscle cell. In some instances, the antigen binding domain binds to an epitope expressed in a mammalian muscle satellite cell. In some instances, the antigen binding domain binds to an epitope expressed in a mammalian skeletal muscle cell. In some instances, the antigen binding domain binds to an epitope expressed in a mammalian cardiac muscle cell. In some instances, the antigen binding domain binds to an epitope expressed in a mammalian muscle fiber.

The antigen binding domain can be, for example, an antibody or an antigen binding fragment. When the targeting moiety is the antigen binding fragment, the antigen binding fragment can be, for example, a fragment antigen-binding (Fab) domain or a single chain variable fragment (scFv). In some instances, the antigen binding domain comprises a VH complementarity determining region 1 (VH CDR1) comprising an amino acid sequence having at least about 70%, at least about 80%, at least about 90%, at least about 95%, or 100% sequence identity to the sequence set forth in SEQ ID NO: 31, a VH CDR2 comprising an amino acid sequence having at least about 70%, at least about 80%, at least about 90%, at least about 95%, or 100% sequence identity to the sequence set forth in SEQ ID NO: 32, and a VH CDR3 comprising an amino acid sequence having at least about 70%, at least about 80%, at least about 90%, at least about 95%, or 100% sequence identity to the sequence set forth in SEQ ID NO: 33. In some instances, the antigen binding domain comprises a VH CDR1 comprising an amino acid sequence having about one, about two, about three, about four, or about five amino acid modifications of the sequence set forth in SEQ ID NO: 31, a VH CDR2 comprising an amino acid sequence having about one, about two, about three, about four, or about five amino acid modifications of the sequence set forth in SEQ ID NO: 32, and a VH CDR3 comprising an amino acid sequence having about one, about two, about three, about four, or about five amino acid modifications of the sequence set forth in SEQ ID NO: 33.

In some instances, the antigen binding domain comprises a VL CDR1 comprising an amino acid sequence having at least about 70%, at least about 80%, at least about 90%, at least about 95%, or 100% sequence identity to the sequence set forth in SEQ ID NO: 34, a VL CDR2 comprising an amino acid sequence having at least about 70%, at least about 80%, at least about 90%, at least about 95%, or 100% sequence identity to the sequence set forth in SEQ ID NO: 35, and a VL CDR3 comprising an amino acid sequence having at least about 70%, at least about 80%, at least about 90%, at least about 95%, or 100% sequence identity to the sequence set forth in SEQ ID NO: 36. In some instances, the antigen binding domain comprises a VL CDR1 comprising an amino acid sequence having about one, about two, about three, about four, or about five amino acid modifications of the sequence set forth in SEQ ID NO: 34, a VL CDR2 comprising an amino acid sequence having about one, about two, about three, about four, or about five amino acid modifications of the sequence set forth in SEQ ID NO: 35, and a VL CDR3 comprising an amino acid sequence having about one, about two, about three, about four, or about five amino acid modifications of the sequence set forth in SEQ ID NO: 36. In some instances, the antigen binding domain comprises a variable light (VL) chain comprising an amino acid sequence having at least about 90%, at least about 95%, at least about 98%, at least about 99%, or 100% sequence identity to the sequence set forth in SEQ ID NO: 38, and a variable heavy (VH) chain knob comprising an amino acid sequence having at least about 90%, at least about 95%, at least about 98%, at least about 99%, or 100% sequence identity to the sequence set forth in SEQ ID NO: 37. In some instances, the antigen binding domain comprises a variable light (VL) chain comprising an amino acid sequence having about one, about two, about three, about four, or about five amino acid modifications of the sequence set forth in SEQ ID NO: 38, and a variable heavy (VH) chain knob comprising an amino acid sequence having about one, about two, about three, about four, or about five amino acid modifications of the sequence set forth in SEQ ID NO: 37 (Table 3).

TABLE 3

| Antigen Binding Domain | | | | |
|---|---|---|---|---|
| Name | Target | Fragment | Sequence | SEQ ID NO |
| Anti-ITGA7 | ITGA7 | VH CDR1 | GFTFSNYD | 31 |
| | | VH CDR2 | ISYDGSRN | 32 |
| | | VH CDR3 | TTADNYWFAY | 33 |
| Anti-ITGA7 | ITGA7 | VL CDR1 | KSLLYSDGKTY | 34 |
| | | VL CDR2 | WMS | 35 |
| | | VL CDR3 | CQQGLEFPDT | 36 |
| Anti-ITGA7 | ITGA7 | VH | EVQLVESGGGLVQPGRSMKVS CAASGFTFSNYDMAWVRQAPT | 37 |

TABLE 3-continued

| Antigen Binding Domain | | | | |
|---|---|---|---|---|
| Name | Target | Fragment | Sequence | SEQ ID NO |
| | | | KGLEWVASISYDGSRNYYRDSV KGRFTISRDNAKSTLYLQMDSL RSEDTATYYCTTADNYWFAYW GQGTLVTVSS | |
| Anti-ITGA7 | ITGA7 | VL | DIVMTQGALPNPVPSGESVSITC RSSKSLLYSDGKTYLNWYLQRP GQSPQILIYWMSTRASGVSDRFS GSGSGTDFTLKISGVEAEDVGV YYCQQGLEFPDTFGAGTKLELK | 38 |
| Anti-ITGA7 | ITGA7 | Heavy chain: Knob | EVQLVESGGGLVQPGRSMKVS CAASGFTFSNYDMAWVRQAPT KGLEWVASISYDGSRNYYRDSV KGRFTISRDNAKSTLYLQMDSL RSEDTATYYCTTADNYWFAYW GQGTLVTVSSASTKGPSVFPLAP SSKSTSGGTAALGCLVKDYFPE PVTVSWNSGALTSGVHTFPAVL QSSGLYSLSSVVTVPSSSLGTQT YICNVNHKPSNTKVDKKVEPKS CDKTHTCPPCPAPELLGGPSVFL FPPKPKDTLMISRTPEVTCVVVD VSHEDPEVKFNWYVDGVEVHN AKTKPREEQYGSTYRVVSVLTV LHQDWLNGKEYKCKVSNKALP APIEKTISKAKGQPREPQVYTLP PCRDELTKNQVSLWCLVKGFYP SDIAVEWESNGQPENNYKTTPP VLDSDGSFFLYSKLTVDKSRWQ QGNVFSCSVMHEALHNHYTQK SLSLSPGK | 39 |
| Anti-ITGA7 | ITGA7 | Light chain | DIVMTQGALPNPVPSGESVSITC RSSKSLLYSDGKTYLNWYLQRP GQSPQLLIYWMSTRASGVSDRF SGSGSGTDFTLKISGVEAEDVG VYYCQQGLEFPDTFGAGTKLEL KRTVAAPSVFIFPPSDEQLKSGT ASVVCLLNNFYPREAKVQWKV DNALQSGNSQESVTEQDSKDST YSLSSTLTLSKADYEKHKVYAC EVTHQGLSSPVTKSFNRGEC | 40 |
| Anti-ITGA7 | ITGA7 | Heavy chain: Knob of 1790.3 | EVQLVESGGGLVQPGRSMKVS CAASGFTFSNYDMAWVRQAPT KGLEWVASISYDGSRNYYRDSV KGRFTISRDNAKSTLYLQMDSL RSEDTATYYCTTADNYWFAYW GQGTLVTVSSASTKGPSVFPLAP SSKSTSGGTAALGCLVKDYFPE PVTVSWNSGALTSGVHTFPAVL QSSGLYSLSSVVTVPSSSLGTQT YICNVNHKPSNTKVDKKVEPKS CDKTHTCPPCPAPELLGGPSVFL FPPKPKDTLMISRTPEVTCVVVD VSHEDPEVKFNWYVDGVEVHN AKTKPREEQYGSTYRVVSVLTV LHQDWLNGKEYKCKVSNKALP APIEKTISKAKGQPREPQVYTLP PCRDELTKNQVSLWCLVKGFYP SDIAVEWESNGQPENNYKTTPP VLDSDGSFFLYSKLTVDKSRWQ QGNVFSCSVMHEALHNHYTQK SLSLSPGK | 51 |
| Anti-ITGA7 | ITGA7 | Light chain of 1790.3 | DIVMTQGALPNPVPSGESVSITC RSSKSLLYSDGKTYLNWYLQRP GQSPQLLIYWMSTRASGVSDRF SGSGSGTDFTLKISGVEAEDVG VYYCQQGLEFPDTFGAGTKLEL KRTVAAPSVFIFPPSDEQLKSGT | 52 |

TABLE 3-continued

| Antigen Binding Domain | | | | |
|---|---|---|---|---|
| Name | Target | Fragment | Sequence | SEQ ID NO |
| | | | ASVVCLLNNFYPREAKVQWKV DNALQSGNSQESVTEQDSKDST YSLSSTLTLSKADYEKHKVYAC EVTHQGLSSPVTKSFNRGEC | |
| Anti-ITGA7 | ITGA7 | Heavy chain: Knob of 1790.4 | EVQLVESGGGLVQPGRSMKVS CAASGFTFSNYDMAWVRQAPT KGLEWVASISYDGSRNYYRDSV KGRFTISRDNAKSTLYLQMDSL RSEDTATYYCTTADNYWFAYW GQGTLVTVSSASTKGPSVFPLAP SSKSTSGGTAALGCLVKDYFPE PVTVSWNSGALTSGVHTFPAVL QSSGLYSLSSVVTVPSSSLGTQT YICNVNHKPSNTKVDKKVEPKS CDKTHTCPPCPAPELLGGPSVFL FPPKPKDTLMISRTPEVTCVVVD VSHEDPEVKFNWYVDGVEVHN AKTKPREEQYGSTYRVVSVLTV LHQDWLNGKEYKCKVSNKALP APIEKTISKAKGQPREPQVYTLP PCRDELTKNQVSLWCLVKGFYP SDIAVEWESNGQPENNYKTTPP VLDSDGSFFLYSKLTVDKSRWQ QGNVFSCSVMHEALHNHYTQK SLSLSPGK | 53 |
| Anti-ITGA7 | ITGA7 | Light chain of 1790.4 | DIVMTQGALPNPVPSGESVSITC RSSKSLLYSDGKTYLNWYLQRP GQSPQLLIYWMSTRASGVSDRF SGSGSGTDFTLKISGVEAEDVG VYYCQQGLEFPDTFGAGTKLEL KRTVAAPSVFIFPPSDEQLKSGT ASVVCLLNNFYPREAKVQWKV DNALQSGNSQESVTEQDSKDST YSLSSTLTLSKADYEKHKVYAC EVTHQGLSSPVTKSFNRGEC | 54 |
| Anti-ITGA7 | ITGA7 | Heavy chain: Knob of 1790.5 | EVQLVESGGGLVQPGRSMKVS CAASGFTFSNYDMAWVRQAPT KGLEWVASISYDGSRNYYRDSV KGRFTISRDNAKSTLYLQMDSL RSEDTATYYCTTADNYWFAYW GQGTLVTVSSASTKGPSVFPLAP SSKSTSGGTAALGCLVKDYFPE PVTVSWNSGALTSGVHTFPAVL QSSGLYSLSSVVTVPSSSLGTQT YICNVNHKPSNTKVDKKVEPKS CDKTHTCPPCPAPELLGGPSVFL FPPKPKDTLMISRTPEVTCVVVD VSHEDPEVKFNWYVDGVEVHN AKTKPREEQYGSTYRVVSVLTV LHQDWLNGKEYKCKVSNKALP APIEKTISKAKGQPREPQVYTLP PCRDELTKNQVSLWCLVKGFYP SDIAVEWESNGQPENNYKTTPP VLDSDGSFFLYSKLTVDKSRWQ QGNVFSCSVMHEALHNHYTQK SLSLSPGK | 55 |
| Anti-ITGA7 | ITGA7 | Light chain of 1790.5 | DIVMTQGALPNPVPSGESVSITC RSSKSLLYSDGKTYLNWYLQRP GQSPQLLIYWMSTRASGVSDRF SGSGSGTDFTLKISGVEAEDVG VYYCQQGLEFPDTFGAGTKLEL KRTVAAPSVFIFPPSDEQLKSGT ASVVCLLNNFYPREAKVQWKV DNALQSGNSQESVTEQDSKDST YSLSSTLTLSKADYEKHKVYAC EVTHQGLSSPVTKSFNRGEC | 56 |
| Anti-ITGA7 | CD47 | Heavy chain: Knob of 1790.6 | QVQLQESGPGLVKPSGTLSLTC AVSGVSIRSINWWNWVRQPPG KGLEWIGEIYHSGSTNYNPSLKS RVTISVDKSKNQFSLKLNSVTA | 57 |

TABLE 3-continued

| Antigen Binding Domain | | | | |
|---|---|---|---|---|
| Name | Target | Fragment | Sequence | SEQ ID NO |
| | | | ADTAVYYCARDGGIAVTDYYY YGLDVWGQGTTVTVSSASTKG PSVFPLAPSSKSTSGGTAALGCL VKDYFPEPVTVSWNSGALTSGV HTFPAVLQSSGLYSLSSVVTVPS SSLGTQTYICNVNHKPSNTKVD KKVEPKSCDKTHTCPPCPAPEL LGGPSVFLFPPKPKDTLMISRTP EVTCVVVDVSHEDPEVKFNWY VDGVEVHNAKTKPREEQYGST YRVVSVLTVLHQDWLNGKEYK CKVSNKALPAPIEKTISKAKGQP REPQVYTLPPCRDELTKNQVSL WCLVKGFYPSDIAVEWESNGQP ENNYKTTPPVLDSDGSFFLYSK LTVDKSRWQQGNVFSCSVMHE ALHNHYTQKSLSLSPGK | |
| Anti-ITGA7 | CD47 | Light chain of 1790.6 | EIVLTQSPATLSLSPGERATLSC RASESVSSNLAWYQQKPGQAP RLLIYGAFNRATGIPARFSGSGS GTDFTLTISSLEPEDFAVYYCQQ RSDWFTFGGGTKVEIKRTVAAP SVFIFPPSDEQLKSGTASVVCLL NNFYPREAKVQWKVDNALQSG NSQESVTEQDSKDSTYSLSSTLT LSKADYEKHKVYACEVTHQGL SSPVTKSFNRGEC | 58 |
| Anti-ITGA7 | CD47 | Heavy chain: Knob of 1790.7 | QVQLQESGPGLVKPSGTLSLTC AVSGVSIRSINWWNWVRQPPG KGLEWIGEIYHSGSTNYNPSLKS RVTISVDKSKNQFSLKLNSVTA ADTAVYYCARDGGIAVTDYYY YGLDVWGQGTTVTVSSASTKG PSVFPLAPSSKSTSGGTAALGCL VKDYFPEPVTVSWNSGALTSGV HTFPAVLQSSGLYSLSSVVTVPS SSLGTQTYICNVNHKPSNTKVD KKVEPKSCDKTHTCPPCPAPEL LGGPSVFLFPPKPKDTLMISRTP EVTCVVVDVSHEDPEVKFNWY VDGVEVHNAKTKPREEQYGST YRVVSVLTVLHQDWLNGKEYK CKVSNKALPAPIEKTISKAKGQP REPQVYTLPPCRDELTKNQVSL WCLVKGFYPSDIAVEWESNGQP ENNYKTTPPVLDSDGSFFLYSK LTVDKSRWQQGNVFSCSVMHE ALHNHYTQKSLSLSPGK | 59 |
| Anti-ITGA7 | CD47 | Light chain of 1790.7 | EIVLTQSPATLSLSPGERATLSC RASESVSSNLAWYQQKPGQAP RLLIYGAFNRATGIPARFSGSGS GTDFTLTISSLEPEDFAVYYCQQ RSDWFTFGGGTKVEIKRTVAAP SVFIFPPSDEQLKSGTASVVCLL NNFYPREAKVQWKVDNALQSG NSQESVTEQDSKDSTYSLSSTLT LSKADYEKHKVYACEVTHQGL SSPVTKSFNRGEC | 60 |

The signaling pathway modulator and the targeting moiety can be in any orientation. In one non-limiting embodiment, the signaling pathway modulator is connected to an amino terminus of the targeting moiety. In another non-limiting embodiment, the signaling pathway modulator is connected to a carboxy terminus of the targeting moiety.

In some instances, the agent can further comprise a linker. In some instances, the agent can further comprise an Fc domain. The Fc domain can be, for example, a human IgG1 Fc domain. The Fc domain can comprise a knob-in-hole. In some instances, the agent can further comprise a linker and an Fc domain.

In one non-limiting embodiment, (a) the signaling modulator comprises an amino acid sequence of any one of SEQ ID NOS: 1-30, or an amino acid sequence that is at least 90%, 95%, 98% or 99% identical to any one of SEQ ID NOS: 1-30, wherein the C-terminus or N-terminus of the signaling pathway modulator is coupled to a GGGGSGGGGSGGGGS linker (SEQ ID NO: 41) and a hIgG1 FC domain with a hole and N297G mutation; and (b) the antigen binding domain comprising a human IgG1 heavy chain with knob mutations and a N297G mutation and a light chain. In another non-limiting embodiment, (a) the signaling modulator comprises an amino acid sequence of any one of SEQ ID NOS: 1-30, or an amino acid sequence that is at least 90%, 95%, 98% or 99% identical to any one of SEQ ID NOS: 1-30, wherein the C-terminus or N-terminus of the signaling pathway modulator is coupled to a GGGGSGGGGS (SEQ ID NO: 42) and a hIgG1 FC domain with a hole and N297G mutation; and (b) the antigen binding domain comprising a human IgG1 heavy chain with knob mutations and a N297G mutation and a light chain. In some embodiments, the human IgG1 heavy chain comprises an amino acid sequence having at least about 90%, at least about 95%, at least about 98%, or at least about 99% sequence identity to the sequence set forth in SEQ ID NO: 39. In some embodiments, the human IgG1 heavy chain comprises an amino acid sequence having about one, about two, about three, about four, or about five amino acid modifications of the sequence set forth in SEQ ID NO: 39. In some embodiments, the light chain comprises an amino acid sequence having at least about 90%, at least about 95%, at least about 98%, or at least about 99% sequence identity to the sequence set forth in SEQ ID NO: 40. In some embodiments, the light chain comprises an amino acid sequence having about one, about two, about three, about four, or about five amino acid modifications of the sequence set forth in SEQ ID NO: 40 (Table 3). In some embodiments, the human IgG1 heavy chain comprises an amino acid sequence having at least about 90%, at least about 95%, at least about 98%, or at least about 99% sequence identity to the sequence set forth in any one of SEQ ID NOS: 51, 53, and 55. In some embodiments, the human IgG1 heavy chain comprises an amino acid sequence having about one, about two, about three, about four, or about five amino acid modifications of the sequence set forth in any one of SEQ ID NOS: 51, 53, and 55. In some embodiments, the light chain comprises an amino acid sequence having at least about 90%, at least about 95%, at least about 98%, or at least about 99% sequence identity to the sequence set forth in any one of SEQ ID NOS: 52, 54, and 56. In some embodiments, the light chain comprises an amino acid sequence having about one, about two, about three, about four, or about five amino acid modifications of the sequence set forth in any one of SEQ ID NOS: 52, 54, and 56.

In one aspect, the cargo comprises a vector. The vector can be any suitable macromolecule or complex of molecules comprising a polynucleotide to be delivered to a target cell. In some embodiments, the vector is a gene editing vector. In some embodiments, the vector is an expression vector. In some embodiments, the vector is a recombinant vector. In some embodiments, the vector comprises more than one vector described herein.

In one aspect, the vector is a non-viral vector. In some embodiments, the non-viral vector is capsid-free. In some embodiments, the non-viral vector is a deoxyribonucleic acid (DNA) vector. In some embodiments, the non-viral vector is a ribonucleic acid (RNA) vector. In some embodiments, the non-viral vector is obtained from a plasmid. In some embodiments, the non-viral vector is produced in a host cell.

In another aspect, the vector is a viral vector. In some embodiments, the viral vector is a replicative viral vector. In some embodiments, the viral vector is a non-replicative viral vector. In some embodiments, the viral vector is an adeno-associated virus (AAV) vector. The AAV vector can include a polynucleotide of interest (e.g., a transgene) that is flanked by AAV terminal repeat sequences (ITRs) and may be packaged into infectious viral particles. The AAV vector may be replicated when present in a host cell, such as a host cell that has been transfected with a vector encoding and expressing rap and cap gene products. In some embodiments, the viral vector is an adenoviral vector. In some embodiments, the viral vector is a retroviral vector. In some embodiments, the viral vector is a lentiviral vector. In some embodiments, the vector comprise a recombinant viral vector that comprises one or more nucleic acids described herein. In some embodiments, the viral vector is used to provide long-term gene expression. In some embodiments, the viral vector is used to provide short-term gene expression. In some embodiments, the viral vector is used to express a therapeutic molecule. In some embodiments, the therapeutic molecule is an nucleic acid, a protein, or an antibody.

In another aspect, the cargo comprises a nucleic acid. In some embodiments, the nucleic acid is a DNA. In some embodiments, the nucleic acid is an RNA. In some embodiments, the nucleic acid is double-stranded. In some embodiments, the RNA is an RNA interference-inducing (RNAi) molecule including, but not limited to, a siRNA, double strand RNA (dsRNA), small temporal RNA (stRNA), short-hairpin RNA (shRNA), microRNA (miRNA), and gene silencing variants thereof. In some embodiments, the nucleic acid is a double strand RNA (dsRNA). In some embodiments, the dsRNA reduces the expression of a target gene in a cell. In some embodiment, the cell is a muscle cell. In some embodiments, the reduction of the expression of the target gene treats diseases caused by the expression of the target gene.

In some embodiments, the dsRNA has a first oligonucleotide sequence and a second oligonucleotide sequence. In some embodiments, the second oligonucleotide sequence anneals to the first oligonucleotide sequence under biological conditions. In some embodiments, the first oligonucleotide sequence is from about 10 nucleotides to about 100 nucleotides in length. In some embodiments, the first oligonucleotide sequence is from about 10 nucleotides to about 90 nucleotides in length. In some embodiments, the first oligonucleotide sequence is from about 10 nucleotides to about 80 nucleotides in length. In some embodiments, the first oligonucleotide sequence is from about 10 nucleotides to about 70 nucleotides in length. In some embodiments, the first oligonucleotide sequence is from about 10 nucleotides to about 60 nucleotides in length. In some embodiments, the first oligonucleotide sequence is from about 10 nucleotides to about 50 nucleotides in length. In some embodiments, the first oligonucleotide sequence is from about 10 nucleotides to about 40 nucleotides in length. In some embodiments, the first oligonucleotide sequence is from about 10 nucleotides to about 30 nucleotides in length. In some embodiments, the first oligonucleotide sequence is from about 10 nucleotides to about 20 nucleotides in length. In some embodiments, the first oligonucleotide sequence is from about 20 nucleotides to about 100 nucleotides in length. In some embodiments, the first oligonucleotide sequence is from about 20 nucleotides to about 80 nucleotides in length. In some embodiments, the first oligonucleotide sequence is from about 20 nucleotides to about 70 nucleotides in length. In some embodiments, the first oligonucleotide sequence is from about 20 nucleotides to about 60 nucleotides in length. In some embodiments, the first oligonucleotide sequence is from about 20 nucleotides to about 50 nucleotides in length. In some embodiments, the first oligonucleotide sequence is from about 20 nucleotides to about 40 nucleotides in length. In some embodiments, the first oligonucleotide sequence is from about 20 nucleotides to about 30 nucleotides in length. In some embodiments, the first oligonucleotide sequence is from about 30 nucleotides to about 100 nucleotides in length. In some embodiments, the first oligonucleotide sequence is from about 30 nucleotides to about 90 nucleotides in length. In some embodiments, the first oligonucleotide sequence is from about 30 nucleotides to about 80 nucleotides in length. In some embodiments, the first oligonucleotide sequence is from about 30 nucleotides to about 70 nucleotides in length. In some embodiments, the first oligonucleotide sequence is from about 30 nucleotides to about 60 nucleotides in length. In some embodiments, the first oligonucleotide sequence is from about 30 nucleotides to about 50 nucleotides in length. In some embodiments, the first oligonucleotide sequence is from about 30 nucleotides to about 40 nucleotides in length. In some embodiments, the first oligonucleotide sequence is from about 40 nucleotides to about 100 nucleotides in length. In some embodiments, the first oligonucleotide sequence is from about 40 nucleotides to about 100 nucleotides in length. In some embodiments, the first oligonucleotide sequence is from about 40 nucleotides to about 90 nucleotides in length. In some embodiments, the first oligonucleotide sequence is from about 40 nucleotides to about 80 nucleotides in length. In some embodiments, the first oligonucleotide sequence is from about 40 nucleotides to about 70 nucleotides in length. In some embodiments, the first oligonucleotide sequence is from about 40 nucleotides to about 60 nucleotides in length. In some embodiments, the first oligonucleotide sequence is from about 40 nucleotides to about 50 nucleotides in length. In some embodiments, the first oligonucleotide sequence is from about 50 nucleotides to about 100 nucleotides in length. In some embodiments, the first oligonucleotide sequence is from about 50 nucleotides to about 90 nucleotides in length. In some embodiments, the first oligonucleotide sequence is from about 50 nucleotides to about 80 nucleotides in length. In some embodiments, the first oligonucleotide sequence is from about 50 nucleotides to about 70 nucleotides in length. In some embodiments, the first oligonucleotide sequence is from about 50 nucleotides to about 60 nucleotides in length. In some embodiments, the first oligonucleotide sequence is from about 60 nucleotides to about 100 nucleotides in length. In some embodiments, the first oligonucleotide sequence is from about 60 nucleotides to about 90 nucleotides in length. In some embodiments, the first oligonucleotide sequence is from about 60 nucleotides to about 80 nucleotides in length. In some embodiments, the first oligonucleotide sequence is from about 60 nucleotides to about 70 nucleotides in length. In some embodiments, the first oligonucleotide sequence is from about 70 nucleotides to about 100 nucleotides in length. In some embodiments, the first oligonucleotide sequence is from about 70 nucleotides to about 90 nucleotides in length. In some embodiments, the first oligonucleotide sequence is from about 70 nucleotides to about 80 nucleotides in length. In some embodiments, the first oligonucleotide sequence is from about 80 nucleotides to about 100 nucleotides in length. In some embodiments, the first oligonucleotide sequence is from about 80 nucleotides to about 90 nucleotides in length. In some embodiments, the first oligonucleotide sequence is from about 90 nucleotides to about 100 nucleotides in length. In some embodiments, the second oligonucleotide sequence is from about 10 nucleotides to about 100 nucleotides in length. In some embodiments, the second oligonucleotide sequence is from about 10 nucleotides to about 90 nucleotides in length. In some embodiments, the second oligonucleotide sequence is from about 10 nucleotides to about 80 nucleotides in length. In some embodiments, the second oligonucleotide sequence is from about 10 nucleotides to about 70 nucleotides in length. In some embodiments, the second oligonucleotide sequence is from about 10 nucleotides to about 60 nucleotides in length. In some embodiments, the second oligonucleotide sequence is from about 10 nucleotides to about 50 nucleotides in length. In some embodiments, the second oligonucleotide sequence is from about 10 nucleotides to about 40 nucleotides in length. In some embodiments, the second oligonucleotide sequence is from about 10 nucleotides to about 30 nucleotides in length. In some embodiments, the second oligonucleotide sequence is from about 10 nucleotides to about 20 nucleotides in length. In some embodiments, the second oligonucleotide sequence is from about 20 nucleotides to about 100 nucleotides in length. In some embodiments, the second oligonucleotide sequence is from about 20 nucleotides to about 80 nucleotides in length. In some embodiments, the second oligonucleotide sequence is from about 20 nucleotides to about 70 nucleotides in length. In some embodiments, the second oligonucleotide sequence is from about 20 nucleotides to about 60 nucleotides in length. In some embodiments, the second oligonucleotide sequence is from about 20 nucleotides to about 50 nucleotides in length. In some embodiments, the second oligonucleotide sequence is from about 20 nucleotides to about 40 nucleotides in length. In some embodiments, the second oligonucleotide sequence is from about 20 nucleotides to about 30 nucleotides in length. In some embodiments, the second oligonucleotide sequence is from about 30 nucleotides to about 100 nucleotides in length. In some embodiments, the second oligonucleotide sequence is from about 30 nucleotides to about 90 nucleotides in length. In some embodiments, the second oligonucleotide sequence is from about 30 nucleotides to about 80 nucleotides in length. In some embodiments, the second oligonucleotide sequence is from about 30 nucleotides to about 70 nucleotides in length. In some embodiments, the second oligonucleotide sequence is from about 30 nucleotides to about 60 nucleotides in length. In some embodiments, the second oligonucleotide sequence is from about 30 nucleotides to about 50 nucleotides in length. In some embodiments, the second oligonucleotide sequence is from about 30 nucleotides to about 40 nucleotides in length. In some embodiments, the second oligonucleotide sequence is from about 40 nucleotides to about 100 nucleotides in length. In some embodiments, the second oligonucleotide sequence is from about 40 nucleotides to about 100 nucleotides in length. In some embodiments, the second oligonucleotide sequence is from about 40 nucleotides to about 90 nucleotides in length. In some embodiments, the second oligonucleotide sequence is from about 40 nucleotides to about 80 nucleotides in length. In some embodiments, the second oligonucleotide sequence is from about 40 nucleotides to about 70 nucleotides in length. In some embodiments, the second oligonucleotide sequence is from about 40 nucleotides to about 60 nucleotides in length. In some embodiments, the second oligonucleotide sequence is from about 40 nucleotides to about 50 nucleotides in length. In some embodiments, the second oligonucleotide sequence is from about 50 nucleotides to about 100 nucleotides in length. In some embodiments, the second oligonucleotide sequence is from about 50 nucleotides to about 90 nucleotides in length. In some embodiments, the second oligonucleotide sequence is from about 50 nucleotides to about 80 nucleotides in length. In some embodiments, the second oligonucleotide sequence is from about 50 nucleotides to about 70 nucleotides in length. In some embodiments, the second oligonucleotide sequence is from about 50 nucleotides to about 60 nucleotides in length. In some embodiments, the second oligonucleotide sequence is from about 60 nucleotides to about 100 nucleotides in length. In some embodiments, the second oligonucleotide sequence is from about 60 nucleotides to about 90 nucleotides in length. In some embodiments, the second oligonucleotide sequence is from about 60 nucleotides to about 80 nucleotides in length. In some embodiments, the second oligonucleotide sequence is from about 60 nucleotides to about 70 nucleotides in length. In some embodiments, the second oligonucleotide sequence is from about 70 nucleotides to about 100 nucleotides in length. In some embodiments, the second oligonucleotide sequence is from about 70 nucleotides to about 90 nucleotides in length. In some embodiments, the second oligonucleotide sequence is from about 70 nucleotides to about 80 nucleotides in length. In some embodiments, the second oligonucleotide sequence is from about 80 nucleotides to about 100 nucleotides in length. In some embodiments, the second oligonucleotide sequence is from about 80 nucleotides to about 90 nucleotides in length. In some embodiments, the second oligonucleotide sequence is from about 90 nucleotides to about 100 nucleotides in length.

In some embodiments, the dsRNA comprises a sequence sufficiently complementary with a target sequence of a target gene. In some embodiments, the dsRNA has an asymmetric structure. In some embodiments, the dsRNA has two separate oligonucleotides that are linked by a third structure. In some embodiments, the dsRNA is a small interfering RNA (siRNA). In some embodiments, the dsRNA is a precursor of a siRNA. In some embodiments, the dsRNA is processed by Dicer to produce a siRNA. The dsRNA can be from a single RNA oligonucleotide that undergoes intramolecular annealing. In some embodiments, the dsRNA comprises at least one modification. In some embodiments, the at least one modification promotes Dicer to bind to the double-stranded RNA structure in an orientation that maximizes the double-stranded RNA structure's effectiveness in inhibiting gene expression. In some embodiments, the first and second oligonucleotides are not required to be completely complementary. In some embodiments, the siRNA is 19 nucleotides in length. In some embodiments, the siRNA is 20 nucleotides in length. In some embodiments, the siRNA is 21 nucleotides in length. In some embodiments, the siRNA is 22 nucleotides in length. In some embodiments, the siRNA is 23 nucleotides in length. In some embodiments, the siRNA is 24 nucleotides in length. In some embodiments, the siRNA is 25 nucleotides in length. In some embodiments, the siRNA is 26 nucleotides in length. In some embodiments, the siRNA is 27 nucleotides in length. In some embodiments, the siRNA is 28 nucleotides in length. In some embodiments, the siRNA is 29 nucleotides in length. In some embodiments, the siRNA is 30 nucleotides in length.

The siRNA can comprise an antisense strand and a sense strand. In some embodiments, the sense strand is from about 20 to about 30, or from about 22 to about 28 nucleotides in length. In some embodiments, the antisense strand is at least about 19 nucleotides in length. In some embodiments, the antisense strand has a modification at a 3' end and/or 5' end. In some embodiments, the antisense strand of the dsRNA has a 3' overhang. In some embodiments, the antisense strand of the siRNA is modified to include from about 1 to about 9 ribonucleotides on the 5' end to give a length of from about 20 to about 30 nucleotides.

In some embodiments, the siRNA is chemically modified. In some embodiments, the siRNA has reduced immunostimulatory activity compared to a corresponding RNA molecule not having the chemical modification. In some embodiments, the siRNA has increased serum stability compared to a corresponding RNA molecule not having the chemical modification.

In some embodiments, the siRNA is a shRNA. The shRNA can function as an siRNA. The shRNA can have double-stranded hairpin-like structure for increased stability. In some embodiments, the hairpin-like structure is from about 1 to about 30, from about 1 to about 24, or from about 1 to about 10, nucleotides in length. The sequence of the hairpin-like structure can include nucleotide residues unrelated to the target gene. In some embodiments, the hairpin-like structure is 5'-UU-3'. In some embodiments, the hairpin-like structure includes non-nucleotide moieties. In some embodiments, the hairpin-like structure does not include any non-nucleotides moieties. The shRNA can also comprise RNAs with stem-loop structures that contain mismatches and/or bulges. In some embodiments, the hairpin-like structure comprises nucleotides, non-nucleotides, or combinations of nucleotides and non-nucleotides.

In another aspect, the nucleic acid is single-stranded. In some embodiments, the nucleic acid is an antisense oligonucleotide (ASO). In some embodiments, the ASO comprises a sequence sufficiently complementary with a messenger RNA (mRNA) of a target gene of a target cell. In some embodiments, the target cell is a muscle cell. In some embodiments, the ASO targets a pre-mRNA. In some embodiments, the ASO comprises a backbone modification comprising a phosphorothioate linkage or a phosphorodiamidate linkage. In some embodiments, the ASO comprises a phosphorodiamidate morpholino, a locked nucleic acid, a peptide nucleic acid, a 2'-O-methyl, a 2'-Fluoro, or a 2'-O-methoxyethyl moiety. In some embodiments, the ASO is a morpholino. In some embodiments, the ASO comprises at least one modified sugar moiety. In some embodiments, the ASO is from 8 to 50 nucleotides in length. In some embodiments, the ASO is from 8 to 40 nucleotides in length. In some embodiments, the ASO is from 8 to 35 nucleotides in length. In some embodiments, the ASO is from 8 to 30 nucleotides in length. In some embodiments, the ASO is from 8 to 25 nucleotides in length. In some embodiments, the ASO is from 8 to 20 nucleotides in length. In some embodiments, the ASO is from 8 to 15 nucleotides in length. In some embodiments, the ASO is from 9 to 50 nucleotides in length. In some embodiments, the ASO is from 9 to 40 nucleotides in length. In some embodiments, the ASO is from 9 to 35 nucleotides in length. In some embodiments, the ASO is from 9 to 30 nucleotides in length. In some embodiments, the ASO is from 9 to 25 nucleotides in length. In some embodiments, the ASO is from 9 to 20 nucleotides in length. In some embodiments, the ASO is from 9 to 15 nucleotides in length. In some embodiments, the ASO is from 10 to 50 nucleotides in length. In some embodiments, the ASO is from 10 to 40 nucleotides in length. In some embodiments, the ASO is from 10 to 35 nucleotides in length. In some embodiments, the ASO is from 10 to 30 nucleotides in length. In some embodiments, the ASO is from 10 to 25 nucleotides in length. In some embodiments, the ASO is from 10 to 20 nucleotides in length. In some embodiments, the ASO is from 10 to 15 nucleotides in length. In some embodiments, the ASO is from 11 to 50 nucleotides in length. In some embodiments, the ASO is from 11 to 40 nucleotides in length. In some embodiments, the ASO is from 11 to 35 nucleotides in length. In some embodiments, the ASO is from 11 to 30 nucleotides in length. In some embodiments, the ASO is from 11 to 25 nucleotides in length. In some embodiments, the ASO is from 11 to 20 nucleotides in length. In some embodiments, the ASO is from 11 to 15 nucleotides in length. In some embodiments, the ASO is from 12 to 50 nucleotides in length. In some embodiments, the ASO is from 12 to 40 nucleotides in length. In some embodiments, the ASO is from 12 to 35 nucleotides in length. In some embodiments, the ASO is from 12 to 30 nucleotides in length. In some embodiments, the ASO is from 12 to 25 nucleotides in length. In some embodiments, the ASO is from 12 to 20 nucleotides in length. In some embodiments, the ASO is from 12 to 15 nucleotides in length.

In another aspect, the cargo comprises a lipid nanoparticle (LNP). The LNP comprises a lipid formulation that can be used to deliver a vector to a target site of interest (e.g., cell, tissue, organ, and the like).

In some embodiments, the nucleic acid is encapsulated in the LNP. In some embodiments, the LNP comprises a lipid selected from the group consisting of an ionizable or cationic lipid, a helper phospholipid, a conjugated lipid, a PEG-conjugated lipid, a cholesterol-based lipid, and a combination thereof. In some embodiments, the ionizable lipid is ALC-0315, SM-102, or MC-3. In some embodiments, the cholesterol-based lipid is cholesterol or derivatives thereof. In some embodiments, the helper phospholipid is DSPC. In some embodiments, the conjugated lipid is PEG-lipid conjugates, polyoxazoline (POZ)-lipid conjugates, polyamide-lipid conjugates (such as ATTA-lipid conjugates), cationic-polymer lipid (CPL) conjugates, or mixtures thereof. In some embodiments, the conjugated lipid molecule is a PEG-lipid conjugate, for example, a (methoxy polyethylene glycol)-conjugated lipid. In some embodiments, the PEG-conjugated lipid is ALC-0159. In some embodiments, the PEG-lipid conjugate is PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanolamine (PEG-PE), PEG succinate diacylglycerol (PEGS-DAG) (such as 4-O-(2',3'-di(tetradecanoyloxy)propyl-1-O-(w-methoxy(polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, or a mixture thereof.

In some embodiments, the cationic lipid is an amino lipid. In some embodiments, the LNP comprises a non-cationic lipid. In some embodiments, the non-cationic lipid is a neutral uncharged, zwitterionic, or anionic lip. In some embodiments, the non-ionic lipid is selected from the group consisting of distearoyl-sn-glycero-phosphoethanolamine, di stearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), di stearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOP 5), sphingomyelin (SM), dimyristoyl phosphatidylcholine (DMPC), dimyristoyl phosphatidylglycerol (DMPG), di stearoylphosphatidylglycerol (DSPG), dierucoylphosphatidylcholine (DEPC), palmitoyloleyolphosphatidylglycerol (POPG), dielaidoyl-phosphatidylethanolamine (DEPE), lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, and dilinoleoylphosphatidylcholine.

In some embodiments, the ionizable lipid is present at a molar ratio of 35-55%. In some embodiments, the PEG-conjugated lipid is present at a molar ratio of 0.25% to 3%. In some embodiments, the helper phospholipid is present at a molar ratio of 5% to 20%. In some embodiments, the cholesterol-based lipid is present at a molar ratio of 20% to 45%. In some embodiments, the cationic lipid may be present in an amount of from about 10% by weight of LNP to about 85% by weight of the lipid nanoparticle, or from about 50% by weight of LNP to about 75% by weight of the LNP. All lipid molar ratios described here are relative to the total lipid content of the LNP. Molar ratios of lipids in the LNP, for example the ionizable lipid, non-cationic-lipid, sterol, and PEG/conjugated lipid, can be varied as needed.

In some embodiments, the LNP does not comprise any phospholipids. In some embodiments, the LNP comprises one or more additional compounds. In some embodiments, the additional compounds are administered separately. In some embodiments, the additional compounds can be included in the LNP provided herein. In some embodiments, the additional compounds can be selected from the group consisting of small or large organic or inorganic molecules, monosaccharides, disaccharides, trisaccharides, oligosaccharides, polysaccharides, peptides, proteins, peptide analogs and derivatives thereof, peptidomimetics, nucleic acids, nucleic acid analogs and derivatives, an extract made from biological materials, or any combinations thereof.

In another aspect, the cargo comprises a drug. In yet another aspect, the cargo comprises two or more types of drugs. In some embodiment, the drug is a therapeutic agent for muscle diseases. In some embodiments, the drug is conjugated to the antigen-binding domain via a linker. In some embodiments, the linker is cleavable. In some embodiments, the linker is cleavable by a cleaving agent that is present in an intracellular environment (e.g., within a lysosome or endosome or caveolea). In some embodiments, the linker contains peptide (e.g. oligopeptide, or di-, tri-, tetra- or penta-peptide containing linkers). In some embodiments, the linker comprises a valine-citrulline, valine-alanine or phenylalanine-lysine dipeptide. In some embodiments, the drug conjugated to the antigen-binding domain functions as a targeted drug delivery system. In some embodiments, the conjugation of the drug to the antigen-binding domain is site-specific. In some embodiments, the conjugation of the drug to the antigen-binding domain is not site-specific. In some embodiments, the drug is a prodrug that is activated upon administration to a subject. In some embodiments, the drug is a small molecule drug. In some embodiments, the drug is a peptide drug. In some embodiments, the drug is a protein drug.

In some embodiments, the drug is a toxin. In some embodiments, the toxin is a cytotoxic molecule. In some embodiments, the toxin is a radionuclide. In some embodiments, the toxin is a chemotherapeutic drug. In some embodiments, the toxin is an anticancer agent. In some embodiments, the anticancer agent is adriamycin, daunomycin, mitomycin, cisplatin, vincristine, epirubicin, methotrexate, 5-fluorouracil, aclacinomycin, nitrogen mustard, cyclophosphamide, bleomycin, daunorubicin, doxorubicin, vincristine, vinblastine, or a combination thereof. In some embodiments, the toxin is cell membrane permeable. In some embodiments, the toxin is dianthin or saporin. In some embodiments, the toxin is *Pseudomonas aeruginosa* exotoxin (PE) or a cytotoxic fragment thereof (e.g., PE38). In some embodiments, the toxin is monomethyl auristatin E (MMAE) or MMAF.

In another aspect, the cargo comprises an immune modulator. In some embodiments, immune modulator is immunosuppressant. In some embodiments, the immune modulator decreases an activity of an immune system. In some embodiments, immune modulator is immunostimulatory. In some embodiments, the immune modulator increases an activity of an immune system. In some embodiments, the immune modulator is an interleukin (IL). In some embodiments, the interleukin is an IL-10. In some embodiments, the interleukin is an IL-35. In some embodiments, the interleukin is an IL-4. In some embodiments, the interleukin is an IL-13. In some embodiments, the interleukin is an IL-27. In some embodiments, the interleukin is an IL-37. In some embodiments, the interleukin is a combination of interleukins provided herein. In some embodiments, the immune modulator is a chemokine. In some embodiments, the chemokine is CCL14, CCL19, CCL20, CCL21, CCL25, CCL27, CXCL12, CXCL13, CXCL-8, CCL2, CCL3, CCL4, CCL5, CCL11, CXCL10, or a combination thereof.

In another aspect, provided herein is a pharmaceutical composition comprising (i) any of the agents and (ii) one or more pharmaceutically acceptable excipient(s).

Functional Assays

The agents described herein can be tested in any in vitro and/or in vitro functional assay, such as those described below.

In Vitro Functional Assay

Ligand binding properties of amino acid substituted variants of human insulin-like growth factor I (IGF-I) are analyzed with respect to their binding affinities and binding kinetics to recombinant IGF binding protein 1 (IGFBP-1) and a soluble form of the IGF type I receptor (sIGF-IR), respectively. Ligand binding kinetic rates are determined using BIAcore biosensor interaction analysis technology. Secondary structure content of the IGF-I variants is estimated using far-UV circular dichroism spectroscopy, followed by variable selection secondary structure calculations.

In Vivo Functional Assay

Male mdx mice (3-6 months of age; 4-5 mice per group) are obtained. Animal care and experimental procedures are conducted in accordance with the Code of Practice for the Care and Use of Animals for Scientific Purposes.

Mice are administered a negative control, an IGF-1 variant, GH variant, bFGF variant, IL4 variant, or bimagrumab, alone, an antigen binding domain alone, or an agent described herein. Groups are administered treatment once weekly for three weeks via injection (e.g., intravenous injection). Following onset of treatment, mice are monitored and weighed every second day until the conclusion of the study. Body weight and muscle mass are assessed prior to treatment, during treatment, and at the conclusion of the study.

Methods of Modulation

Provided herein is method of modulating a muscular dystrophy (MD) comprising delivering to a region adjacent to a muscle any of the agents described herein. In some instances, the administration is to a subject and the subject is a mammal. The mammal can be, for example, a human. Administering can comprise injecting the subject at a location near a skeletal muscle, a muscle satellite cell (e.g., a skeletal muscle satellite cell), a skeletal muscle, a cardiac muscle, a smooth muscle, or a muscle fiber. Injection can be any suitable route of injection including, but not limited to, intravenous (IV), subcutaneous (SQ), intramuscular (IM), intrathecal (IT) and intraperitoneal. Administration of the agent to the subject induces signaling of the IGF-1 signaling pathway, the GH signaling pathway, the bFGF signaling pathway, the IL4 signaling pathway, or inhibits ActRII. In certain instances, a pharmaceutical composition is administered to the subject, where the pharmaceutical composition comprises the agent and one or more pharmaceutically acceptable carrier(s). The term "pharmaceutically acceptable carrier" as used herein, refers to a carrier or excipient for administration of an active substance. The pharmaceutically acceptable carrier can comprise any substance or vehicle suitable for delivering the agent to the subject. The term refers to any pharmaceutical carrier that may be administered without undue toxicity. Suitable carriers may be, for example, one or more optional stabilizers, diluents, and/or excipients.

A muscular dystrophy to be treated with the methods described herein include, for example, Duchenne muscular dystrophy (DMD), Becker muscular dystrophy (BMD), a limb-girdle muscular dystrophy (LGMD), and/or a congenital muscular dystrophy.

A subject to be treated with the described methods has been diagnosed with a muscular dystrophy. Diagnosis can be based upon one or more of the following: family history; genetic testing; cardiomyopathy; calf muscle hypertrophy; cognitive impairment; delayed speech and language development; elevated serum creatine kinase; muscle loss; weakness of the face, shoulder girdle, and upper arm(s) with relative sparing of the deltoid muscles; or any combination thereof. Assessment can also include nerve conduction velocity testing (NCV) and electromyography (EMG).

In one instance, a subject treated with an agent described herein experiences at least a 2-fold, 5-fold, 10-fold, 15-fold, 20-fold, 50-fold, 100-fold improvement, or more, in one or more symptoms. Improvement can be in comparison to treatment with a placebo or in comparison to the same subject prior to treatment.

Certain Definitions

All terms are intended to be understood as they would be understood by a person skilled in the art. Unless defined otherwise, all technical and scientific terms used herein have the same meaning as commonly understood by one of ordinary skill in the art to which the disclosure pertains.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein.

The terminology used herein is for the purpose of describing particular cases only and is not intended to be limiting. In this application, the use of the singular includes the plural unless specifically stated otherwise. As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" means a range within 10% of a given value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable" refers to approved or approvable by a regulatory agency of the Federal or a state government or listed in the U.S. Pharmacopeia (U.S.P.) or other generally recognized pharmacopeia for use in animals, including humans.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The term "optional" or "optionally" denotes that a subsequently described event or circumstance can but need not occur, and that the description includes instances where the event or circumstance occurs and instances in which it does not.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The "percent sequence identity" between a reference amino acid sequence and a query amino sequence (i.e., the amino sequence being analyzed to determine whether it is within a particular percent sequence identity with the reference amino acid sequence) is determined by optimally aligning the sequences using the Needleman-Wunsch alignment algorithm with a gap existence penalty of 11 and a gap extension penalty of 1 and comparing the sequences. The number of exact matches, divided by the total number of positions in the alignment (which corresponds with the number of amino acids in the reference sequence plus any gaps in the reference sequence when aligned with the query sequence) is determined and expressed as a percentage. This is the percent sequence identity between the query amino acid sequence and the reference amino acid sequence (i.e., percent sequence identity=(# of exact matches/(total # of positions in alignment)*100). An alignment using the Needleman-Wunsch alignment algorithm (with a gap existence penalty of 11 and a gap extension penalty of 1) can be generated using the "Global Align" BLAST program available at https://blast.ncbi.nlm.nih.gov/Blast.cgi.

The "percent sequence identity" between a reference nucleic acid sequence and a query nucleic acid sequence (i.e., the nucleic acid sequence being analyzed to determine whether it is within a particular percent sequence identity with the reference nucleic acid sequence) is determined by optimally aligning the sequences using the Needleman-Wunsch alignment algorithm (with match/mismatch scores of 2, −3, a gap existence penalty of 5, and a gap extension penalty of 2) and comparing the aligned nucleic acids. The number of exact match-es divided by the total number of nucleotides in the alignment (which corresponds with the number of nucleotides in the reference sequence plus any gaps in the reference sequence when aligned with the query sequence) is determined and expressed as a percentage. This is the percent sequence identity between the query nucleic acid sequence and the reference nucleic acid sequence (i.e., percent sequence identity=(# of exact matches)/(total # of nucleotides in the alignment)*100). An alignment using the Needleman-Wunsch alignment algorithm (with match/mismatch scores of 2, −3, a gap existence penalty of 5, and a gap ex-tension penalty of 2) can be generated using the "Global Align" BLAST program available at https://blast.ncbi.nlm-.nih.gov/Blast.cgi.

EXAMPLES

Example 1: Methods and Procedure

The methods and procedure described herein were applied in all the Examples.

In Vitro Potency Assay (pAKT Assay)

$15\times10^6$ DU145 cells (obtained from ATCC) frozen down at passage 5 (P5) were reseeded in a T175 culture flask containing DMEM/F12 (1:1) medium (Gibco 11320-033) supplemented with 10% FBS (Gibco 10437-028) and 10 µg/mL Gentamicin (Gibco 15710-064) (hereafter referred to as culture medium) and expanded. At 80-90% confluency, cells were trypsinized, manually counted using a hemocytometer, resuspended at $3\times10^5$ cells per mL in culture medium, and then reseeded in 24-well plates (Corning 3524) in 0.5 mL aliquots per well (150,000 cells/well). 14-16 hours after reseeding, the culture medium was removed, and following a wash with 1 mL PBS, cultured for 6 h in 225 µL serum-free culture medium supplemented with 0.2% BSA (Millipore A3059). 25 µL aliquots of the following growth factor dilution series were added to the cells in duplicate: 4570, 1370, 410, 125, 37, 11.1, and 3.3 nM rhIGF1 (PeproTech #100-11) (SEQ ID NO: 1) and Fusion Antibodies (comprising three polypeptide chains: SEQ ID NOS: 2, 39, and 40). After 15 min incubation at 37° C., medium was aspirated and cells lysed in 150 µL 1×PTR buffer (Extraction Buffer 5×PTR, Abcam ab193970) containing 1× Extraction Enhancer Buffer (Extraction Enhancer Buffer 50×, Abcam ab193971) and protease/phosphatase inhibitors (one Pierce mini tablet [A32959] per 10 mL 1×PTR). After 15-30 min incubation on ice, plates were vortexed, and lysates transferred to Eppendorf tubes and stored at −80° C. for assessment of IGF1R-AKT signaling strength using the Human/Mouse/Rat Phospho-Akt (S473) Pan Specific DuoSet IC ELISA (RnD #DYC887B).

C2C12 mouse muscle myoblast cells (ATCC #CRL-1772) were cultured in DMEM containing 4.5 g/L glucose (Corning 10-013-CV) supplemented with 10% FBS (Gibco 10437-028) and 10 µg/mL Gentamicin (15710-064). At 70-80% confluency, cells were trypsinized, manually counted using a hemocytometer, resuspended at $2\times10^5$ cells per mL in differentiation medium (DMEM (Corning 10-013-CV) supplemented with 2% horse serum (Sigma, #H1138) and 10 µg/mL Gentamicin (Gibco 15710-064), and seeded in 24-well plates (Corning 3524) in 0.5 mL aliquots per well (100,000 cells/well). After 5 days on differentiation medium C2C12 cells were washed with 1 mL PBS and then serum-starved for 6 h in 225 µL serum-free culture medium supplemented with 0.2% BSA (Millipore A3059). The remainder of the protocol is the same as described above for DU145 cells.

ELISAs were performed in 384-well plates to the manufacturers' recommendation with minor modifications. Briefly, wells of 384-well plates were coated with 25 µL 6 µg/mL phospho-Akt1 (S473) capture antibody (RnD #841692) in PBS (25 µL per 384-well), sealed and placed overnight at RT. Wells were washed 4× with 100 µL PBS containing 0.05% Tween 20, and blocked with 50 µL PBS containing 2% BSA for 1-2 h at room temperature (RT). Wells were washed 4× with 100 µL PBS containing 0.05% Tween 20 and incubated with 25 µL of lysate or P-AKT standard (RnD #841694) for 2 h at RT. Wells were washed 4× with 100 µL PBS containing 0.05% Tween 20 and then incubated with 25 µL 100 ng/mL phospho-Akt1 (S473) detection antibody (RnD #843081) diluted in PBS containing 1% BSA for 1 h at RT. Wells were washed 4× with 100 µL PBS containing 0.05% Tween 20 and incubated with 25 µL Streptavidin-HRP A (RnD #890803) diluted 1:200 in PBS containing 1% BSA for 20 min at RT. Wells were washed 4× with 100 µL PBS containing 0.05% Tween 20 and incubated with 25 µL TMB substrate solution (Abcam TMB ELISA Substrate High Sensitivity, #ab171523), and incubated for 2-20 min at RT (timing depends on the intensity of the color reaction). 12.5 µL stop solution (RnD #DY994) was added and the OD450 of each well measured using a BMG Labtech CLARIOstar® Plus Microplate Reader. EC50 values were calculated using Prism 10 software.

Potency Shift Assay

Undifferentiated wildtype (WT) and ITGA7-knockout (KO) C2C12 cells were resuspended at $0.5\times10^5$ cells per mL in culture medium and seeded in 24-well plates (Corning, #3524) in 0.5 mL aliquots per well (25,000 cells/well). The remainder of the protocol is the same as described above for DU145 cells, with the exception of the volume of the lysis buffer, which is 200 µL for C2C12 cells.

Animal Studies

Wild-type (WT) male C57BL/6J (Jackson Labs, Strain #000664) or C57BL/10ScSn-Dmdmdx/J (mdx) (Jackson Labs, Strain #001801) were purchased at 8 weeks of age from Jackson Laboratories. All animal studies were conducted in compliance with the protocols approved by the Explora Biolabs Institutional Animal Care and Use Committee.

In Vivo PK Analysis (Human IgG Assay)

Wild-type (WT) male C57BL/6J (Jackson Labs, Strain #000664) were purchased at 8 weeks of age and shipped to the Cavalry Biosciences vivarium facility managed by Explora Biolabs in San Francisco, CA. After at least 1 week of acclimation mice were weighed and administered custom therapeutic proteins from Fusion Antibodies, Inc. by lateral tail vein injection with insulin syringes (BD, 329424) in dose volumes of 5-10 ml/kg at dose ranges of 0.3-15 mg/kg. Individual animals were dosed for timepoints collected at 1, 4, 24, 48, 96, 144, and 240 hours post dose with 3-5 animals per timepoint. At the appropriate timepoint, animals were anesthetized with 5% isoflurane using an RC2 rodent circuit controller (922100, VetEquip) and plasma was harvested from blood collected from the inferior vena cava by centrifugation in microtainers containing Dipotassium EDTA (BD, 365974). Samples were frozen on dry ice and stored at −80 C until future analysis. For analysis, plasma samples were diluted as determined empirically for each dose level and evaluated for concentration of therapeutic proteins by a sandwich ELISA that for the humanized Fc region of therapeutic proteins (Human IgG ELISA Kit, ab195215, Abcam) according to the manufacturer's instructions. Standard curves for each therapeutic protein being analyzed were generated in sample diluent supplied with the assay at concentration of 100, 50, 25, 12.5, 6.25, 3.125, 1.5625, and 0 ng/ml. OD450 data for standard curves and each sample was collected using a Promega GloMAX Discover Microplate Reader. Sample data was interpolated from standard curves, corrected for dilution factors, plotted and half-lives were calculated using two-phase decay in Prism 9 (Graphpad).

In Vivo Distribution (Human IgG Assay)

C57BL/10ScSn-Dmdmdx/J (mdx) (Jackson Labs, Strain #001801) or control age-matched wild-type (WT) male C57BL/6J (Jackson Labs, Strain #000664) were weighed and administered custom therapeutic proteins from Fusion Antibodies, Inc. by lateral tail vein injection with insulin syringes (BD, 329424) in dose volumes of 5-10 ml/kg at dose ranges of 0.3-15 mg/kg. Individual animals were dosed for timepoints collected at 4, 24 or 72 hours post dose with 5-8 animals per therapeutic protein/timepoint. At the appropriate timepoint animals were anesthetized with 5% isoflurane using an RC2 rodent circuit controller (922100, VetEquip) and plasma was harvested from blood collected from the inferior vena cava by centrifugation in microtainers containing Dipotassium EDTA (BD, 365974). Animals were then perfused with 20-30 ml of Dulbecco's Phosphate-Buffered Salt Solution (DPBS, Corning, 21030CV) through the heart apex. Multiple tissue were collected including some or all of the following: heart, kidney, liver, lungs, gastrocnemius muscle, diaphragm muscle, tibialis anterior muscle and forearm muscle. Tissue was weighed and flash frozen on dry ice and stored at −80 C until later analysis. Samples were homogenized 1 ml/250 mg tissue in Extraction Buffer 5×PTR (Abcam #ab193970) containing protease and phosphatase inhibitors (Thermo Scientific, A32959) using a NextAdvance Bullet Blender Gold (BB24AU) with Green, Navy or Red Eppendorf Lysis Kits (NextAdvance). Samples were diluted as determined empirically for each tissue and/or dose level and evaluated for concentration of therapeutic proteins by a sandwich ELISA that for the humanized Fc region of therapeutic proteins (Human IgG ELISA Kit, ab195215, Abcam) according to the manufacturer's instructions. Standard curves for each therapeutic protein being analyzed were generated in sample diluent supplied with the assay at concentration of 100, 50, 25, 12.5, 6.25, 3.125, 1.5625, and 0 ng/ml. OD450 data for standard curves and each sample was collected using a Promega GloMAX Discover Microplate Reader. Sample data was interpolated from standard curves, corrected for dilution factors, plotted and IgG levels were plotted as ng/ml/sample in Prism 9 (Graphpad).

In Vivo PD Analysis

For evaluation of therapeutic protein PD, IGFR1 activation was assessed by determining relative tissue levels of phospho-AKT using the phospho-Akt (S473) Pan Specific DuoSet IC ELISA (RnD #DYC887B-2) and processing tissues as above. ELISAs were performed in 384-well plates to the manufacturers' recommendation with minor modifications. Briefly, wells of 384-well plates were coated with 25 μl 6 μg/ml phospho-Akt1 (S473) capture antibody (#841692) in PBS (25 μl per 384-well), sealed and placed overnight at RT. Wells were washed 4× with 100 μl PBS containing 0.05% Tween 20, and blocked with 50 μl PBS containing 2% BSA for 1-2 h at room temperature (RT). Wells were washed 4× with 100 μl PBS containing 0.05% Tween 20 and incubated with 25 μl of lysate or P-AKT standard for 2 h at RT. Wells were washed 4× with 100 μl PBS containing 0.05% Tween 20 and then incubated with 25 μl 100 ng/ml phospho-Akt1 (S473) detection antibody (#843081) diluted in PBS containing 1% BSA for 1 h at RT. Wells were washed 4× with 100 μl PBS containing 0.05% Tween 20 and incubated with 25 μl Streptavidin-HRP A (RnD #890803) diluted 1:200 in PBS containing 1% BSA for 20 min at RT. Wells were washed 4× with 100 μl PBS containing 0.05% Tween 20 and incubated with 25 μl TMB substrate solution (Abcam TMB ELISA Substrate High Sensitivity (ab171523; lot GR3427893-1)), and incubated for 10-20 min at RT. 12.5 μl stop solution (RnD #895926 from Ancillary Kit 2) was added. OD450 data for standard curves and each sample was collected using a Promega GloMAX Discover Microplate Reader. Sample data was interpolated from standard curves, corrected for dilution factors, plotted and pAKT levels were plotted in Prism 10 (Graphpad).

Immunohistochemistry (IHC) Assay

Muscles from Wild-type (WT) male C57BL/6J (Jackson Labs, Strain #000664) or C57BL/10ScSn-Dmdmdx/J (mdx) (Jackson Labs, Strain #001801) were isolated 4-72 hours after dosing with 3-10 mg/kg CV1707-12. Tissue was fixed in 4% paraformaldehyde overnight and switched to 30% sucrose 24 hours later. Muscles was then embedded in OCT medium and sectioned in 10-micron sections and adhered to glass slides. Tissue was then stained for hIgG using rabbit anti-human IgG followed by a secondary antibody and DAB development kit. In brief, sections were washed with PBS+0.1% Tween-20 and permeabilized with PBS+0.3% TrixonX-100. Next, slides were blocked with hydrogen peroxide for 10 minutes and then incubated with rabbit anti-human IgG (Invitrogen #31143) for 24 hours at 1:2000. Slides were then washed with PBS+0.1% Tween-20 3×, incubated with secondary antibody, anti-Rabbit IgG HRP Polymer (Vector Labs). Slides were then washed with PBS+0.1% Tween-20 3× and developed with DAB (3,3'-diaminobenzidine) substrate for 3-5 minutes at RT and rinsed in DI water for 2 minutes. Stains were then counterstained with Methyl Green for 1 minute at room temperature, rinsed in DI water, and dehydrated with 100% isopropanol two times for two minutes each. Slides were then coverslipped and imaged.

Western Blot Analysis and Quantitation

Tissue lysates were generated from 4 mice per treatment and time point. These samples were pooled and mixed 1:1 with 2× Laemmli Sample Buffer (Bio-Rad, #1610737) and betamercaptoethanol according to manufacturer's instruction and boiled for 10 minutes. Samples for kidney were further diluted 3-fold. 3.5 μL-9 μL was loaded onto a 4-15% SDS-PAGE gel (Bio-Rad, #4561086) and run at 200 V for about 45 minutes. Gels were transferred to a PVDF-type transfer membrane (Millipore, #IPVH00010) with standard western blotting procedures. Membranes were stained with Ponceau S to visualize protein loading. Primary antibody incubations were overnight at 4° C., secondary antibody incubation was for 1 h at RT. Antibodies used: P-AKTS473 1:2,000 (Cell Signaling Technology, #4060), AKT 1:1,000 (Cell Signaling Technology, #9272), GAPDH 1:2,000 (Boster, 00227-1), Goat anti-Rabbit IgG (H+L)-HRP 1:50,000 (Invitrogen, #31460). Signal was detected by incubation with chemiluminescent substrate (ThermoScientific, #34580) and autoradiography film (ECE Scientific, #E3018).

Generation of C2C12 Itga7 Knockout Cells

C2C12-ITGA7 KO cells were generated by using the Alt-R CRISPR-Cas9 System (IDT) according to the manufacturer's protocol with Itga7-targeting gRNA oligo/AltR1/rCrU rCrUrC rUrGrU rCrGrA rGrArC rUrCrA rUrArU rGrUrU rUrUrA rGrArG rCrUrA rUrGrC rU/AltR2/ and Lipofectamine CRISPRMAX transfection reagent (Thermo Fisher Scientific, #CMAX00008). Absence of MATN3 was verified by immunofluorescence staining with anti-ITGA7 (Cavalry Biosciences, #CV1707-4).

ELISAs were performed in 384-well plates to the manufacturers' recommendation with minor modifications. Briefly, wells of 384-well plates were coated with 25 μL 6 μg/mL phospho-Akt1 (S473) capture antibody (RnD #841692) in PBS (25 μL per 384-well), sealed and placed overnight at room temperature. Wells were washed 3× with 100 μL PBS containing 0.05% Tween 20, and blocked with 50 μL PBS containing 2% BSA for 1-2 h at room temperature (RT). Wells were washed 3× with 100 μL PBS containing 0.05% Tween 20 and incubated with 25 μL of lysate or P-AKT standard (RnD #841694) for 2 h at RT. Wells were washed 3× with 100 μL PBS containing 0.05% Tween 20 and then incubated with 25 μL 100 ng/mL phospho-Akt1 (S473) detection antibody (RnD #843081) diluted in PBS containing 1% BSA for 1 h at RT. Wells were washed 3× with 100 μL PBS containing 0.05% Tween 20 and incubated with 25 μL Streptavidin-HRP A (RnD #890803) diluted 1:200 in PBS containing 1% BSA for 20 min at RT. Wells were washed 3× with 100 μL PBS containing 0.05% Tween 20 and incubated with 25 μL TMB substrate solution (Abcam TMB ELISA Substrate Highest Sensitivity, #ab171522), and incubated for 2-20 min at RT (timing depends on the intensity of the color reaction). 12.5 μL stop solution (RnD #DY994) was added and the OD450 of each well measured using a BMG Labtech CLARIOstar® Plus Microplate Reader. $EC_{50}$ values were calculated using Prism 10 software.

Hindlimb Casting

Mice were acclimated for 14 or more days following arrival. Baseline muscle function was measured and animals were assigned to balanced groups based on initial bodyweights and baseline force measurements. Mice then underwent hindlimb casting, or sham casting on one limb and were dosed with vehicle or 10 mg/kg CAV-003 every 4 days by intraperitoneal injection. After 2 weeks of casting, casts were removed, muscle function was measured again, then euthanized and necropsied for further tissue analysis.

For cast installation, mice were anesthetized by inhalation or ~5% isoflurane. Once sedated the hindlimb was wiped with three alternating washes of povidone-iodine, then 70% ethanol, and allowed to dry. The hindlimb was then loosely wrapped in sterile surgical gauze and a custom-made plastic immobilization device, consisting of a small, tapered tube, about the diameter of the mouse leg. This was then placed on the hindlimb, with the foot in full extension, to ensure the maximal in vivo unloading of the plantar flexor group. The cast extended proximal to the knee and distal to the ankle. The immobilization device is then fixed to the hindlimb using Vetbond tissue glue. After sedation mouse was removed from anesthesia, isothermal pad and surgical field then placed in a recovery cage. Once fully ambulatory the mice were relocated back to original housing. Dietgel was provided to the animals for the duration of the study. Animals were monitored daily for signs of inflammation around the cast to ensure no impact on animal welfare. For Sham cast, animals underwent all procedures but casts were not secured with Vetbond and is removed. The plastic tube used for the casting was 7.9 mm in diameter by 25 mm in length, going from just above the knee of the mouse to just below the ankle. The limb was loosely wrapped in gauze and gently slipped into the tube, with the paw in full extension. The mouse was able to ambulate with relative ease, simply dragging the casted limb on the cage floor. This method of casting does not require specialized housing or husbandry conditions. In the event the cast needed to be replaced, it was done so immediately.

In Vivo Hindlimb Muscle Function

Muscle performance was measured in vivo with a 305 C muscle lever system (AuroraScientific Inc., Aurora, CAN). Mice were anesthetized by inhalation or ~5% isoflurane, placed on a thermostatically controlled table where anesthesia maintenance was achieved via nose-cone (~2-3% isofluorane). The knee was isolated by pressing a pin against the tibial head and the foot was then firmly fixed to a footplate on the motor shaft. For the plantarflexor muscle group, contractions were elicited by percutaneous electrical stimulation of the sciatic nerve. Optimal isometric twitch torque was determined by increasing the current with a minimum of 30 seconds between each contraction to avoid fatigue. A series of stimulations were then performed at increasing frequency of stimulation (0.2 ms pulse, 500 ms train duration): 1, 20, 40, 50, 60, 80, 100, 150 Hz and maximal peak isometric force was collected and plotted.

Body Mass and Composition

Mice were subjected to Time Domain (TD)-NMR (LF90 Minispec, Bruker, Spring, TX, USA) to determine body composition of fat, lean mass, and fluid in conscious mice under randomly fed conditions. Following body mass measurements, mice were placed into a Plexiglas sample holder (90 mm in diameter and 250 mm in length), with ventilation holes provided at both ends and around the tube circumference, and inserted into the 0.5 T magnet bore. All measurements were performed in triplicate, and the average was reported. The mice are then returned to their cages upon completion of the measurements.

FSHD Mouse Model

Female FLExDUX4.CRE mice were assigned to one of two balanced groups based on body weight. Mice were dosed with vehicle or 10 mg/kg CAV-003 every 4 days for 4 weeks by intraperitoneal injection. One group of littermate CRE WT mice served as a reference control and were dosed with vehicle every 4 days for 4 weeks by intraperitoneal injection. At the end of the study, in vivo hindlimb muscle function was measured as described above and animals were euthanized for tissue collection.

Example 2. In Vitro Potency of ITGA7-Targeted IGF-1

Figure 1B:
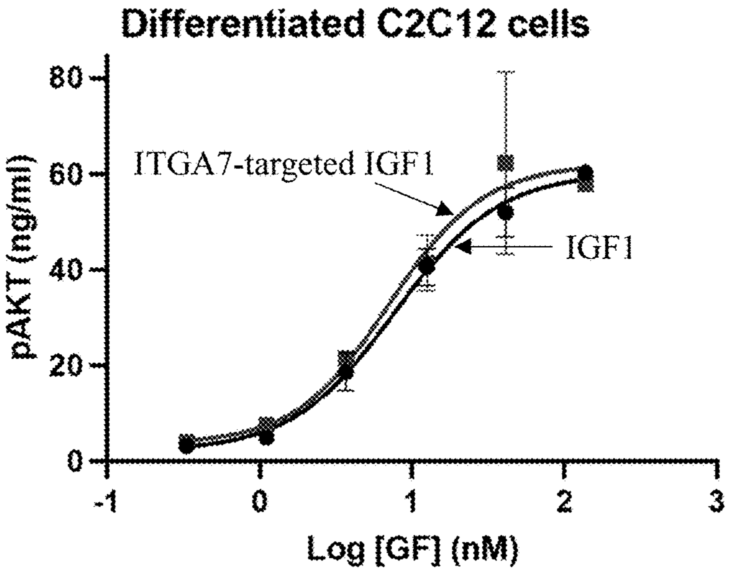
FIG. 1B depicts in vitro potency of ITGA7-targeted IGF-1 in differentiated muscle cells (C2C12) compared to that of IGF-1.

The in vitro potency of ITGA7-targeted IGF-1 (comprising three polypeptide chains: SEQ ID NOS: 2, 39, and 40) was tested in both of non-muscle cells (DU145) and differentiated muscle cells (C2C12) via pAKT assay. The half maximal effective concentration (EC50) of IGF-1 in DU145 cells was 4.6 nM and the EC50 of ITGA7-targeted IGF-1 in DU145 cells was 30.5 nM. The half maximal effective concentration (EC50) of IGF-1 in C2C12 cells was 7.8 nM and the EC50 of ITGA7-targeted IGF-1 in C2C12 cells was reduced to 7.1 nM. It indicated that ITGA7-targeted IGF-1 was more potent in differentiated muscle cells compared to non-muscle cells, as shown in FIGS. 1A and 1B.

Example 3: In Vivo Distribution of ITGA7-Targeted IGF-1

Figure 2:
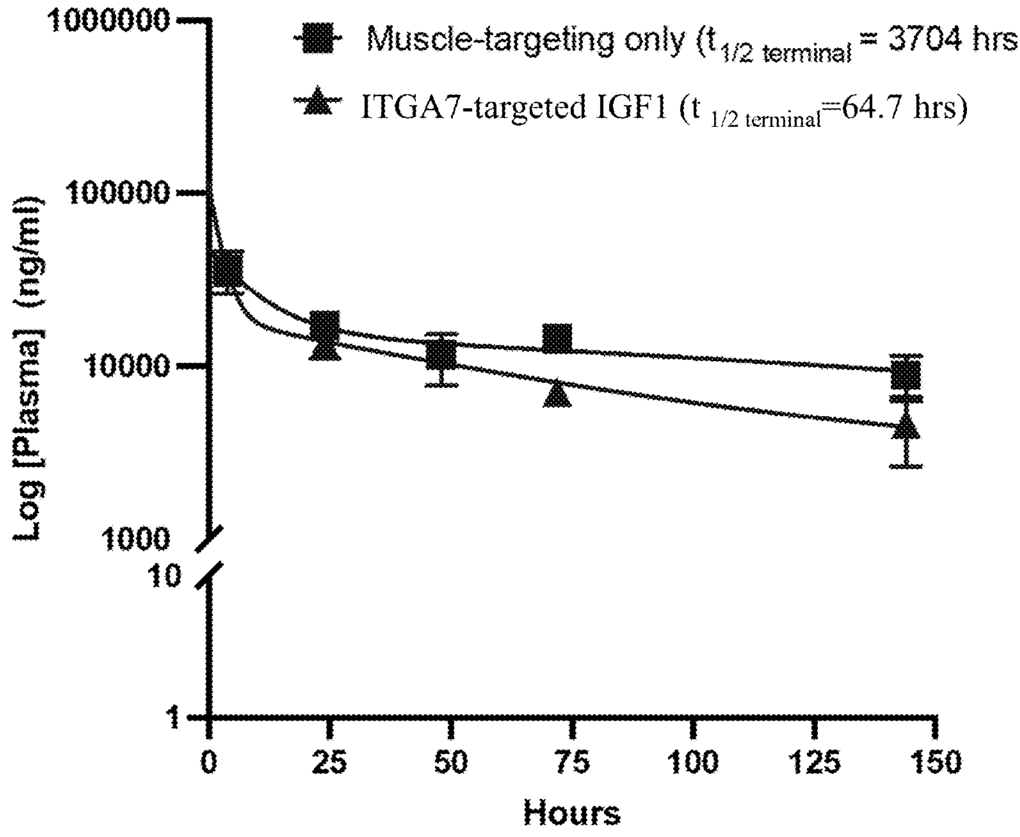
FIG. 2 depicts the plasma half-life of ITGA7-targeted IGF-1 and antibody scaffold with ITGA7-targeting arm after injection of the antibodies into mice.

Mice were injected with either antibody scaffold with ITGA7-targeting arm only or ITGA7-targeted IGF-1 (comprising SEQ ID NOS: 2, 39, and 40). Blood was collected after 0-150 hours post injection to measure pharmacokinetics of the antibodies in plasma via human IgG assay. The half-life of ITGA7-targeted IGF-1 ($t_{1/2\ terminal}$=64.7 hrs) in plasma was shorter than that of antibody scaffold with ITGA7-targeting arm only, as shown in FIG. 2. It suggested that ITGA7-targeted IGF-1 was either quickly removed from the system or relocated to other tissue or organisms.

Figure 3A:
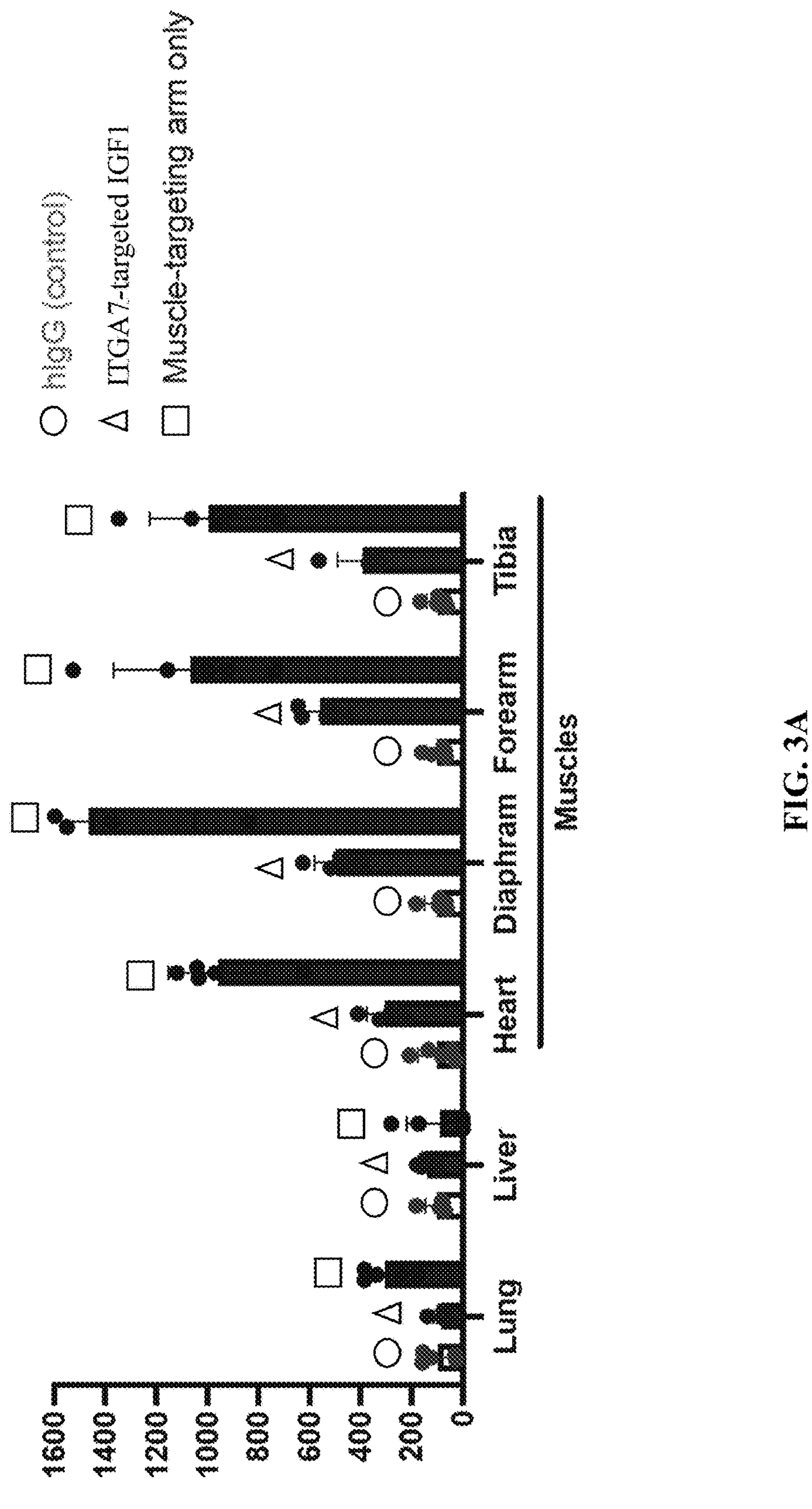
FIG. 3A depicts relative concentrations of human IgG antibody (control), ITGA7-targeted IGF-1, and antibody scaffold with ITGA7-targeting arm in lung, liver, heart, diaphragm, forearm, and tibia at 72 hours post injection of the corresponding antibodies (normalized to the control group)
Figure 3B:
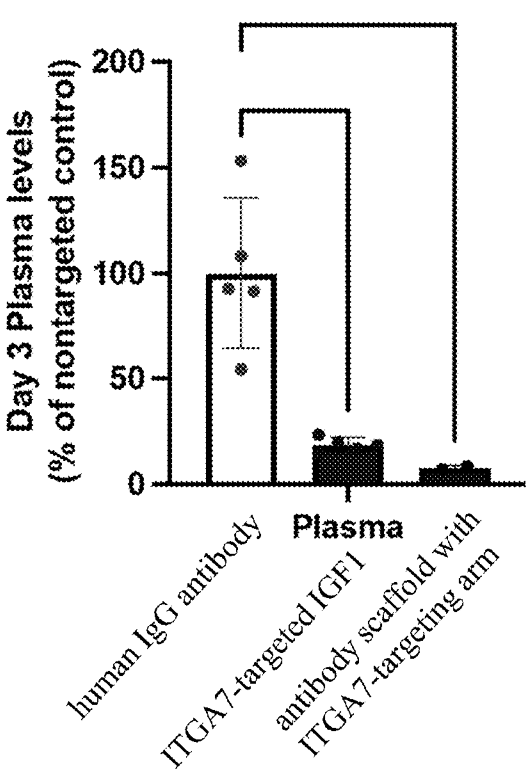
FIG. 3B depicts relative concentrations of human IgG antibody (control), ITGA7-targeted IGF-1, and antibody scaffold with ITGA7-targeting arm (corresponding to each column from left to right) in plasma at 72 hours post injection of corresponding antibodies (normalized to the control group); statistical analysis: One-way ANOVA, Dunnett's, n=5/group, *p<0.05, p<0.01.

Tissues of lung, liver, heart, diaphragm, forearm, and tibia of tested mice were harvested at 72 hours post-injection. The amount of the antibodies in the tissues was measured via human IgG assay and normalized to the amount of human IgG level in the respective tissues. The level of ITGA7-targeted IGF-1 in muscle tissues (e.g. heart, diaphragm, forearm, and tibia) was much higher than non-muscle tissues (e.g. lung and liver), as shown in FIG. 3A. In contrast, the level of ITGA7-targeted IGF-1 in plasma was lower than nonspecific human IgG control, as shown in FIG. 3B. It indicated that ITGA7-targeted IGF-1 partitioned preferentially to muscle tissues compared to nonspecific human IgG.

Figure 3C:
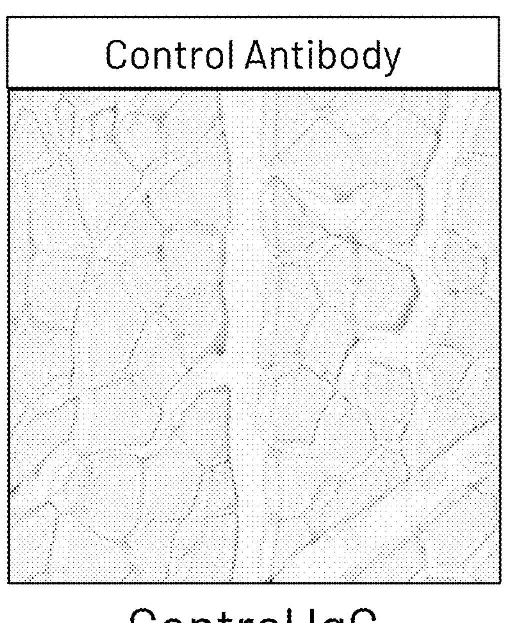
FIG. 3C depicts localization of human IgG antibody (control) and ITGA7-targeted IGF-1 to myofibers in vivo after systemic dosing via Immunohistochemistry (IHC) assay.
Figure 3C:
Figure 3C:
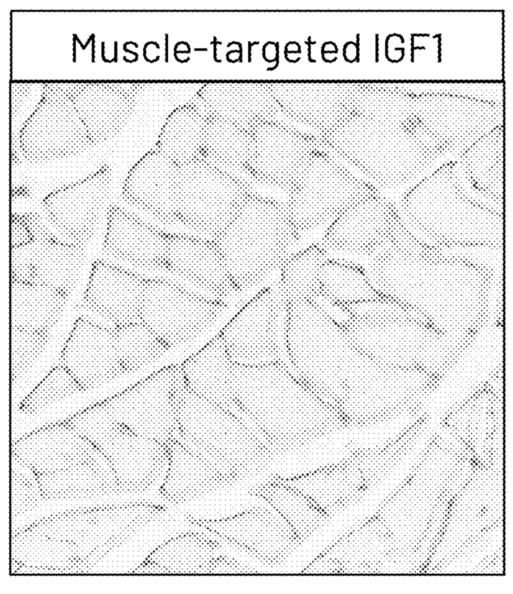

Muscles from tested mice were isolated 4-72 hours after the injection and stained for human IgG. FIG. 3C suggests that more ITGA7-targeted IGF-1 were localized to muscle tissues compared to non-specific control IgG.

Figure 3D:
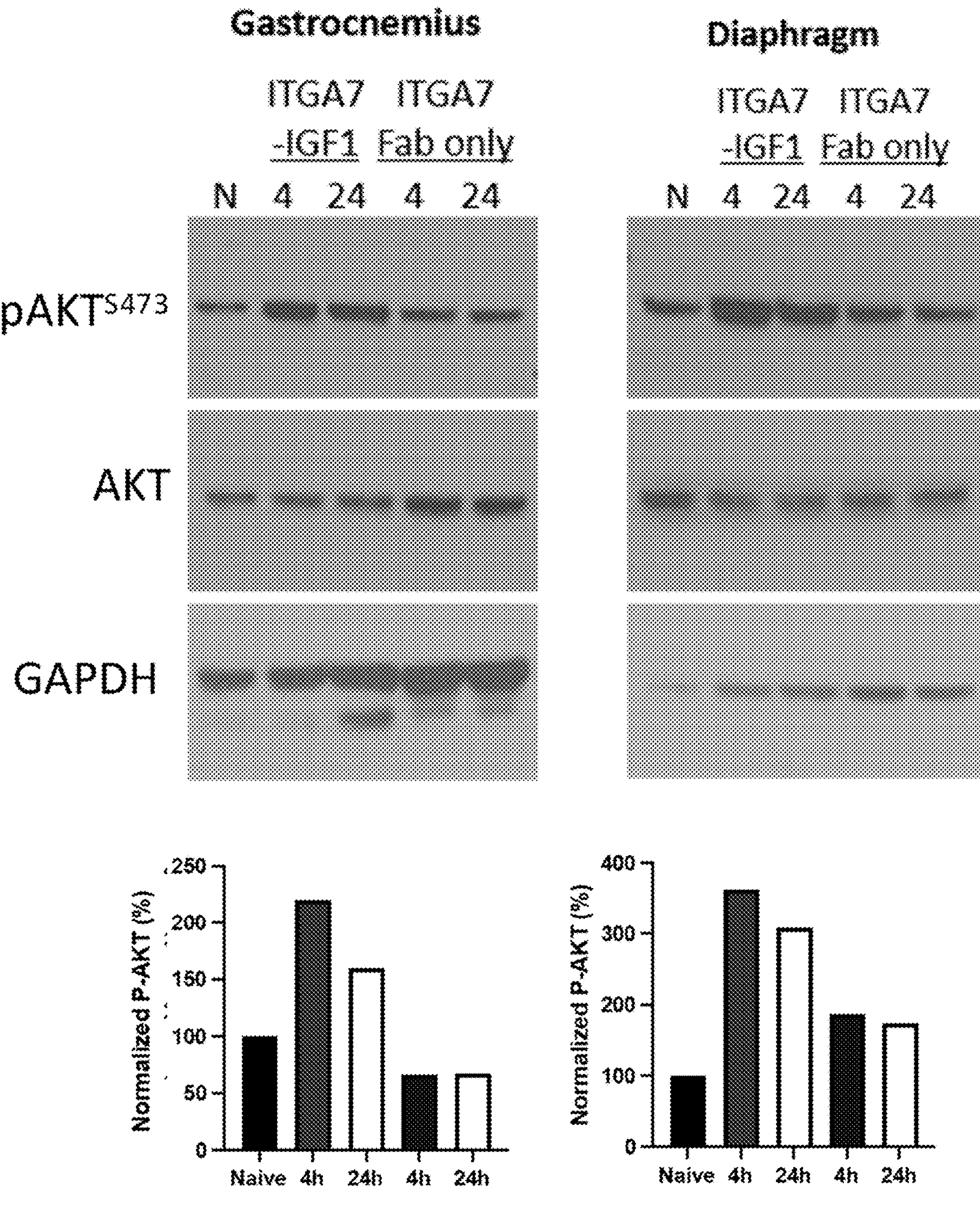
FIG. 3D depicts the expression of the phospho-Akt (S473) in gastrocnemius and diaphragm detected via western blot assay at 4 h and 24 h post injection of ITGA7 targeting Fab only or ITGA7-targeted IGF-1 and its quantification normalized to the baseline level.
Figure 3E:
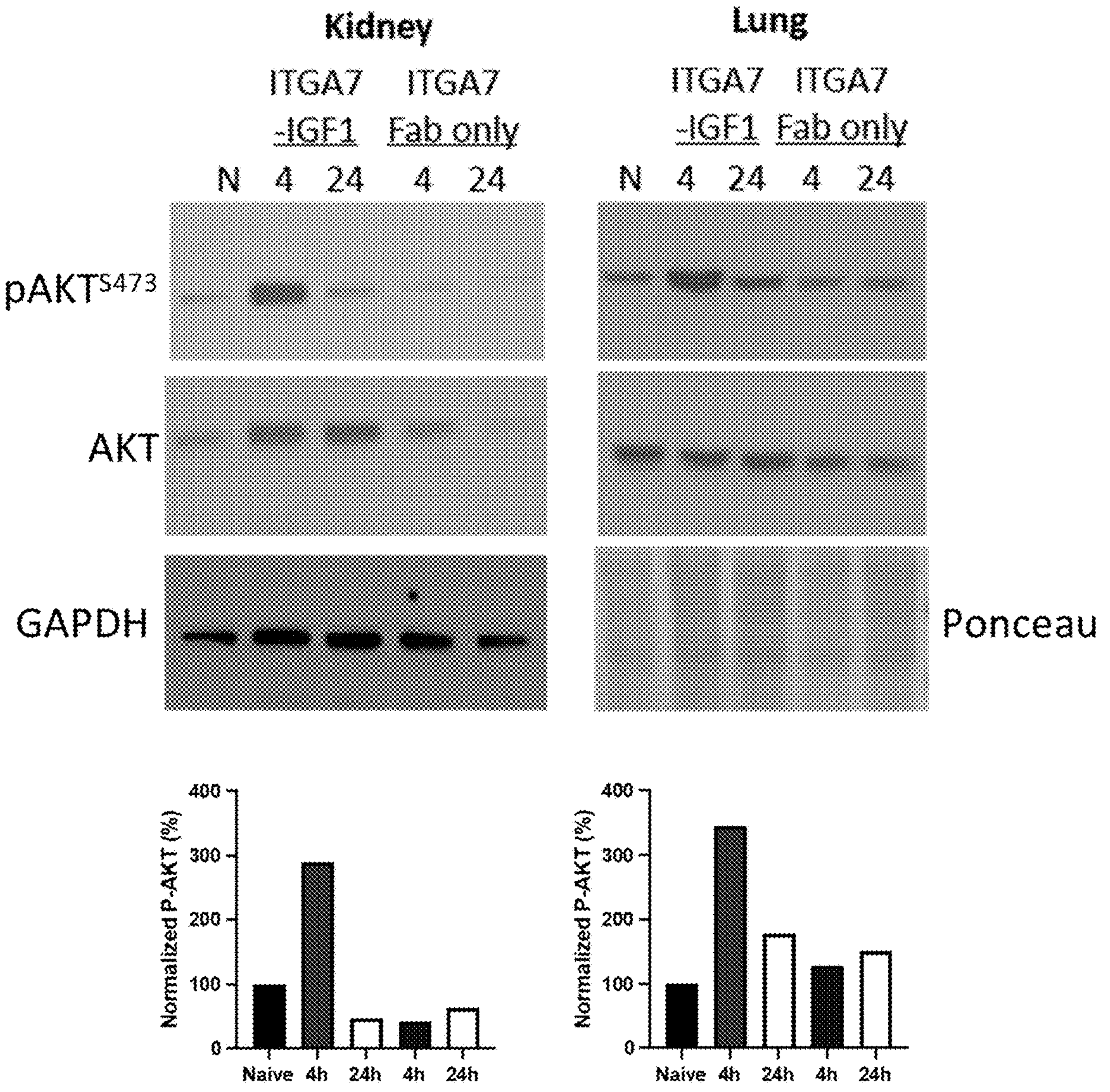
FIG. 3E depicts the expression of the phospho-Akt (S473) in kidney and lung detected via western blot assay at 4 h and 24 h post injection of human IgG antibody or ITGA7-targeted IGF-1 and its quantification normalized to the baseline level.
Figure 4:
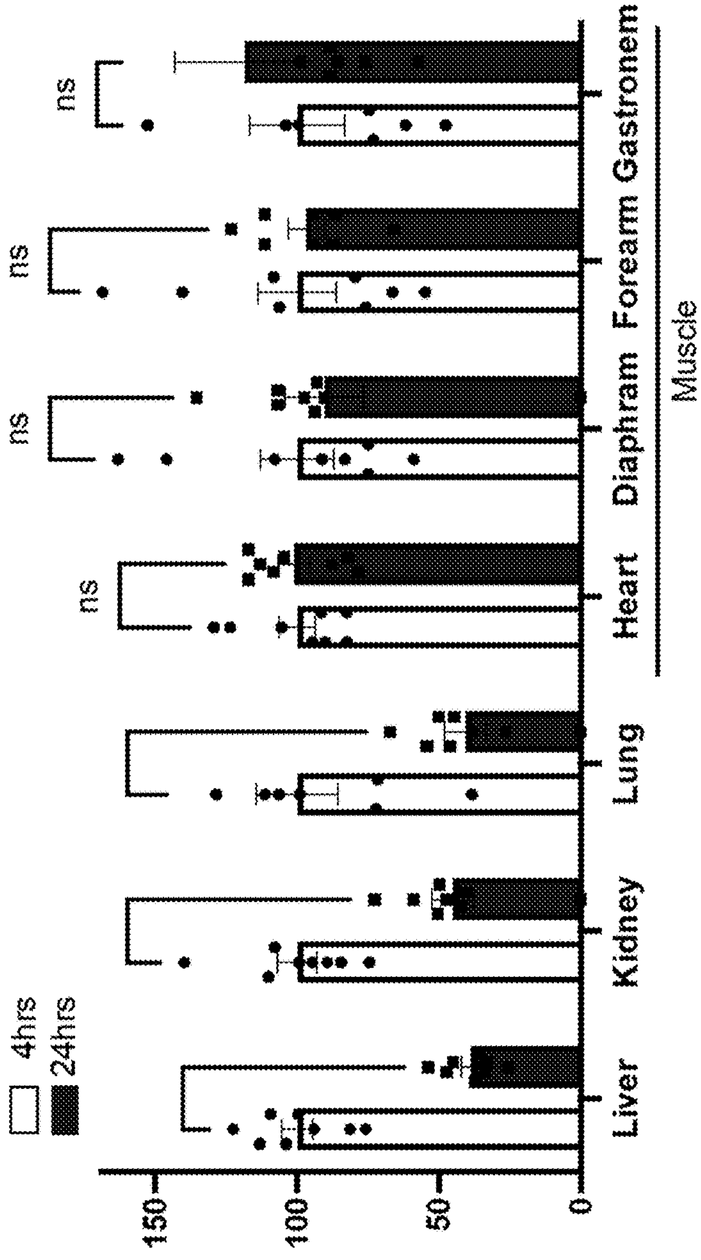
FIG. 4 depicts relative concentration of ITGA7-targeted IGF-1 in plasma, lung, liver, kidney, heart, diaphragm, forearm, and gastrocnemius at 4 hours and 24 hours post injection of the corresponding antibodies (normalized to the control group); statistical analysis: Two-way ANOVA, Sidak's multiple comparisons, 4 hrs vs 24 hrs, n=7/group, *p<0.05, p<0.01.
Figure 4:
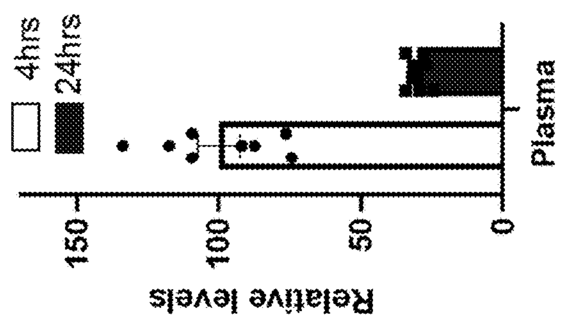

Tissues from test mice were harvested 4-24 hours post injection and measured for ITGA7-targeted IGF-1 via pAKT assay and western blot assay. Muscle tissues (e.g., gastrocnemius, diaphragm) exhibited prolonged pAKT compared to non-muscle tissues (e.g., kidney, lung), as shown in FIGS. 3D and 3E. Tissues from tested mice were harvested at 4 hours and 24 hours post injection and measured for the antibodies via pAKT assay. The concentrations of ITGA7-targeted IGF-1 at 24 hours post-injection were normalized to the concentrations at 4 hours post-infection. The concentrations of ITGA7-targeted IGF-1 at 24 hours post-injection were higher in muscle tissues (e.g., heart, diaphragm, forearm, and gastrocnemius) compared to non-muscle tissues (e.g. liver, kidney, and lung), as shown in FIG. 4. It suggested that ITGA7-targeted IGF-1 persists longer in muscle tissues than non-muscle tissues.

Figure 5A:
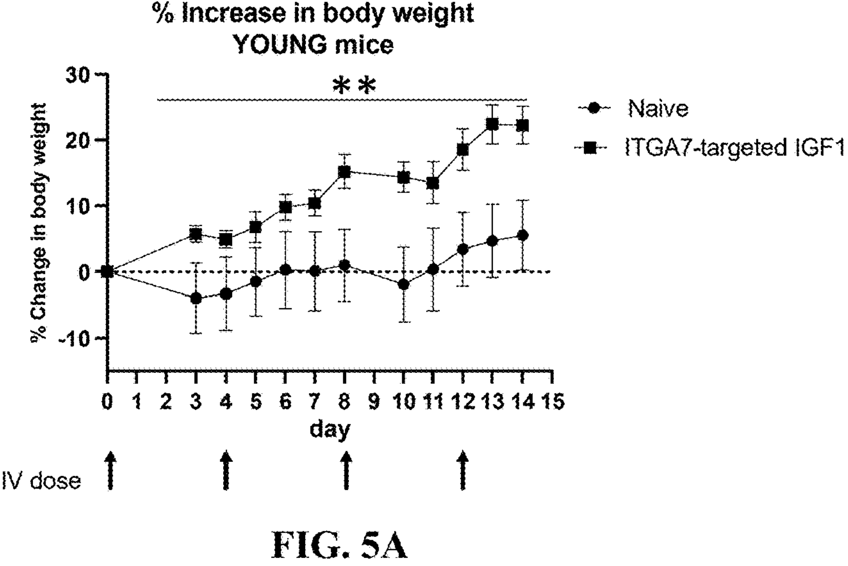
FIGS. 5A-5C show increases in body and muscle weight of young mice upon treatment with ITGA7-targeted IGF-1 fusion molecule.
Figure 5B:
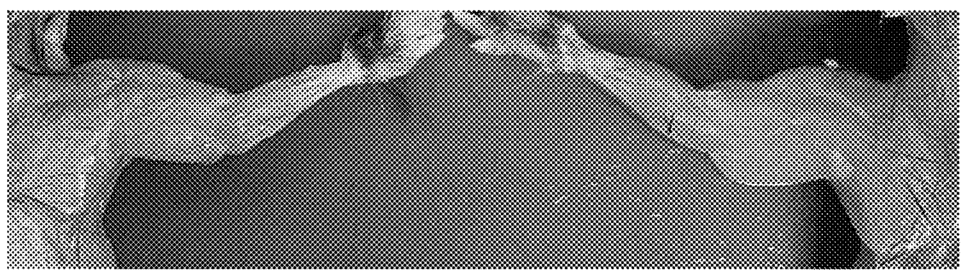
Figure 5C:
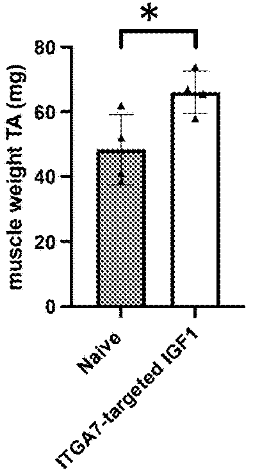

Example 4: ITGA7-Targeted IGF-1 Increases Body and Muscle Weights in Young and Aged Mice To evaluate effects of ITGA7-targeted IGF-1 (comprising three polypeptide chains: SEQ ID NOS: 2, 39, and 40) on body and muscle weights, young mice (under 18 months old) were dosed every 4 days at 10 mg/kg via intravenous route with ITGA7-targeted IGF-1 fusion molecule. FIG. 5A shows increased percentage of body weight from baseline during 14 days of treatment above naïve animals. FIG. 5B shows a qualitative increase in forearm muscle size in ITGA7-targeted IGF-1 treated mice compared to naïve mice at end of 14 days of treatment. FIG. 5C shows a significant increase in isolated tibialis anterior (TA) muscle weight in ITGA7-targeted IGF-1 treated mice compared to naïve mice. The results suggest that ITGA7-targeted IGF-1 increases body and muscle weights in young mice.

Figure 6A:
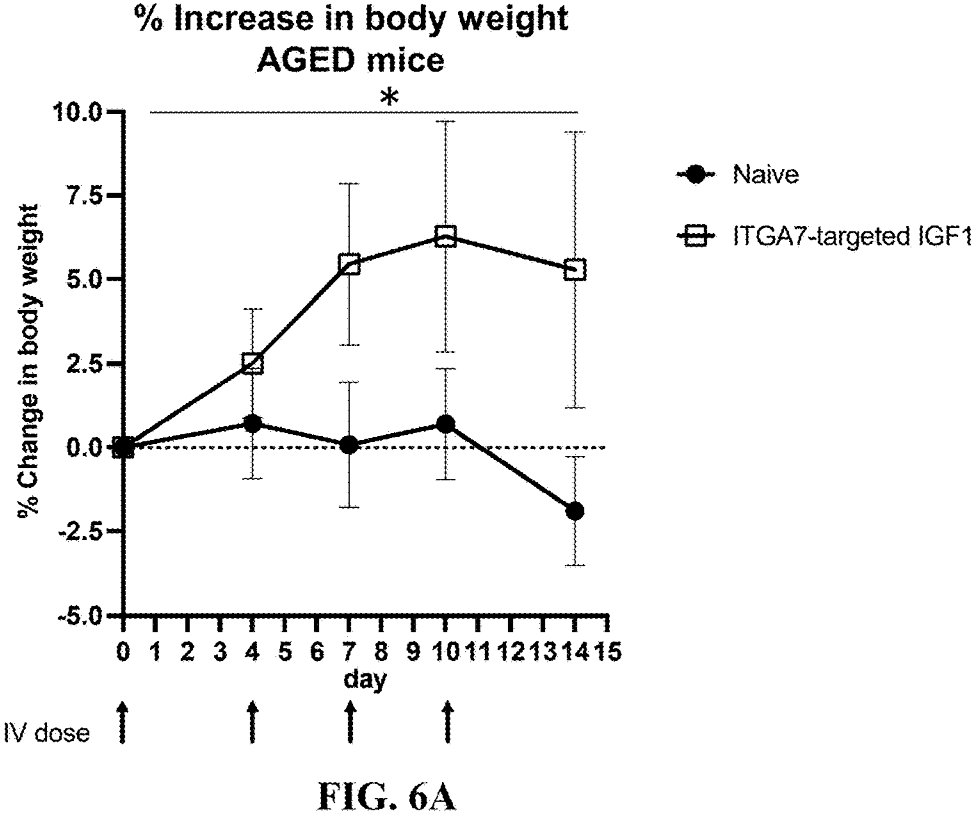
FIGS. 6A-6B show the results of body and muscle weight of aged mice upon intravenous treatment with ITGA7-targeted IGF-1 fusion molecule every 4 days for 14 days of treatment.
Figure 6B:
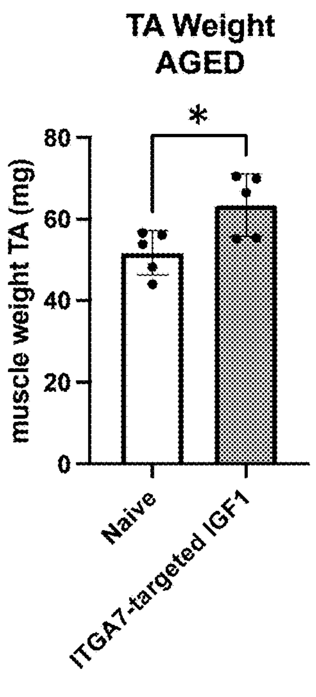

To evaluate effects of ITGA7-targeted IGF-1 on body and muscle weights, aged mice (18 months old) were dosed every 4 days at 10 mg/Kg via intravenous route with ITGA7-targeted IGF-1 fusion molecule. FIG. 6A shows increased percentage of body weight from baseline during 14 days of treatment as compared to naïve animals. FIG. 6B shows a significant increase in isolated tibialis anterior (TA) muscle weight in ITGA7-targeted IGF-1 fusion molecule treated mice compared to naïve mice. The results suggest that ITGA7-targeted IGF-1 increases body and muscle weights in aged mice.

Figure 7:
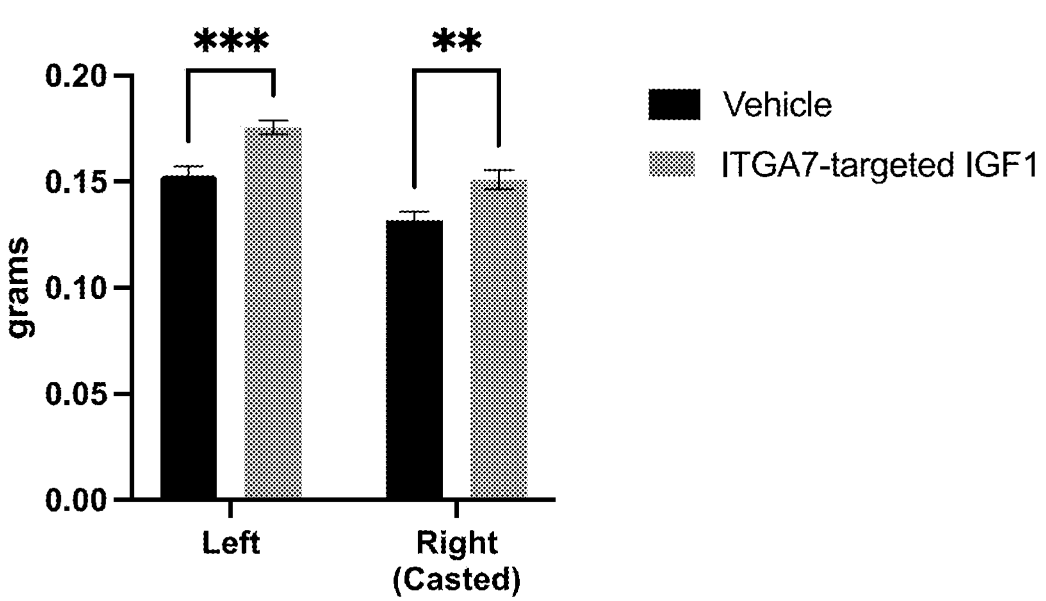
FIG. 7 shows the results of mice in a hindlimb casting atrophy model who were treated with ITGA7-targeted IGF1 fusion molecule. Specifically, mice had their right leg immobilized in a cast for 2 weeks, during which time ITGA7-targeted IGF1 fusion molecule was administered every 4 days at 10 mg/kg via intraperitoneal route. This was followed by gastrocnemius muscle dissection and weight measurement. Results showed an increase in muscle mass in both the uncasted (left) and casted (right) muscles of ITGA7-targeted IGF-1 fusion molecule treated mice compared to vehicle-treated group. The statistical analysis in FIG. 7 uses unpaired t-test, n=10/group, *p<0.05, **p<0.01.

Example 5: ITGA7-Targeted IGF-1 Increases Muscle Weight in Hindlimb Casting Atrophy Model Mice had their right leg immobilized in cast for 2 weeks during which time ITGA7-targeted IGF-1 (comprising three polypeptide chains: SEQ ID NOS: 2, 39, and 40) was administered every 4 days at 10 mg/kg via intraperitoneal route, followed by gastrocnemius muscle dissection and weight measurement. FIG. 7 shows that ITGA7-targeted IGF-1 treated mice had a significant increase in muscle mass in both uncasted (left) and casted (right) muscles compared to vehicle group.

Figure 8A:
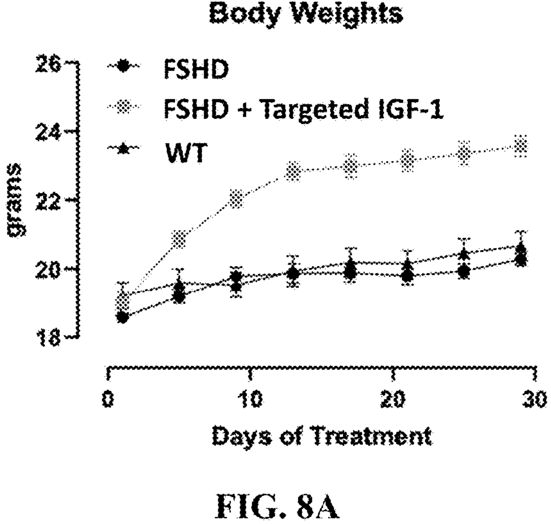
FIGS. 8A-8C show increases in body muscle weight and force generation of facioscapulohumeral muscular dystrophy (FSHD) transgenic mice upon treatment of ITGA7-targeted IGF-1 fusion molecule compared to wild-type mice and untreated FSHD mice.
Figure 8B:
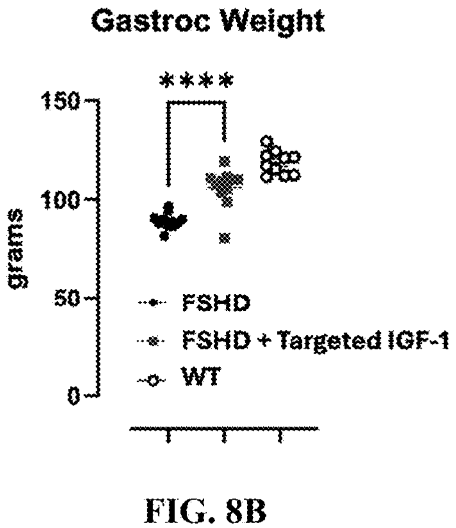
Figure 8C:
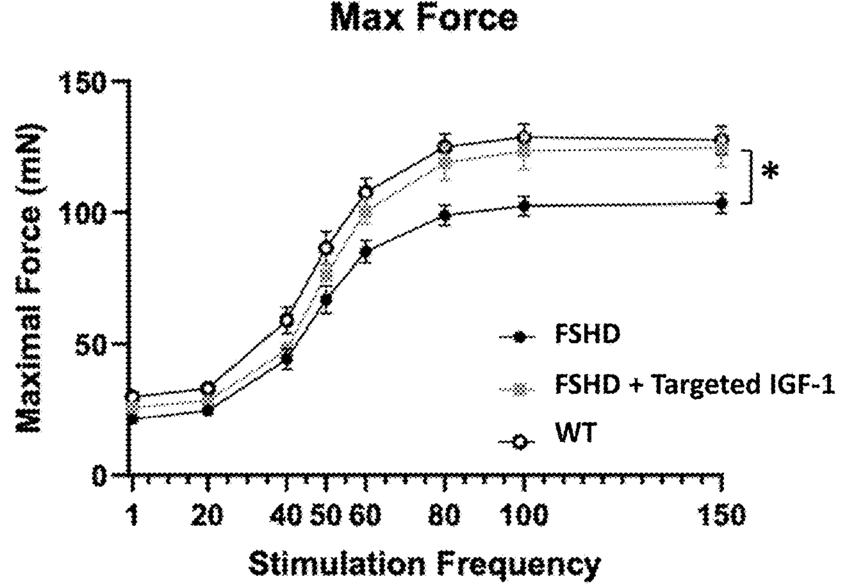

Example 6: ITGA7-Targeted IGF-1 Increases Body Muscle Weight that Results in Increased Force Generation in Facioscapulohumeral Muscular Dystrophy (FSHD) Transgenic Mice FSHD mice were dosed every 4 days at 10 mg/kg via intraperitoneal route with ITGA7-targeted IGF-1 (comprising three polypeptide chains: SEQ ID NOS: 2, 39, and 40). FIG. 8A shows that the treated FSHD mice increased percentage of body weight from baseline during 14 days of treatment above untreated FSHD and wildtype (WT) vehicle-treated mice. FIG. 8B shows a significant increase in isolated gastrocnemius (Gastroc) muscle weight of ITGA7-targeted IGF-1 treated FSHD mice compared to untreated FSHD and wildtype (WT) vehicle-treated mice. FIG. 8C shows a significant increase in max force generation of ITGA7-targeted IGF-1 treated FSHD mice compared to untreated FSHD and wildtype (WT) vehicle-treated mice. The max force was measured by plantar flexor muscle force measurements.

Figure 9A:
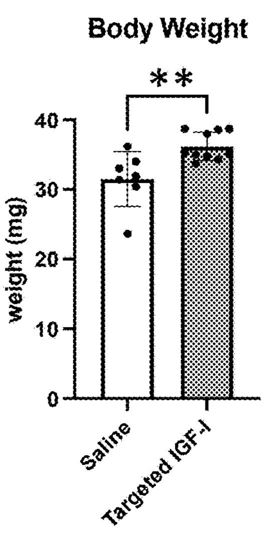
FIGS. 9A-9C show increases in body and muscle weights and changes of body composition in adult mice after 1 month treatment of ITGA7-targeted IGF-1.
Figure 9B:
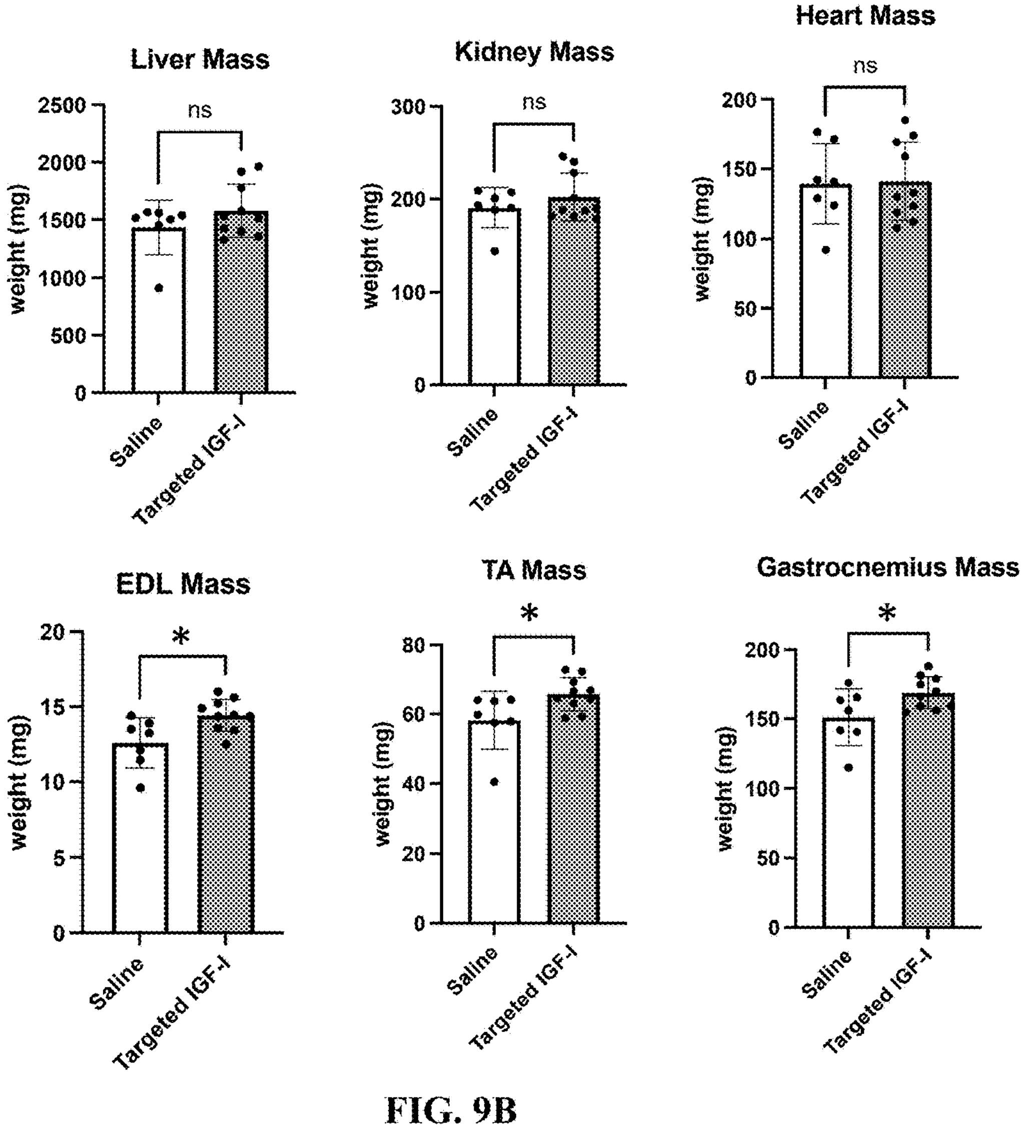
Figure 9C:
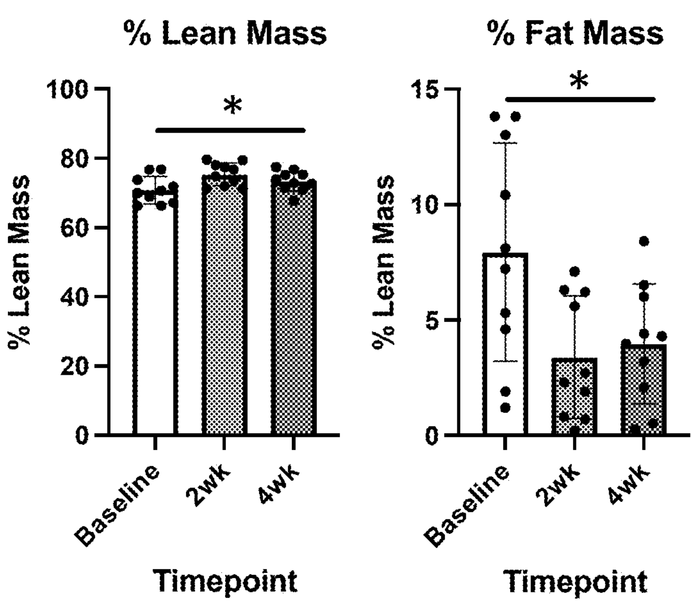

Example 7: ITGA7-Targeted IGF-1 Increases Body and Muscle Weights and Changes Body Composition after 1 Month of Treatment Adult mice (6 months old) were dosed every 4 days at 10 mg/kg via intraperitoneal route for 28 days with ITGA7-targeted IGF-1 fusion molecule (comprising three polypeptide chains: SEQ ID NOS: 2, 39, and 40). FIG. 9A shows that the mice had a significant increase in body weight compared to vehicle (saline) treated animals. FIG. 9B shows that isolated organs (liver, kidney, and heart) did not show differences in weight between treated and vehicle groups. Isolated skeletal muscles, including extensor digitorum longus (EDL), tibialis anterior (TA), and gastrocnemius, all showed significant increases in mass compared to vehicle treated animals. Time domain nuclear magnetic resonance was used to measure total body lean and fat mass content. FIG. 9C suggests that the treated mice showed a significant increase from baseline compared to 2 week and 4 week post-treatment in lean mass percentage and decrease in fat mass percentage.

Example 8: In Vitro Potency of ITGA7-Targeted IGF-1 Compared to Variants with Potency Reducing Mutations in IGF-1

Figure 10:
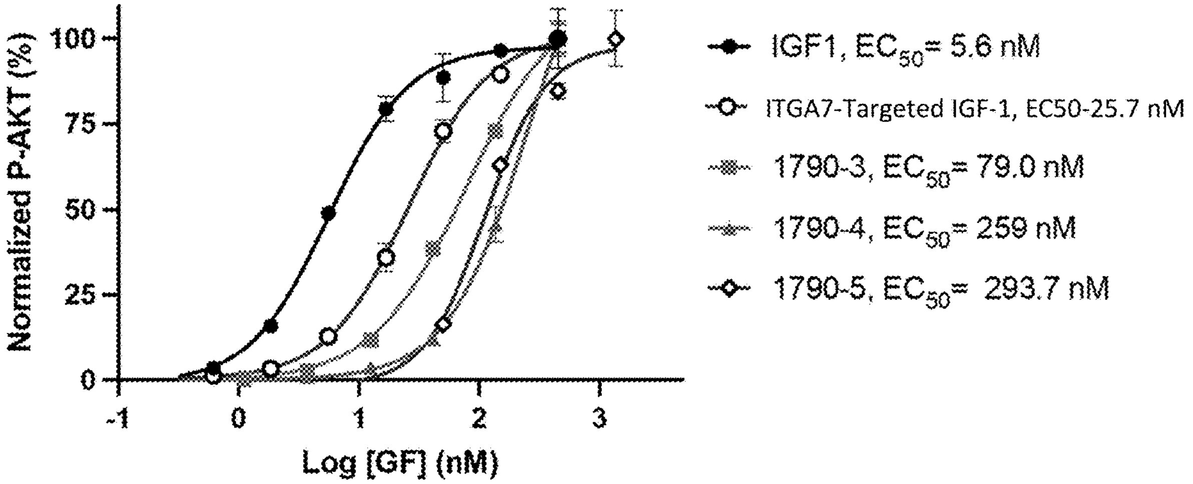
FIG. 10 shows the results of an in vitro potency assay measuring in vitro potency of ITGA7-targeted IGF-1 compared to variants with potency reducing mutations in IGF-1. $EC_{50}$ values of IGF-1, ITGA7-targeted IGF-1, and their variants (1790-3, 1790-4, 1790-5) are provided.

ITGA7-targeted IGF-1 (comprising three polypeptide chains: SEQ ID NOS: 2, 39, and 40) and their variants with potency reducing mutations in IGF-1 (1790-3, 1790-4, 1790-5) were assayed for potency in a DU145 potency assay. 1790-3 (comprising three polypeptide chains: SEQ ID NOS: 46, 51, and 52) comprises a R37 deletion relative to ITGA7-targeted IGF-1. 1790-4 (comprising three polypeptide chains: SEQ ID NOS: 47, 53, and 54) comprises a Y24L mutation relative to ITGA7-targeted IGF-1. 1790-5 (comprising three polypeptide chains: SEQ ID NOS: 48, 55, and 56) comprises a Y31A mutation relative to ITGA7-targeted IGF-1. DU145 cells were stimulated for 15 minutes with the indicated molecule followed by measurement of phosphorylated AKT (P-AKT) levels via ELISA method. FIG. 10 shows the $EC_{50}$ values of IGF-1, ITGA7-targeted IGF-1, and their mutants, which were calculated in GraphPad Prism.

Figure 11A:
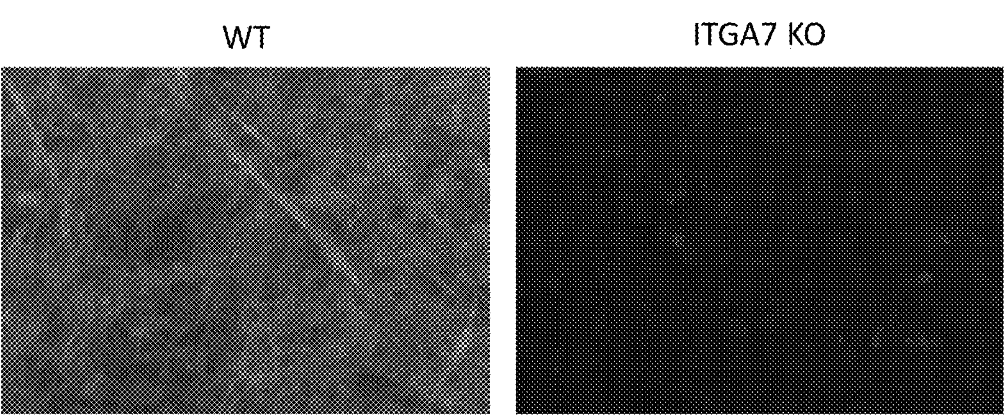
FIGS. 11A-11C show the results of in vitro potency assays of ITGA7-targeted IGF-1 and variants with potency reducing mutations in IGF-1 in wild-type C2C12 cells compared to ITGA7 knockout (KO) C2C12 cells.
Figure 11B:
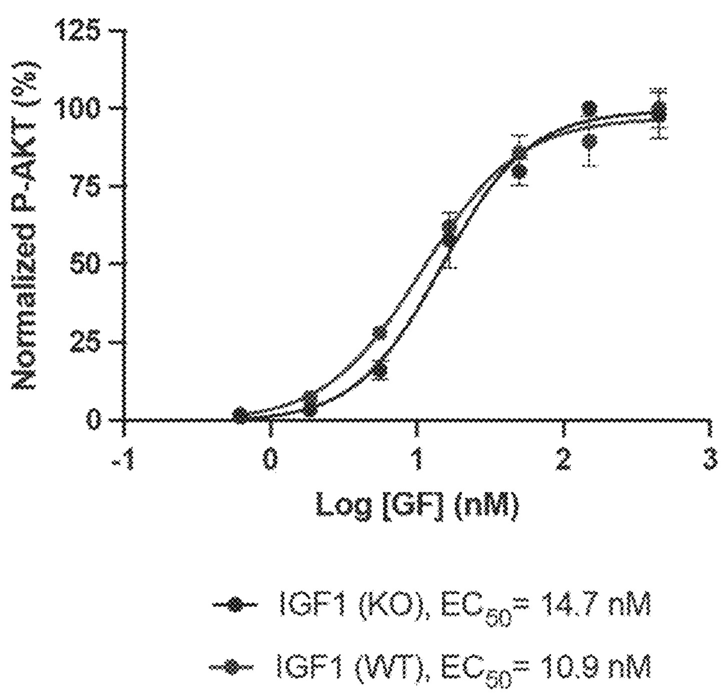
Figure 11C:
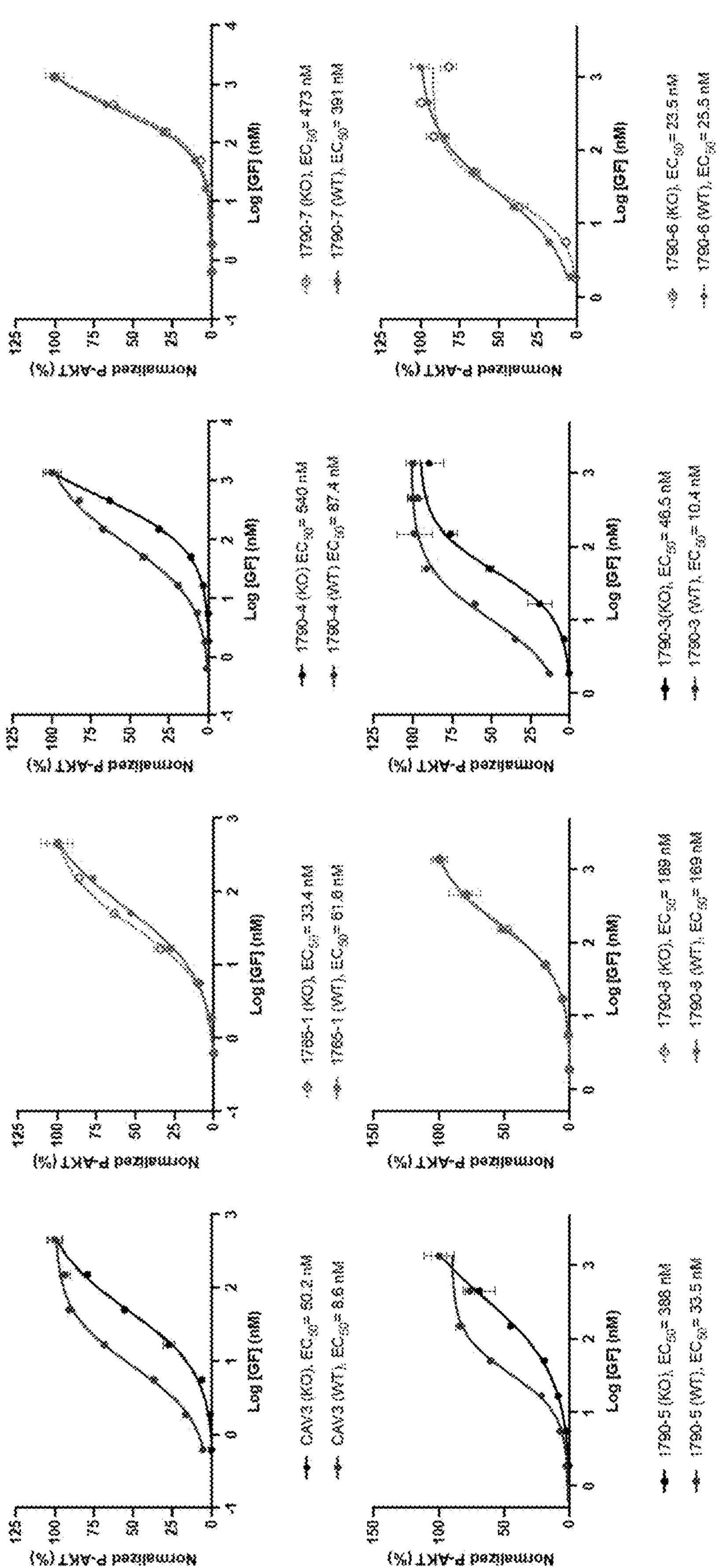

Example 9: ITGA7-Targeted IGF-1 and Variants with Potency Reducing Mutations in IGF-1 are More Potent in WT C2C12 Cells Compared to ITGA7 Knockout (KO) C2C12 Cells ITGA7-targeted IGF-1 (comprising three polypeptide chains: SEQ ID NOS: 2, 39, and 40) and variants with potency reducing mutations in IGF-1 (1790-3, 1790-4, 1790-5) or their non-ITGA7 targeting controls (1765-1, 1790-7, 1790-6) were assayed for in WT C2C12 cells or ITGA7 KO C2C12 cells generated by using the Alt-R CRISPR-Cas9 System. 1790-3 (comprising three polypeptide chains: SEQ ID NOS: 46, 51, and 52) comprises a R37 deletion relative to ITGA7-targeted IGF-1. 1790-4 (comprising three polypeptide chains: SEQ ID NOS: 47, 53, and 54) comprises a Y24L mutation relative to ITGA7-targeted IGF-1. 1790-5 (comprising three polypeptide chains: SEQ ID NOS: 48, 55, and 56) comprises a Y31A mutation relative to ITGA7-targeted IGF-1. 1765-1 comprises wild-type IGF-1. 1790-6 (comprising three polypeptide chains: SEQ ID NOS: 49, 57, and 58) comprises a R37 deletion relative to ITGA7-targeted IGF-1. 1790-7 (comprising three polypeptide chains: SEQ ID NOS: 50, 59, and 60) comprises a Y24L mutation relative to ITGA7-targeted IGF-1. FIG. 11A shows immunofluorescent detection of ITGA7 using 1707-4 (ITGA7 antibody) in WT or ITGA7 KO C2C12 cells. FIG. 11B shows the phosphorylated AKT (P-AKT) levels measured via ELISA method, after WT and ITGA7 KO C2C12 cells were stimulated for 15 minutes with IGF-1. FIG. 11C shows the phosphorylated AKT (P-AKT) levels measured by ELISA method, after WT and ITGA7 KO C2C12 cells were stimulated for 15 minutes with ITGA7-targeted IGF-1 or an IGF-1 variant. EC50 values were calculated in GraphPad Prism. FIGS. 11A-11C suggest that ITGA7-targeted IGF-1 and variants with potency reducing mutations in IGF-1 are more potent in WT C2C12 cells compared to ITGA7 knockout (KO) C2C12 cells.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

What is claimed is:

1. An agent for selectively targeting muscle, the agent comprising (a) an antigen-binding domain comprising an antibody or antigen-binding portion thereof that selectively binds to a mammalian ITGA7 and (b) an IGF-1 polypeptide that is coupled to the antigen-binding domain.

2. The agent of claim 1, wherein the agent selectively targets a muscle cell.

3. The agent of claim 1, wherein the antigen-binding domain binds to an epitope of ITGA7 expressed in a mammalian cell selected from the group consisting of a muscle satellite cell, a skeletal muscle cell, a cardiac muscle cell, and a muscle fiber.

4. The agent of claim 1, wherein the antigen-binding domain comprises a fragment antigen-binding (Fab) domain or a single chain variable fragment (scFv).

5. The agent of claim 1, further comprising a linker, wherein the linker couples the IGF-1 polypeptide to the antigen-binding domain that selectively binds to the mammalian ITGA7.

6. The agent of claim 1, wherein the antigen-binding domain comprises further comprising a fragment crystallizable domain (Fc domain).

7. The agent of claim 6, wherein the Fc domain is a human IgG1 Fc domain.

8. The agent of claim 6, wherein the Fc domain comprises a knob-in-hole.

9. The agent of claim 1, wherein the antigen-binding domain comprises (i) a human IgG1 heavy chain with knob mutations and a N297G mutation and (ii) a light chain.

10. The agent of claim 1, wherein the IGF-1 polypeptide is coupled to an amino terminus of the antigen binding domain.

11. The agent of claim 1, wherein the IGF-1 polypeptide is coupled to a carboxy terminus of the antigen binding domain.

12. A pharmaceutical composition comprising (i) the agent of claim 1 and (ii) one or more pharmaceutically acceptable excipients.

13. The agent of claim 1, wherein the IGF-1 polypeptide comprises the amino acid sequence of SEQ ID NO: 1.

* * * * *